United States Patent
Hinrichs et al.

(10) Patent No.: US 12,157,762 B2
(45) Date of Patent: *Dec. 3, 2024

(54) TETHERED INTERLEUKIN-15 AND INTERLEUKIN-21

(71) Applicant: The United States of America, as represented by the Secretary, Department of Health and Human Services, Bethesda, MD (US)

(72) Inventors: Christian S. Hinrichs, Princeton, NJ (US); Benjamin Y. Jin, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/310,744

(22) Filed: May 2, 2023

(65) Prior Publication Data

US 2023/0355677 A1 Nov. 9, 2023

Related U.S. Application Data

(63) Continuation of application No. 16/964,796, filed as application No. PCT/US2019/016975 on Feb. 7, 2019.

(60) Provisional application No. 62/628,454, filed on Feb. 9, 2018.

(51) Int. Cl.
| | |
|---|---|
| *C12N 15/867* | (2006.01) |
| *A61K 39/00* | (2006.01) |
| *C07K 14/54* | (2006.01) |
| *C07K 14/705* | (2006.01) |
| *C07K 14/725* | (2006.01) |
| *C12N 15/62* | (2006.01) |

(52) U.S. Cl.
CPC ...... *C07K 14/7051* (2013.01); *A61K 39/4611* (2023.05); *A61K 39/4631* (2023.05); *A61K 39/4632* (2023.05); *A61K 39/46444* (2023.05); *A61K 39/464491* (2023.05); *A61K 39/464838* (2023.05); *C07K 14/5443* (2013.01); *C12N 15/62* (2013.01); *C12N 15/867* (2013.01); *A61K 2239/31* (2023.05); *A61K 2239/38* (2023.05); *A61K 2239/59* (2023.05); *C07K 2319/03* (2013.01)

(58) Field of Classification Search
CPC ........ A61K 35/17; A61K 39/00; C12N 15/86; C07K 15/7051; C07K 14/5443
See application file for complete search history.

(56) References Cited

U.S. PATENT DOCUMENTS

| | | |
|---|---|---|
| 7,820,174 B2 | 10/2010 | Wang et al. |
| 7,915,036 B2 | 3/2011 | Morgan et al. |
| 8,088,379 B2 | 1/2012 | Robbins et al. |
| 8,216,565 B2 | 7/2012 | Restifo et al. |
| 8,431,690 B2 | 4/2013 | Wang et al. |
| 8,465,743 B2 | 6/2013 | Rosenberg et al. |
| 8,613,932 B2 | 12/2013 | Restifo et al. |
| 8,785,601 B2 | 7/2014 | Rosenberg et al. |
| 8,871,906 B2 | 10/2014 | Pastan et al. |
| 9,128,080 B2 | 9/2015 | Robbins et al. |
| 9,266,960 B2 | 2/2016 | Morgan et al. |
| 9,345,748 B2 | 5/2016 | Morgan et al. |
| 9,359,447 B2 | 6/2016 | Feldman et al. |
| 9,487,573 B2 | 11/2016 | Parkhurst et al. |
| 9,765,342 B2 | 9/2017 | Kochenderfer |
| 9,822,162 B2 | 11/2017 | Hinrichs et al. |
| 9,868,774 B2 | 1/2018 | Orentas et al. |
| 2003/0099932 A1 | 5/2003 | Lorens et al. |
| 2012/0101148 A1 | 4/2012 | Aking et al. |
| 2013/0071414 A1* | 3/2013 | Dotti ............... C12N 5/0638 435/320.1 |
| 2013/0116167 A1 | 5/2013 | Morgan et al. |
| 2014/0378389 A1 | 12/2014 | Robbins et al. |
| 2015/0246959 A1 | 9/2015 | Robbins et al. |
| 2017/0107286 A1 | 4/2017 | Kochenderfer |
| 2017/0145070 A1 | 5/2017 | Hinrichs et al. |

FOREIGN PATENT DOCUMENTS

| | | |
|---|---|---|
| CN | 103083660 A | 5/2013 |
| CN | 107207615 A | 9/2017 |
| WO | WO 2005/014642 A2 | 2/2005 |
| WO | WO 2012/127464 A2 | 9/2012 |
| WO | WO 2016/073755 A2 | 5/2016 |
| WO | WO 2017/189254 A1 | 11/2017 |

OTHER PUBLICATIONS

Escherich et al., Pediatr Blood Cancer 2013: 60:254-257 (Year: 2013).*
Chng et al., "Cleavage efficient 2A peptides for high level monoclonal antibody expression in CHO cells", *mAbs*, 7(2): 403-412 (2015).
De Giorgi et al., "Co-expression of functional human Heme Oxygenase 1, Ecto-5'-Nucleotidase and ecto-nucleoside triphosphate diphosphohydrolase-1 by "self-cleaving" 2A peptide system", *Plasmid*, 79: 22-29 (2015).
Dou (ed.): "Common Knowledge Evidence 1: Immunocytology and Disease", *China Medical Science and Technology Press*, p. 883 (2004).

(Continued)

*Primary Examiner* — Maryam Monshipouri
(74) *Attorney, Agent, or Firm* — Leydig, Voit & Mayer

(57) ABSTRACT

Disclosed are nucleic acids and polypeptides which provide the co-expression of interleukin (IL)-21 and IL-15 by a host cell, each interleukin being bound to the cell membrane by a cell membrane anchor moiety. Also disclosed are related recombinant expression vectors, host cells, populations of cells, pharmaceutical compositions, and methods of treating or preventing cancer.

8 Claims, 22 Drawing Sheets

Specification includes a Sequence Listing.

(56) References Cited

OTHER PUBLICATIONS

Denman et al., "Membrane-Bound IL-21 Promotes Sustained Ex Vivo Proliferation of Human Natural Killer Cells," *PLoS One*, 7(1): 30264 (2012).
Duckert et al., "Prediction of Proprotein Convertase Cleavage Sites," *Protein Eng. Des. Sel.*, 17(1): 107-112 (2004).
Floros et al., "Anticancer Cytokines: Biology and Clinical Effects of IFN-α2, IL-2, IL-15, IL-21, and IL-12," *Semin. Oncol.*, 42(4): 539-548 (2015).
GenBank Accession No. AAU88182.1 "interleukin 21 [*Homo sapiens*]," (2004).
GenBank Accession No. EAX05226.1 "interleukin 21 [*Homo sapiens*]," (2015).
GenBank Accession No. CAI94500.1 "unnamed protein product [*Homo sapiens*]," (2005).
GenBank Accession No. CAJ47524.1 "unnamed protein product [*Homo sapiens*]," (2006).
GenBank Accession No. CAL81203.1 "unnamed protein product [*Homo sapiens*]," (2006).
GenBank Accession No. CAN87399.1 "unnamed protein product [*Homo sapiens*]," (2007).
GenBank Accession No. CAS03522.1 "unnamed protein product [*Homo sapiens*]," (2008).
GenBank Accession No. CAV33288.1 "unnamed protein product [*Homo sapiens*]," (2008).
GenBank Accession No. CBE74752.1 "unnamed protein product [*Homo sapiens*]," (2009).
GenBank Accession No. CBI70418.1 "unnamed protein product [*Homo sapiens*]," (2009).
GenBank Accession No. CBI85469.1 "unnamed protein product [*Homo sapiens*]," (2010).
GenBank Accession No. CBI85472.1 "unnamed protein product [*Homo sapiens*]," (2010).
GenBank Accession No. CBL93962.1 "unnamed protein product [*Homo sapiens*]," (2010).
GenBank Accession No. CCA63962.1 "unnamed protein product [*Homo sapiens*]," (2011).
GenBank Accession No. AAG29348.1 "interleukin 21 [*Homo sapiens*]," (2000).
GenBank Accession No. AAH66258.1 "interleukin 21 [*Homo sapiens*]," (2006).
GenBank Accession No. AAH66259.1 "interleukin 21 [*Homo sapiens*]," (2006).
GenBank Accession No. AAH66260.1 "interleukin 21 [*Homo sapiens*]," (2006).
GenBank Accession No. AAH66261.1 "interleukin 21 [*Homo sapiens*]," (2006).
GenBank Accession No. AAH66262.1 "interleukin 21 [*Homo sapiens*]," (2006).
GenBank Accession No. AAH69124.1 "interleukin 21 [*Homo sapiens*]," (2006).
GenBank Accession No. ABG36529.1 "interleukin-21 isoform [*Homo sapiens*]," (2007).
GenBank Accession No. NP_751915.1 "interleukin-15 isoform 2 preproprotein [*Homo sapiens*]," (2020).
GenBank Accession No. NP_000576.1 "interleukin-15 isoform 1 preproprotein [*Homo sapiens*]," (2020).
GenBank Accession No. AAI00963.1 "IL15 protein [*Homo sapiens*]," (2006).
GenBank Accession No. AAI00964.1 "Interleukin 15 [*Homo sapiens*]," (2006).
GenBank Accession No. AAI00962.1 "IL15 protein [*Homo sapiens*]," (2006).
GenBank Accession No. CAA71044.1 "interleukin-15 [*Homo sapiens*]," (1997).
GenBank Accession No. AAH18149.1 "interleukin 15 [*Homo sapiens*]," (2006).
GenBank Accession No. AAB97518.1 "interleukin 15 precursor [*Homo sapiens*]," (1998).
GenBank Accession No. CAA63914.1 "interleukin-15 (IL-15) [*Homo sapiens*]," (1996).
GenBank Accession No. CAA63913.1 "interleukin-15 (IL-15) [*Homo sapiens*]," (1996).
Hurton et al., "Tethered IL-15 augments antitumor activity and promotes a stem-cell memory subset in tumor-specific T cells," *Proc. Natl. Acad. Sci. USA*, 113(48): E7788-E7797 (2016).
"IL15 interleukin 15 [*Homo sapiens* (human)]," Gene ID: 3600, updated on Jul. 23, 2018; printed from www.ncbi.nlm.nih.gov/gene/3600.
"IL21 interleukin 21 [*Homo sapiens* (human)]," Gene ID: 59067, updated on Jul. 8, 2018; printed from www.ncbi.nlm.nih.gov/gene/59067.
Imamura et al., "Autonomous growth and increased cytotoxicity of natural killer cells expressing membrane-bound interleukin-15," *Blood*, 124(7): 1081-1088 (2014).
International Bureau, International Search Report and Written Opinion in International Application No. PCT/US2019/016975, mailed May 14, 2019.
Liu et al., "Systematic comparison of 2A peptides for cloning multi-genes in a polycistronic vector," *Sci. Rep.*, 7(1): 2193 (2017).
Paulick et al., "The Glycosylphosphatidylinositol Anchor: A Complex Membrane-Anchoring Structure for Proteins," *Biochemistry*, 47(27): 6991-7000 (2008).
Singh et al., "Reprogramming CD19-specific T cells with IL-21 signaling can improve adoptive immunotherapy of B-lineage malignancies," *Cancer Res.* 71(10): 3516-3527 (2011).
Zeng et al., "Synergy of IL-21 and IL-15 in regulating CD8+ T cell expansion and function," *J. Exp. Med.* 201(1): 139-148 (2005).

\* cited by examiner

| Signal sequence | IL-15 | Linker | Anchor |

FIG. 1A

| Signal sequence | IL-21 | Linker | Anchor |

FIG. 1B

| TeIL-21 | Linker | TeIL-15 |

FIG. 1C

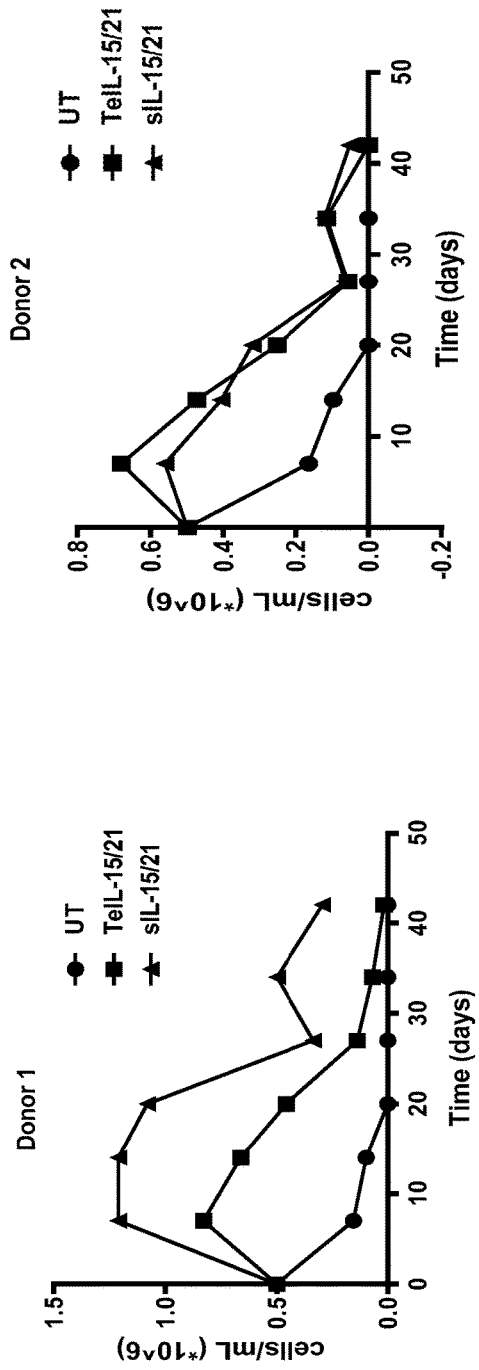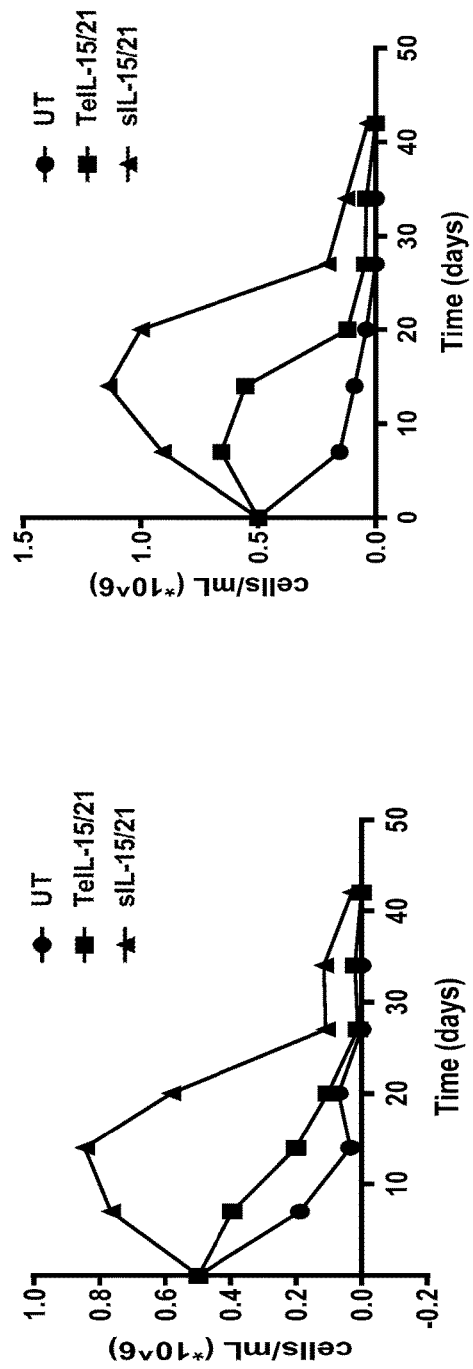
FIG. 5A
FIG. 5B
FIG. 5C
FIG. 5D

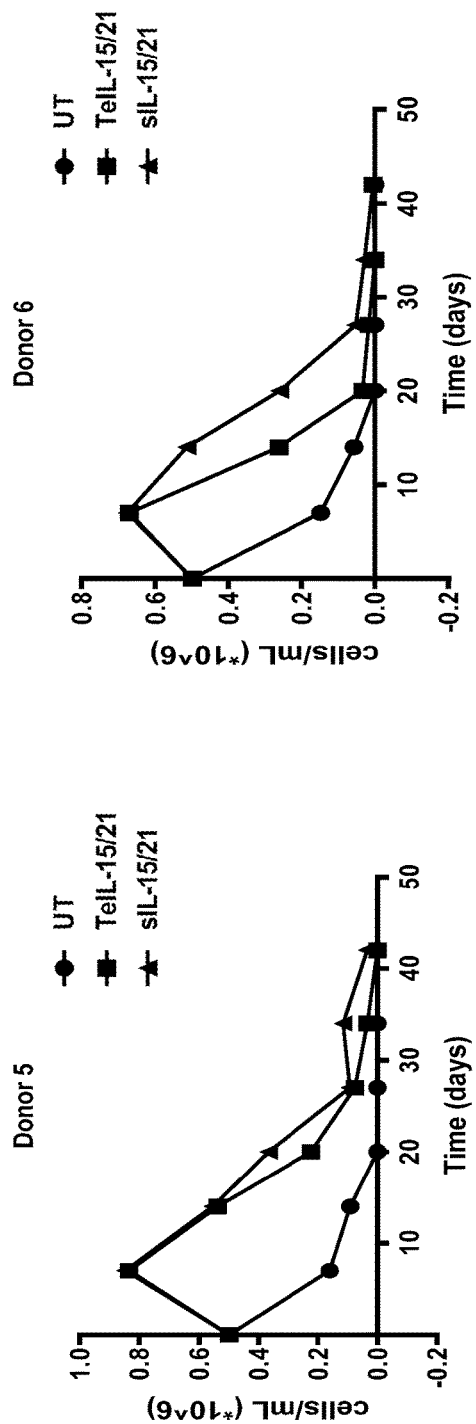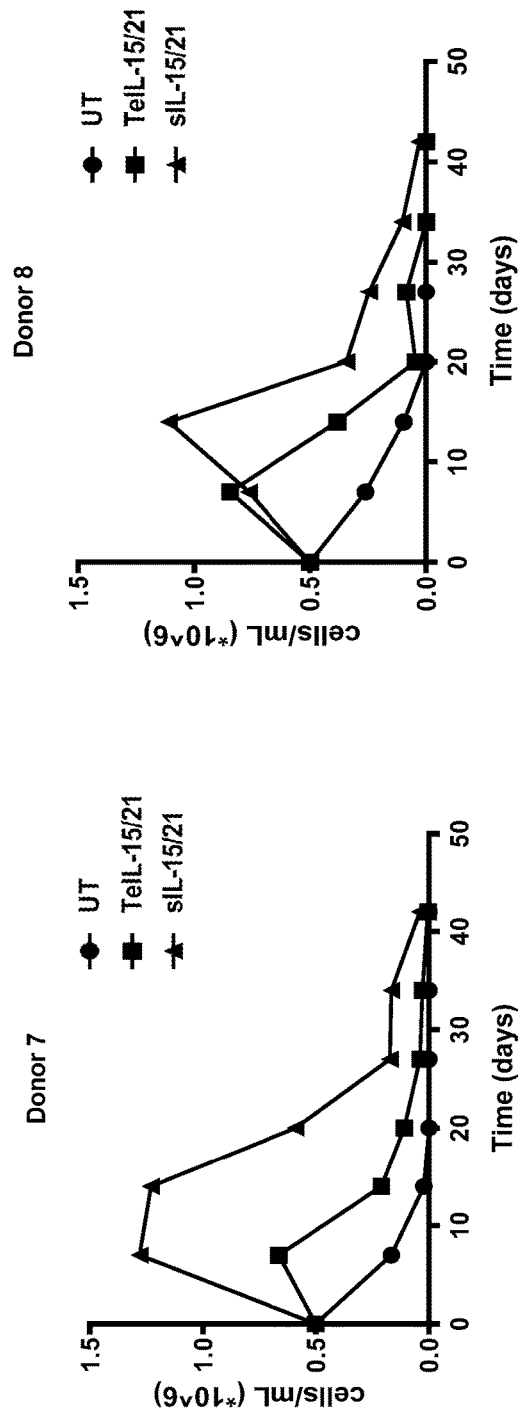
FIG. 5E
FIG. 5F
FIG. 5G
FIG. 5H

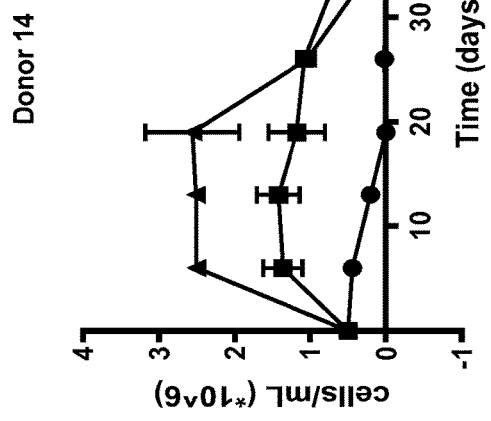
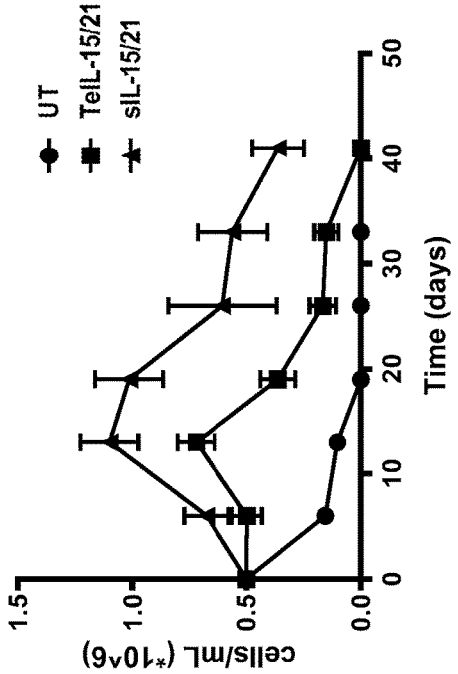
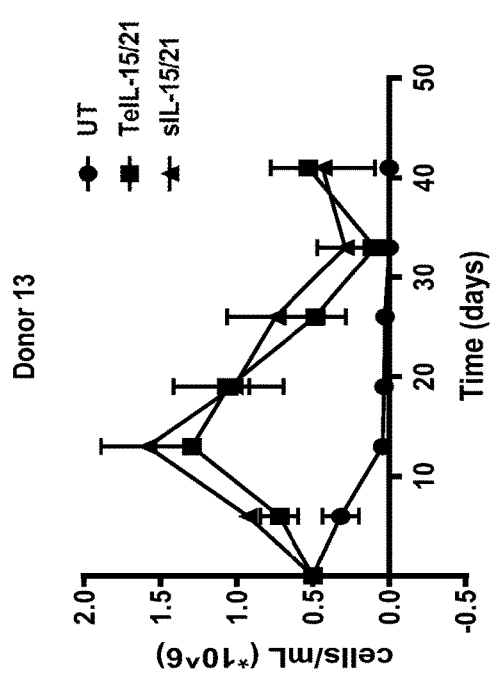
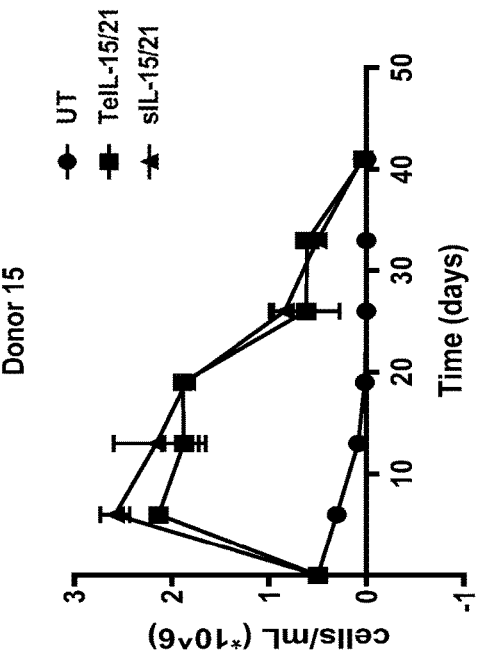
FIG. 5M
FIG. 5N
FIG. 5O
FIG. 5P

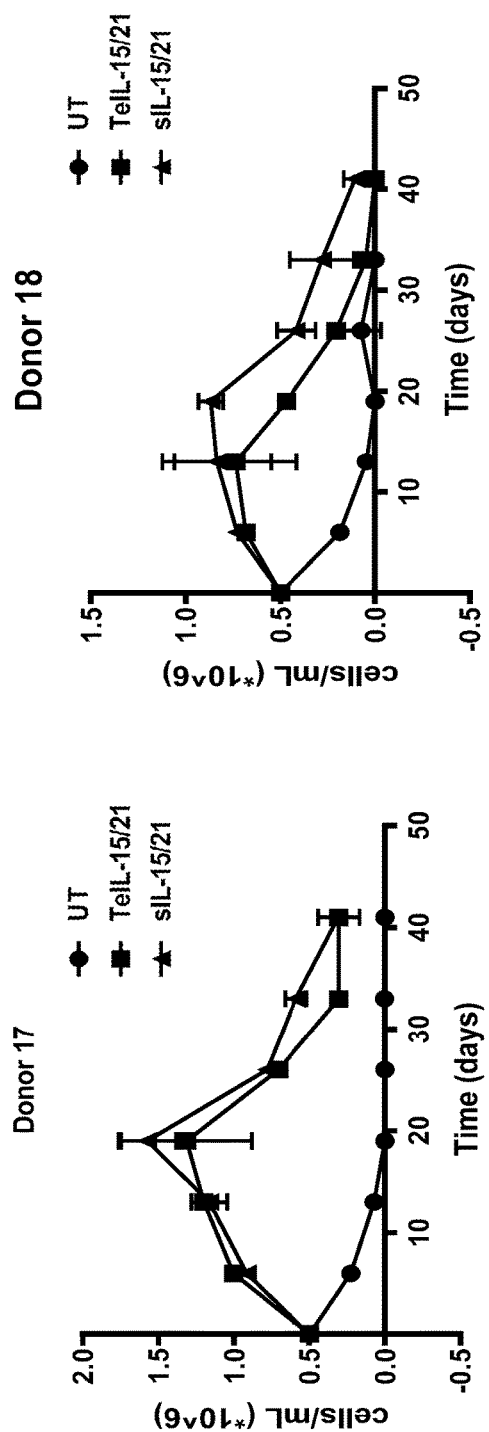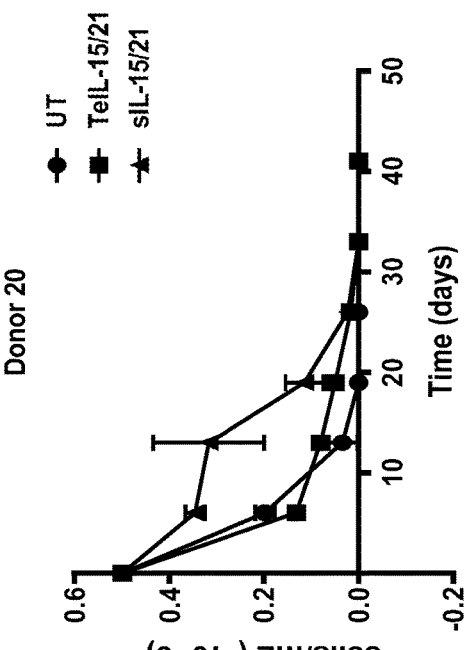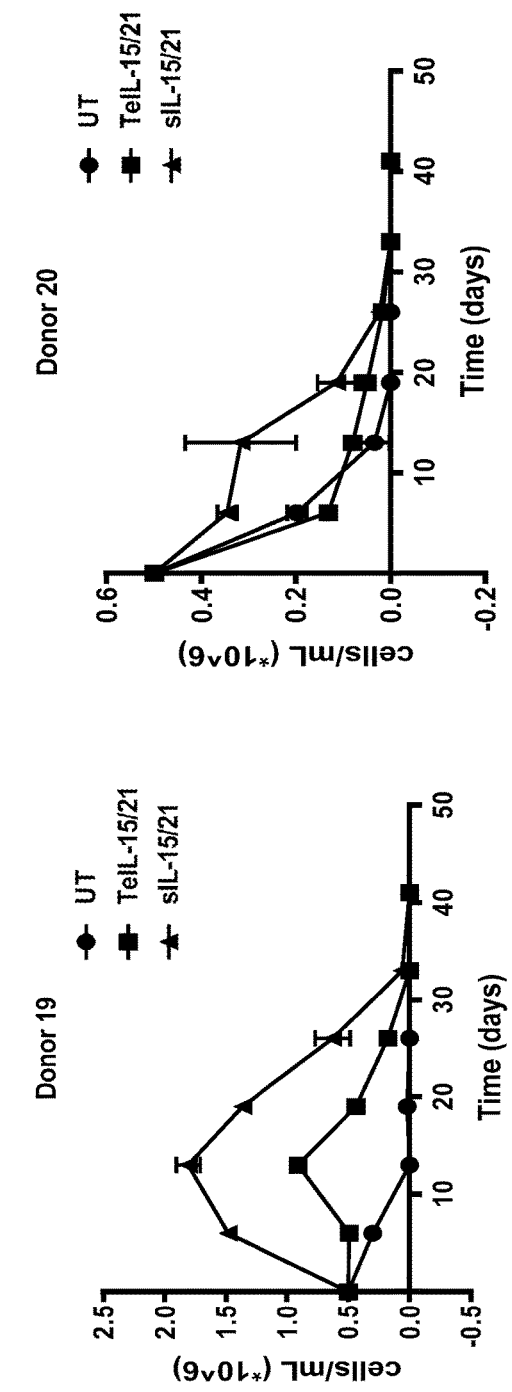
FIG. 5Q
FIG. 5R
FIG. 5S
FIG. 5T

SEQUENCE LISTING

```
Sequence total quantity: 44
SEQ ID NO: 1            moltype = AA  length = 18
FEATURE                 Location/Qualifiers
source                  1..18
                        mol_type = protein
                        organism = Homo sapiens
SEQUENCE: 1
MDWTWILFLV AAATRVHS                                                 18

SEQ ID NO: 2            moltype = AA  length = 133
FEATURE                 Location/Qualifiers
source                  1..133
                        mol_type = protein
                        organism = Homo sapiens
SEQUENCE: 2
QGQDRHMIRM RQLIDIVDQL KNYVNDLVPE FLPAPEDVET NCEWSAFSCF QKAQLKSANT   60
GNNERIINVS IKKLKRKPPS TNAGRRQKHR LTCPSCDSYE KKPPKEFLER FKSLLQKMIH  120
QHLSSRTHGS EDS                                                    133

SEQ ID NO: 3            moltype = AA  length = 114
FEATURE                 Location/Qualifiers
source                  1..114
                        mol_type = protein
                        organism = Homo sapiens
SEQUENCE: 3
NWVNVISDLK KIEDLIQSMH IDATLYTESD VHPSCKVTAM KCFLLELQVI SLESGDASIH   60
DTVENLIILA NNSLSSNGNV TESGCKECEE LEEKNIKEFL QSFVHIVQMF INTS        114

SEQ ID NO: 4            moltype = AA  length = 21
FEATURE                 Location/Qualifiers
```

```
source                  1..21
                        mol_type = protein
                        organism = Homo sapiens
SEQUENCE: 4
IYIWAPLAGT CGVLLLSLVI T                                                   21

SEQ ID NO: 5            moltype = AA  length = 46
FEATURE                 Location/Qualifiers
source                  1..46
                        mol_type = protein
                        organism = Homo sapiens
SEQUENCE: 5
LLPSWAITLI SVNGIFVICC LTYCFAPRCR ERRRNERLRR ESVRPV                         46

SEQ ID NO: 6            moltype = AA  length = 9
FEATURE                 Location/Qualifiers
VARIANT                 5
                        note = X is any naturally occurring amino acid residue.
source                  1..9
                        mol_type = protein
                        organism = Teschovirus A
SEQUENCE: 6
GDVEXNPGP                                                                  9

SEQ ID NO: 7            moltype = AA  length = 22
FEATURE                 Location/Qualifiers
source                  1..22
                        mol_type = protein
                        organism = Teschovirus A
SEQUENCE: 7
GSGATNFSLL KQAGDVEENP GP                                                  22

SEQ ID NO: 8            moltype = AA  length = 23
FEATURE                 Location/Qualifiers
source                  1..23
                        mol_type = protein
                        organism = Equine rhinitis A virus
SEQUENCE: 8
GSGQCTNYAL LKLAGDVESN PGP                                                 23

SEQ ID NO: 9            moltype = AA  length = 21
FEATURE                 Location/Qualifiers
source                  1..21
                        mol_type = protein
                        organism = Thosea asigna virus
SEQUENCE: 9
GSGEGRGSLL TCGDVEENPG P                                                   21

SEQ ID NO: 10           moltype =   length =
SEQUENCE: 10
000

SEQ ID NO: 11           moltype = AA  length = 27
FEATURE                 Location/Qualifiers
REGION                  1..27
                        note = synthetic
source                  1..27
                        mol_type = protein
                        organism = synthetic construct
SEQUENCE: 11
RAKRSGSGAT NFSLLKQAGD VEENPGP                                             27

SEQ ID NO: 12           moltype = AA  length = 27
FEATURE                 Location/Qualifiers
REGION                  1..27
                        note = synthetic
source                  1..27
                        mol_type = protein
                        organism = synthetic construct
SEQUENCE: 12
SGGGGSGGGG SGGGGSGGGG SGGGSLQ                                             27

SEQ ID NO: 13           moltype = AA  length = 18
FEATURE                 Location/Qualifiers
REGION                  1..18
                        note = synthetic
source                  1..18
                        mol_type = protein
                        organism = synthetic construct
```

```
SEQUENCE: 13
GSTSGSGKPG SGEGSTKG                                              18

SEQ ID NO: 14           moltype = AA  length = 45
FEATURE                 Location/Qualifiers
REGION                  1..45
                        note = synthetic
source                  1..45
                        mol_type = protein
                        organism = synthetic construct
SEQUENCE: 14
GGGGSGGGGS GGGGSGGGGS GGGGSGGGGS GGGGSGGGGS GGGGS                 45

SEQ ID NO: 15           moltype = AA  length = 46
FEATURE                 Location/Qualifiers
REGION                  1..46
                        note = synthetic
source                  1..46
                        mol_type = protein
                        organism = synthetic construct
SEQUENCE: 15
AEAAAKEAAA KEAAAKEAAA KALEAEAAAK EAAAKEAAAK EAAAKA               46

SEQ ID NO: 16           moltype = AA  length = 48
FEATURE                 Location/Qualifiers
REGION                  1..48
                        note = synthetic
source                  1..48
                        mol_type = protein
                        organism = synthetic construct
SEQUENCE: 16
SGGGGSGGGG SGGGGSGGGG SGGGGSGGGG SGGGGSGGGG SGGGGSLQ             48

SEQ ID NO: 17           moltype = AA  length = 61
FEATURE                 Location/Qualifiers
REGION                  1..61
                        note = synthetic
source                  1..61
                        mol_type = protein
                        organism = synthetic construct
SEQUENCE: 17
AGGGSGGGGS GGGGSGGGGS GGGGSGGGGS GGGGSGGGGS GGGSGGGGSA           60
S                                                                61

SEQ ID NO: 18           moltype = AA  length = 237
FEATURE                 Location/Qualifiers
REGION                  1..237
                        note = synthetic
source                  1..237
                        mol_type = protein
                        organism = synthetic construct
SEQUENCE: 18
ITCPPPMSVE HADIWVKSYS LYSRERYICN SGFKRKAGTS SLTECVLNKA TNVAHWTTPS 60
LKCIRDPALV HQRPAPPSTV TTAGVTPQPE SLSPSGKEPA ASSPSSNNTA ATTAAIVPGS 120
QLMPSKSPST GTTEISSHES SHGTPSQTTA KNWELTASAS HQPPGVYPQG HSDTTVAIST 180
STVLLCGLSA VSLLACYLKS RQTPPLASVE MEAMEALPVT WGTSSRDEDL ENCSHHL    237

SEQ ID NO: 19           moltype = AA  length = 180
FEATURE                 Location/Qualifiers
REGION                  1..180
                        note = synthetic
source                  1..180
                        mol_type = protein
                        organism = synthetic construct
SEQUENCE: 19
MDWTWILFLV AAATRVHSNW VNVISDLKKI EDLIQSMHID ATLYTESDVH PSCKVTAMKC 60
FLLELQVISL ESGDASIHDT VENLIILANN SLSSNGNVTE SGCKECEELE EKNIKEFLQS 120
FVHIVQMFIN TSSGGGGSGG GGSGGGGSGG GGSGGGSLQI YIWAPLAGTC GVLLLSLVIT 180

SEQ ID NO: 20           moltype = AA  length = 171
FEATURE                 Location/Qualifiers
REGION                  1..171
                        note = synthetic
source                  1..171
                        mol_type = protein
                        organism = synthetic construct
SEQUENCE: 20
MDWTWILFLV AAATRVHSNW VNVISDLKKI EDLIQSMHID ATLYTESDVH PSCKVTAMKC 60
FLLELQVISL ESGDASIHDT VENLIILANN SLSSNGNVTE SGCKECEELE EKNIKEFLQS 120
```

```
FVHIVQMFIN TSGSTSGSGK PGSGEGSTKG IYIWAPLAGT CGVLLLSLVI T         171

SEQ ID NO: 21            moltype = AA   length = 396
FEATURE                  Location/Qualifiers
REGION                   1..396
                         note = synthetic
source                   1..396
                         mol_type = protein
                         organism = synthetic construct
SEQUENCE: 21
MDWTWILFLV AAATRVHSNW VNVISDLKKI EDLIQSMHID ATLYTESDVH PSCKVTAMKC  60
FLLELQVISL ESGDASIHDT VENLIILANN SLSSNGNVTE SGCKECEELE EKNIKEFLQS 120
FVHIVQMFIN TSGGGGSGG GGSGGGGSGG GGSGGGGSLQI TCPPPMSVEH ADIWVKSYSL 180
YSRERYICNS GFKRKAGTSS LTECVLNKAT NVAHWTTPSL KCIRDPALVH QRPAPPSTVT 240
TAGVTPQPES LSPSGKEPAA SSPSSNNTAA TTAAIVPGSQ LMPSKSPSTG TTEISSHESS 300
HGTPSQTTAK NWELTASASH QPPGVYPQGH SDTTVAISTS TVLLCGLSAV SLLACYLKSR 360
QTPPLASVEM EAMEALPVTW GTSSRDEDLE NCSHHL                          396

SEQ ID NO: 22            moltype = AA   length = 198
FEATURE                  Location/Qualifiers
REGION                   1..198
                         note = synthetic
source                   1..198
                         mol_type = protein
                         organism = synthetic construct
SEQUENCE: 22
MDWTWILFLV AAATRVHSNW VNVISDLKKI EDLIQSMHID ATLYTESDVH PSCKVTAMKC  60
FLLELQVISL ESGDASIHDT VENLIILANN SLSSNGNVTE SGCKECEELE EKNIKEFLQS 120
FVHIVQMFIN TSGGGGSGGG GSGGGGSGGG GSGGGGSGGG GSGGGGSIYI           180
WAPLAGTCGV LLLSLVIT                                              198

SEQ ID NO: 23            moltype = AA   length = 132
FEATURE                  Location/Qualifiers
REGION                   1..132
                         note = synthetic
source                   1..132
                         mol_type = protein
                         organism = synthetic construct
SEQUENCE: 23
MDWTWILFLV AAATRVHSNW VNVISDLKKI EDLIQSMHID ATLYTESDVH PSCKVTAMKC  60
FLLELQVISL ESGDASIHDT VENLIILANN SLSSNGNVTE SGCKECEELE EKNIKEFLQS 120
FVHIVQMFIN TS                                                    132

SEQ ID NO: 24            moltype = AA   length = 199
FEATURE                  Location/Qualifiers
REGION                   1..199
                         note = synthetic
source                   1..199
                         mol_type = protein
                         organism = synthetic construct
SEQUENCE: 24
MDWTWILFLV AAATRVHSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK 120
PPKEFLERFK SLLQKMIHQH LSSRTHGSED SSGGGGSGGG GSGGGGSGGG GSGGGSLQIY 180
IWAPLAGTCG VLLLSLVIT                                             199

SEQ ID NO: 25            moltype = AA   length = 190
FEATURE                  Location/Qualifiers
REGION                   1..190
                         note = synthetic
source                   1..190
                         mol_type = protein
                         organism = synthetic construct
SEQUENCE: 25
MDWTWILFLV AAATRVHSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK 120
PPKEFLERFK SLLQKMIHQH LSSRTHGSED SGSTSGSGKP GSGEGSTKGI YIWAPLAGTC 180
GVLLLSLVIT                                                       190

SEQ ID NO: 26            moltype = AA   length = 217
FEATURE                  Location/Qualifiers
REGION                   1..217
                         note = synthetic
source                   1..217
                         mol_type = protein
                         organism = synthetic construct
SEQUENCE: 26
MDWTWILFLV AAATRVHSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK 120
```

```
PPKEFLERFK SLLQKMIHQH LSSRTHGSED SGGGGSGGGG SGGGGSGGGG SGGGGSGGGG    180
SGGGGSGGGG SGGGGSIYIW APLAGTCGVL LLSLVIT                             217

SEQ ID NO: 27              moltype = AA  length = 218
FEATURE                    Location/Qualifiers
REGION                     1..218
                           note = synthetic
source                     1..218
                           mol_type = protein
                           organism = synthetic construct
SEQUENCE: 27
MDWTWILFLV AAATRVHSQG QDRHMIRMRQ LIDIVDQLKN YVNDLVPEFL PAPEDVETNC     60
EWSAFSCFQK AQLKSANTGN NERIINVSIK KLKRKPPSTN AGRRQKHRLT CPSCDSYEKK    120
PPKEFLERFK SLLQKMIHQH LSSRTHGSED SAEAAAKEAA AKEAAAKEAA AKALEAEAAA    180
KEAAAKEAAA KEAAAKAIYI WAPLAGTCGV LLLSLVIT                            218

SEQ ID NO: 28              moltype = AA  length = 220
FEATURE                    Location/Qualifiers
REGION                     1..220
                           note = synthetic
source                     1..220
                           mol_type = protein
                           organism = synthetic construct
SEQUENCE: 28
MDWTWILFLV AAATRVHSQG QDRHMIRMRQ LIDIVDQLKN YVNDLVPEFL PAPEDVETNC     60
EWSAFSCFQK AQLKSANTGN NERIINVSIK KLKRKPPSTN AGRRQKHRLT CPSCDSYEKK    120
PPKEFLERFK SLLQKMIHQH LSSRTHGSED SSGGGGSGGG GSGGGGSGGG GSGGGGSGGG    180
GSGGGGSGGG GSGGGGSLQI YIWAPLAGTC GVLLLSLVIT                          220

SEQ ID NO: 29              moltype = AA  length = 233
FEATURE                    Location/Qualifiers
REGION                     1..233
                           note = synthetic
source                     1..233
                           mol_type = protein
                           organism = synthetic construct
SEQUENCE: 29
MDWTWILFLV AAATRVHSQG QDRHMIRMRQ LIDIVDQLKN YVNDLVPEFL PAPEDVETNC     60
EWSAFSCFQK AQLKSANTGN NERIINVSIK KLKRKPPSTN AGRRQKHRLT CPSCDSYEKK    120
PPKEFLERFK SLLQKMIHQH LSSRTHGSED SAGGGSGGGG SGGGGSGGGG SGGGGSGGGG    180
SGGGGSGGGG SGGGGSGGGS GGGGSGGGGS ASIYIWAPLA GTCGVLLLSL VIT           233

SEQ ID NO: 30              moltype = AA  length = 245
FEATURE                    Location/Qualifiers
REGION                     1..245
                           note = synthetic
source                     1..245
                           mol_type = protein
                           organism = synthetic construct
SEQUENCE: 30
MDWTWILFLV AAATRVHSQG QDRHMIRMRQ LIDIVDQLKN YVNDLVPEFL PAPEDVETNC     60
EWSAFSCFQK AQLKSANTGN NERIINVSIK KLKRKPPSTN AGRRQKHRLT CPSCDSYEKK    120
PPKEFLERFK SLLQKMIHQH LSSRTHGSED SSGGGGSGGG GSGGGGSGGG GSGGGGSGGG    180
GSGGGGSGGG GSGGGGSLQL LPSWAITLIS VNGIFVICCL TYCFAPRCRE RRRNERLRRE    240
SVRPV                                                                245

SEQ ID NO: 31              moltype = AA  length = 205
FEATURE                    Location/Qualifiers
REGION                     1..205
                           note = synthetic
source                     1..205
                           mol_type = protein
                           organism = synthetic construct
SEQUENCE: 31
MDWTWILFLV AAATRVHSNW VNVISDLKKI EDLIQSMHID ATLYTESDVH PSCKVTAMKC     60
FLLELQVISL ESGDASIHDT VENLIILANN SLSSNGNVTE SGCKECEELE EKNIKEFLQS    120
FVHIVQMFIN TSSGGGGSGG GGSGGGGSGG GGSGGGSLQL LPSWAITLIS VNGIFVICCL    180
TYCFAPRCRE RRRNERLRRE SVRPV                                          205

SEQ ID NO: 32              moltype = AA  length = 447
FEATURE                    Location/Qualifiers
REGION                     1..447
                           note = synthetic
source                     1..447
                           mol_type = protein
                           organism = synthetic construct
SEQUENCE: 32
MDWTWILFLV AAATRVHSQG QDRHMIRMRQ LIDIVDQLKN YVNDLVPEFL PAPEDVETNC     60
EWSAFSCFQK AQLKSANTGN NERIINVSIK KLKRKPPSTN AGRRQKHRLT CPSCDSYEKK    120
```

```
PPKEFLERFK SLLQKMIHQH LSSRTHGSED SSGGGGSGGG GSGGGGSGGG GSGGGGSGGG    180
GSGGGGSGGG GSGGGGSLQI YIWAPLAGTC GVLLLSLVIT GSGATNFSLL KQAGDVEENP    240
GPMDWTWILF LVAAATRVHS NWVNVISDLK KIEDLIQSMH IDATLYTESD VHPSCKVTAM    300
KCFLLELQVI SLESGDASIH DTVENLIILA NNSLSSNGNV TESGCKECEE LEEKNIKEFL    360
QSFVHIVQMF INTSSGGGGS GGGGSGGGGS GGGGSGGGSL QLLPSWAITL ISVNGIFVIC    420
CLTYCFAPRC RERRRNERLR RESVRPV                                       447

SEQ ID NO: 33           moltype = AA  length = 448
FEATURE                 Location/Qualifiers
REGION                  1..448
                        note = synthetic
source                  1..448
                        mol_type = protein
                        organism = synthetic construct
SEQUENCE: 33
MDWTWILFLV AAATRVHSQG QDRHMIRMRQ LIDIVDQLKN YVNDLVPEFL PAPEDVETNC     60
EWSAFSCFQK AQLKSANTGN NERIINVSIK KLKRKPPSTN AGRRQKHRLT CPSCDSYEKK    120
PPKEFLERFK SLLQKMIHQH LSSRTHGSED SSGGGGSGGG GSGGGGSGGG GSGGGGSGGG    180
GSGGGGSGGG GSGGGGSLQI YIWAPLAGTC GVLLLSLVIT GSGQCTNYAL LKLAGDVESN    240
PGPMDWTWIL FLVAAATRVH SNWVNVISDL KKIEDLIQSM HIDATLYTES DVHPSCKVTA    300
MKCFLLELQV ISLESGDASI HDTVENLIIL ANNSLSSNGN VTESGCKECE ELEEKNIKEF    360
LQSFVHIVQM FINTSGGGG SGGGGSGGGG SGGGGSGGGS LQLLPSWAIT LISVNGIFVI    420
CCLTYCFAPR CRERRRNERL RRESVRPV                                      448

SEQ ID NO: 34           moltype = AA  length = 446
FEATURE                 Location/Qualifiers
REGION                  1..446
                        note = synthetic
source                  1..446
                        mol_type = protein
                        organism = synthetic construct
SEQUENCE: 34
MDWTWILFLV AAATRVHSQG QDRHMIRMRQ LIDIVDQLKN YVNDLVPEFL PAPEDVETNC     60
EWSAFSCFQK AQLKSANTGN NERIINVSIK KLKRKPPSTN AGRRQKHRLT CPSCDSYEKK    120
PPKEFLERFK SLLQKMIHQH LSSRTHGSED SSGGGGSGGG GSGGGGSGGG GSGGGGSGGG    180
GSGGGGSGGG GSGGGGSLQI YIWAPLAGTC GVLLLSLVIT GSGEGRGSLL TCGDVEENPG    240
PMDWTWILFL VAAATRVHSN WVNVISDLKK IEDLIQSMHI DATLYTESDV HPSCKVTAMK    300
CFLLELQVIS LESGDASIHD TVENLIILAN NSLSSNGNVT ESGCKECEEL EEKNIKEFLQ    360
SFVHIVQMFI NTSSGGGGSG GGSGGGGSG GGGSGGGSL LLPSWAITLI SVNGIFVICC    420
LTYCFAPRCR ERRRNERLRR ESVRPV                                        446

SEQ ID NO: 35           moltype = AA  length = 452
FEATURE                 Location/Qualifiers
REGION                  1..452
                        note = synthetic
source                  1..452
                        mol_type = protein
                        organism = synthetic construct
SEQUENCE: 35
MDWTWILFLV AAATRVHSQG QDRHMIRMRQ LIDIVDQLKN YVNDLVPEFL PAPEDVETNC     60
EWSAFSCFQK AQLKSANTGN NERIINVSIK KLKRKPPSTN AGRRQKHRLT CPSCDSYEKK    120
PPKEFLERFK SLLQKMIHQH LSSRTHGSED SSGGGGSGGG GSGGGGSGGG GSGGGGSGGG    180
GSGGGGSGGG GSGGGGSLQI YIWAPLAGTC GVLLLSLVIT RAKRSGSGAT NFSLLKQAGD    240
VEENPGPMDW TWILFLVAAA TRVHSNWVNV ISDLKKIEDL IQSMHIDATL YTESDVHPSC    300
KVTAMKCFLL ELQVISLESG DASIHDTVEN LIILANNSLS SNGNVTESGC KECEELEEKN    360
IKEFLQSFVH IVQMFINTSS GGGGSGGGGS GGGGSGGGGS GGGSLQLLPS WAITLISVNG    420
IFVICCLTYC FAPRCRERRR NERLRRESVR PV                                 452

SEQ ID NO: 36           moltype = AA  length = 473
FEATURE                 Location/Qualifiers
REGION                  1..473
                        note = synthetic
source                  1..473
                        mol_type = protein
                        organism = synthetic construct
SEQUENCE: 36
MDWTWILFLV AAATRVHSQG QDRHMIRMRQ LIDIVDQLKN YVNDLVPEFL PAPEDVETNC     60
EWSAFSCFQK AQLKSANTGN NERIINVSIK KLKRKPPSTN AGRRQKHRLT CPSCDSYEKK    120
PPKEFLERFK SLLQKMIHQH LSSRTHGSED SSGGGGSGGG GSGGGGSGGG GSGGGGSGGG    180
GSGGGGSGGG GSGGGGSLQL LPSWAITLIS VNGIFVICCL TYCFAPRCRE RRRNERLRRE    240
SVRPVGSGQC TNYALLKLAG DVESNPGPMD WTWILFLVAA ATRVHSNWVN VISDLKKIED    300
LIQSMHIDAT LYTESDVHPS CKVTAMKCFL LELQVISLES GDASIHDTVE NLIILANNSL    360
SSNGNVTESG CKECEELEEK NIKEFLQSFV HIVQMFINTS SGGGGSGGGG SGGGGSGGGG    420
SGGGSLQLLP SWAITLISVN GIFVICCLTY CFAPRCRERR RNERLRRESV RPV          473

SEQ ID NO: 37           moltype = AA  length = 477
FEATURE                 Location/Qualifiers
REGION                  1..477
                        note = synthetic
```

```
source                    1..477
                          mol_type = protein
                          organism = synthetic construct
SEQUENCE: 37
MDWTWILFLV AAATRVHSQG QDRHMIRMRQ LIDIVDQLKN YVNDLVPEFL PAPEDVETNC    60
EWSAFSCFQK AQLKSANTGN NERIINVSIK KLKRKPPSTN AGRRQKHRLT CPSCDSYEKK   120
PPKEFLERFK SLLQKMIHQH LSSRTHGSED SSGGGGSGGG GSGGGGSGGG GSGGGGSGGG   180
GSGGGGSGGG GSGGGGSLQL LPSWAITLIS VNGIFVICCL TYCFAPRCRE RRRNERLRRE   240
SVRPVRAKRS GSGATNFSLL KQAGDVEENP GPMDWTWILF LVAAATRVHS NWVNVISDLK   300
KIEDLIQSMH IDATLYTESD VHPSCKVTAM KCFLLELQVI SLESGDASIH DTVENLIILA   360
NNSLSSNGNV TESGCKECEE LEEKNIKEFL QSFVHIVQMF INTSSGGGGS GGGGSGGGGS   420
GGGGSGGGSL QLLPSWAITL ISVNGIFVIC CLTYCFAPRC RERRRNERLR RESVRPV     477

SEQ ID NO: 38             moltype = AA   length = 27
FEATURE                   Location/Qualifiers
source                    1..27
                          mol_type = protein
                          organism = Homo sapiens
SEQUENCE: 38
NIKGSPWKGS LLLLLVSNLL LCQSVAP                                       27

SEQ ID NO: 39             moltype = DNA   length = 1341
FEATURE                   Location/Qualifiers
misc_feature              1..1341
                          note = synthetic
source                    1..1341
                          mol_type = other DNA
                          organism = synthetic construct
SEQUENCE: 39
atggattgga cctggattct gttcctggtg ccgctgcca caagagtgca tagccagggc     60
caagaccggc acatgatccg gatgagacag ctgatcgaca tcgtggacca gctgaagaac   120
tacgtgaacg acctggtgcc tgagttcctg cctgctcctg aggacgtgga aacaaattgc   180
gagtggtccg ccttcagctg cttccagaag gcccagctga aaagcgccaa caccggcaac   240
aacgagcgga tcatcaacgt gtccatcaag aagctgaagc ggaagcctcc tagcaccaat   300
gccggaagaa ggcagaagca cagactgacc tgtcctagct cgacagcta cgagaagaag   360
cctccaaaag agttcctgga acggttcaag agcctgctgc agaagatgat ccaccagcac   420
ctgagcagca gaacccacgg ctctgaagat tctagcggag cggaggaag tggtggcgga   480
ggttctggtg gcggtggatc aggcggtggc ggatctggcg gcgaggcag tggcggaggt   540
ggaagcggtg gtggtggctc tggcggaggc ggtagcggcg aggcggatc tcttcagatg   600
tatatttggg cccctctggc cggaacatgt ggcgtgttgc tgctgtctct ggttatcacc   660
ggcagcggcc ccacaaattt cagcctgctg aaacaggccg gcgacgtgga agagaatcct   720
ggacctatgg actggacttg gatactcttt ctggtcgctg ccgccacacg ggtgcactct   780
aattgtgtca acgtgatcag cgacctgaag aagatcgagg acctgatcca gagcatgcac   840
atcgacgcca cactgtacac cgagtccgat gtgcaccta gctgcaaagt gaccgccatg   900
aagtgctttc tgctggaact gcaagtgatc agcctggaaa gcggcgacgc cagcatccac   960
gataccgtgg aaaatctgat catcctggcc aacaacagcc tgtccagcaa cggcaatgtg  1020
accgagagcg gctgcaaaga gtgcgaggaa ctggaagaga agaacatcaa agagtttctg  1080
cagagcttcg tccacatcgt gcagatgttc atcaacacct catcaggcgg cggtggtagt  1140
ggaggcggag gctcaggcgg cggaggttcc ggaggtggcg gttccggcgg aggatctctt  1200
caattgctgc ctagctgggc catcacactg atctccgtga acggcatctt cgtgatctgc  1260
tgcctgacct actgcttcgc ccctagatgc agagagcgga agaaacga gcggctgaga  1320
agagaaagcg tgcggcctgt g                                            1341

SEQ ID NO: 40             moltype = DNA   length = 1344
FEATURE                   Location/Qualifiers
misc_feature              1..1344
                          note = synthetic
source                    1..1344
                          mol_type = other DNA
                          organism = synthetic construct
SEQUENCE: 40
atggattgga cctggattct gttcctggtg ccgctgcca caagagtgca tagccagggc     60
caagaccggc acatgatccg gatgagacag ctgatcgaca tcgtggacca gctgaagaac   120
tacgtgaacg acctggtgcc tgagttcctg cctgctcctg aggacgtgga aacaaattgc   180
gagtggtccg ccttcagctg cttccagaag gcccagctga aaagcgccaa caccggcaac   240
aacgagcgga tcatcaacgt gtccatcaag aagctgaagc ggaagcctcc tagcaccaat   300
gccggaagaa ggcagaagca cagactgacc tgtcctagct cgacagcta cgagaagaag   360
cctccaaaag agttcctgga acggttcaag agcctgctgc agaagatgat ccaccagcac   420
ctgagcagca gaacccacgg ctctgaagat tctagcggag cggaggaag tggtggcgga   480
ggttctggtg gcggtggatc aggcggtggc ggatctggcg gcgaggcag tggcggaggt   540
ggaagcggtg tggtggctc tggcggaggc ggtagcggcg aggcggatc tcttcagatc   600
tatatttggg cccctctggc cggaacatgt ggcgtgttgc tgctgtctct ggttatcacc   660
ggctccggcc agtgtaccaa ttcgccctg cttaaactgg ccggcgacgt ggaatccaat   720
cctggactgg actggatactc tttctggtcg ctgccgccac acggtgccc   780
tctaattggg tcaacgtgat cagcgacctg aagaagatcg aggacctgat ccagagcatg   840
cacatcgacg ccacactgta caccgagtcc gatgtgcacc ctagctgcaa agtgaccgcc   900
atgaagtgct ttctgctgga actgcaagtg atcagcctgg aaagcggcga cgccagcatc   960
cacgatacccg tggaaaatct gatcatcctg gccaacaaca gcctgtccag caacggcaat  1020
gtgaccgaga gcggctgcaa agagtgcgag gaactggaag agaagaacat caaagagttt  1080
```

```
ctgcagagct tcgtccacat cgtgcagatg ttcatcaaca cctcatcagg cggcggtggt   1140
agtggaggcg gaggctcagg cggcggaggt tccggaggtg gcggttccgg cggaggatct   1200
cttcaattgc tgcctagctg ggccatcaca ctgatctccg tgaacggcat cttcgtgatc   1260
tgctgcctga cctactgctt cgcccctaga tgcagagagc ggagaagaaa cgagcggctg   1320
agaagagaaa gcgtgcggcc tgtg                                          1344
```

SEQ ID NO: 41              moltype = DNA   length = 1338
FEATURE                    Location/Qualifiers
misc_feature               1..1338
                           note = synthetic
source                     1..1338
                           mol_type = other DNA
                           organism = synthetic construct
SEQUENCE: 41

```
atggattgga cctggattct gttcctggtg gccgctgcca caagagtgca tagccagggc   60
caagaccggc acatgatccg gatgagacag ctgatcgaca tcgtggacca gctgaagaac   120
tacgtgaacg acctggtgcc tgagttcctg cctgctcctg aggacgtgga aacaaattgc   180
gagtggtccg ccttcagctg cttccagaag gcccagctga aaagcgccaa caccggcaac   240
aacgagcgga tcatcaacgt gtccatcaag aagctgaagc ggaagcctcc tagcaccaat   300
gccgaagaa ggcagaagca cagactgacc tgtcctagct gcgacagcta cgagaagaag   360
cctccaaaag agttcctgga acggttcaag agcctgctgc agaagatgat ccaccagcac   420
ctgagcagca gaacccacgg ctctgaagat tctagcggag cggaggaag tggtggcgga   480
ggttctggtg gcggtggatc aggcggtggc ggatctggcg gcggaggcag tggcggaggt   540
ggaagcggtg gtggtggctc tggcggaggc ggtagcggcg gaggcggatc tcttcagatc   600
tatatttggg cccctctggc cggaacatgt ggcgtgttgc tgctgtctct ggttatcacc   660
ggttctgcg aaggcagagg ctctctgctt acttgtgaaga acgtggaaga gaatcctgga   720
cctatggact ggacttggat actctttctg gtcgctgccg ccacacgggt gcactctaat   780
tgggtcaacg tgatcagcga cctgaagaag atcgaggacc tgatccagag catgcacatc   840
gacgccacc tgtacaccga gtccgatgtg caccctagct gcaaagtgac cgccatgaag   900
tgcttttctg ctggaactgca agtgatcagc ctggaaaagc gcgacgccag catccacgat   960
accgtggaaa atctgatcat cctggccaac aacagcctgt ccagcaacgg caatgtgacc   1020
gagagcggct gcaaagagtg cgaggaactg aagagaagaa acatcaaaga gtttctgcag   1080
agcttcgtcc acatcgtgca gatgttcatc aacacctcat caggcggcgg tggtagtgga   1140
ggcggaggct caggcggcgg aggttccgga ggtggcggtt ccggcggagg atctcttcaa   1200
ttgctgccta gctgggccat cacactgatc tccgtgaacg gcatcttcgt gatctgctgc   1260
ctgacctact gcttcgcccc tagatgcaga gagcggagaa gaaacgagcg gctgagaaga   1320
gaaagcgtgc ggcctgtg                                                 1338
```

SEQ ID NO: 42              moltype = DNA   length = 1356
FEATURE                    Location/Qualifiers
misc_feature               1..1356
                           note = synthetic
source                     1..1356
                           mol_type = other DNA
                           organism = synthetic construct
SEQUENCE: 42

```
atggattgga cctggattct gttcctggtg gccgctgcca caagagtgca tagccagggc   60
caagaccggc acatgatccg gatgagacag ctgatcgaca tcgtggacca gctgaagaac   120
tacgtgaacg acctggtgcc tgagttcctg cctgctcctg aggacgtgga aacaaattgc   180
gagtggtccg ccttcagctg cttccagaag gcccagctga aaagcgccaa caccggcaac   240
aacgagcgga tcatcaacgt gtccatcaag aagctgaagc ggaagcctcc tagcaccaat   300
gccggaagaa ggcagaagca cagactgacc tgtcctagct gcgacagcta cgagaagaag   360
cctccaaaag agttcctgga acggttcaag agcctgctgc agaagatgat ccaccagcac   420
ctgagcagca gaacccacgg ctctgaagat tctagcggag cggaggaag tggtggcgga   480
ggttctggtg gcggtggatc aggcggtggc ggatctggcg gcggaggcag tggcggaggt   540
ggaagcggtg gtggtggctc tggcggaggc ggtagcggcg gaggcggatc tcttcagatc   600
tatatttggg cccctctggc cggaacatgt ggcgtgttgc tgctgtctct ggttatcacc   660
agggccaaaa gaagcggcag cggcgccaca aatttcagcc tgctgaaaca ggccggcgac   720
gtggaagaga tcctggacc tatggactgg acttggatac tctttctggt cgctgccgcc   780
acacgggtgc actctaattg gtcaacgtg atcagcgacc tgaagaagat cgaggacctg   840
atccagagca tgcacatcga cgccacactg tacaccgagt ccgatgtgca ccctagctgc   900
aaagtgaccg ccatgaagtg ctttctgctg gaactgcaag tgatcagcct ggaaagcggc   960
gacgccagca tccacgatac cgtggaaaat ctgatcatcc tggccaacaa cagcctgtcc   1020
agcaacggca atgtgaccga gagcggctgc aaagagtgcg aggaactgaa gagaagaaac   1080
atcaaagagt ttctgcagag cttcgtccac atcgtgcaga tgttcatcaa cacctcatca   1140
ggcggcggtg gtagtggagg cggaggctca ggcggcggag gttccggagg tggcggttcc   1200
ggcggaggat ctcttcaatt gctgcctagc tgggccatca cactgatctc cgtgaacggc   1260
atcttcgtga tctgctgcct gacctactgc ttcgccccta gatgcagaga gcggagaaga   1320
aacgagcggc tgagaagaga aagcgtgcgg cctgtg                             1356
```

SEQ ID NO: 43              moltype = DNA   length = 1419
FEATURE                    Location/Qualifiers
misc_feature               1..1419
                           note = synthetic
source                     1..1419
                           mol_type = other DNA
                           organism = synthetic construct
SEQUENCE: 43

```
atggattgga cctggattct gttcctggtg gccgctgcca caagagtgca tagccagggc   60
```

```
caagaccggc acatgatccg gatgagacag ctgatcgaca tcgtggacca gctgaagaac   120
tacgtgaacg acctggtgcc tgagttcctg cctgctcctg aggacgtgga aacaaattgc   180
gagtggtccg ccttcagctg cttccagaag gcccagctga aaagcgccaa caccggcaac   240
aacgagcgga tcatcaacgt gtccatcaag aagctgaagc ggaagcctcc tagcaccaat   300
gccggaagaa ggcagaagca cagactgacc tgtcctagct gcgacagcta cgagaagaag   360
cctccaaaag agttcctgga acggttcaag agcctgctgc agaagatgat ccaccagcac   420
ctgagcagca gaacccacgg ctctgaagat tctagcggag gcggaggaag tggtggcgga   480
ggttctggtg gcggtggatc aggcggtggc ggatctggcg gcggaggcag tggcggaggt   540
ggaagcggtg gtggtggctc tggcggaggc ggtagcggcg gaggcggatc tcttcaattg   600
ctgcctagct gggccatcac actgatctcc gtgaacggca tcttcgtgat ctgctgcctg   660
acctactgct tcgcccctag atgcagagag cggagaagaa acgagcggct gagaagagaa   720
tctgtgcggc ctgttggctc cggccagtgt acaaattatg ccctgctgaa gctggccggc   780
gacgtggaat ctaatcctgg acctatggac tggacttgga tactctttct ggtcgctgcc   840
gccacacggg tgcactctaa ttgggtcaac gtgatcagca acctgaagaa gatcgaggac   900
ctgatccaga gcatgcacat cgacgccaca ctgtacaccg agtccgatgt gcaccctagc   960
tgcaaagtga ccgccatgaa gtgctttctg ctggaactgc aagtgatcag cctggaaagc  1020
ggcgacgcca gcatccacga taccgtgaaa aatctgatca tcctgccaa caacagcctg  1080
tccagcaacg gcaatgtgac cgagagcggc tgcaaagagt gcgaggaact ggaagaaaag  1140
aacatcaaag agtttctgca gagcttcgtc cacatcgtgc agatgttcat caacacctca  1200
tcaggtggcg gtggaagcgg aggtggcggt agtggcggcg gaggctcagg cggcggaggt  1260
tccggcggag gatctcttca gctcctgcca tcttgggcta tcaccctgat tagtgtgaat  1320
gggatctttg tcatctgttg tctcacgtac tgtttcgctc cccggtgcag agagagaagg  1380
cgcaacgaaa gactgcggag agaaagcgtc agacccgtg                          1419

SEQ ID NO: 44          moltype = DNA  length = 1431
FEATURE                Location/Qualifiers
misc_feature           1..1431
                       note = synthetic
source                 1..1431
                       mol_type = other DNA
                       organism = synthetic construct
SEQUENCE: 44
atggattgga cctggattct gttcctggtg gccgctgcca caagagtgca tagccagggc    60
caagaccggc acatgatccg gatgagacag ctgatcgaca tcgtggacca gctgaagaac   120
tacgtgaacg acctggtgcc tgagttcctg cctgctcctg aggacgtgga aacaaattgc   180
gagtggtccg ccttcagctg cttccagaag gcccagctga aaagcgccaa caccggcaac   240
aacgagcgga tcatcaacgt gtccatcaag aagctgaagc ggaagcctcc tagcaccaat   300
gccggaagaa ggcagaagca cagactgacc tgtcctagct gcgacagcta cgagaagaag   360
cctccaaaag agttcctgga acggttcaag agcctgctgc agaagatgat ccaccagcac   420
ctgagcagca gaacccacgg ctctgaagat tctagcggag gcggaggaag tggtggcgga   480
ggttctggtg gcggtggatc aggcggtggc ggatctggcg gcggaggcag tggcggaggt   540
ggaagcggtg gtggtggctc tggcggaggc ggtagcggcg gaggcggatc tcttcaattg   600
ctgcctagct gggccatcac actgatctcc gtgaacggca tcttcgtgat ctgctgcctg   660
acctactgct tcgcccctag atgcagagag cggagaagaa acgagcggct gagaagagaa   720
tctgtgcggc ctgttagagc caagagatct ggaagcggcg ccaccaactt tagcctgctg   780
aaacaggctg gcgacgtgga agagaaccct ggacctatgg actggacttg gatactcttt   840
ctggtcgctg ccgccacacg ggtgcactct aattgggtca acgtgatcag cgacctgaag   900
aagatcgagg acctgatcca gagcatgcac atcgacgcca cactgtacac cgagtccgat   960
gtgcacccta gctgcaaagt gaccgccatg aagtgctttc tgctggaact gcaagtgatc  1020
agcctggaaa gcggcgacgc cagcatccac gataccgtg aaaatctgat catcctggcc  1080
aacaacagcc tgtccagcaa cggcaatgtg accgagagcg gctgcaaaga gtgcgaggaa  1140
ctggaagaaa agaacatcaa agagtttctg cagagcttcg tccacatcgt gcagatgttc  1200
atcaacacct catcaggtgg cggtggaagc ggaggtggcg gtagtggcgg cggaggctca  1260
ggcggcggag gttccggcgg aggatctctt cagctcctgc catcttgggc tatcaccctg  1320
attagtgtga atgggatctt tgtcatctgt tgtctcacgt actgtttcgc tccccggtgc  1380
agagagagaa ggcgcaacga aagactgcgg agagaaagcg tcagacccgt g            1431
```

TETHERED INTERLEUKIN-15 AND INTERLEUKIN-21

CROSS-REFERENCE TO RELATED APPLICATIONS

This patent application is a continuation of U.S. patent application Ser. No. 16/964,796, filed Jul. 24, 2020, which is the U.S. national stage of PCT/US2019/016975, filed Feb. 7, 2019, which claims the benefit of U.S. Provisional Patent Application No. 62/628,454, filed Feb. 9, 2018, each of which is incorporated by reference in its entirety herein.

STATEMENT REGARDING FEDERALLY SPONSORED RESEARCH AND DEVELOPMENT

This invention was made with Government support under Grant Numbers ZIABC011478 awarded by the National Institutes of Health, National Cancer Institute. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 65,446 Byte file named "767321.xml," dated May 2, 2023.

BACKGROUND OF THE INVENTION

Adoptive cell therapy can be an effective treatment for cancer in some patients. However, obstacles to the overall success of adoptive cell therapy still exist. For example, the in vivo persistence, survival, and anti-tumor activity of the transferred T cells can, in some cases, decrease following adoptive transfer. Despite considerable research in the field of adoptive cell therapy, there still exists a need for improved methods and products for producing cells for adoptive cell therapy and treating and/or preventing cancer.

BRIEF SUMMARY OF THE INVENTION

An embodiment of the invention provides a nucleic acid comprising a nucleotide sequence encoding an amino acid sequence of Formula I:

$$S^1\text{-}N^1\text{-}L^1\text{-}C^1_a\text{-}L^2\text{-}S^2\text{-}N^2\text{-}L^3\text{-}C^2_b \quad \text{(Formula I)},$$

wherein:
each of $S^1$ and $S^2$ is, independently, a signal sequence;
one of $N^1$ and $N^2$ is an interleukin (IL)-21 amino acid sequence and one of $N^1$ and $N^2$ is an IL-15 amino acid sequence;
each of $L^1$, $L^2$, and $L^3$ is, independently, a linker sequence;
each of $C^1$ and $C^2$ is, independently, a transmembrane-intracellular amino acid sequence or a transmembrane amino acid sequence; and
each of a and b is, independently, 0 or 1.

Further embodiments of the invention provide related recombinant expression vectors, polypeptides, host cells, populations of cells, pharmaceutical compositions, and methods of treating or preventing cancer.

BRIEF DESCRIPTION OF THE SEVERAL VIEWS OF THE DRAWING(S)

FIG. 1A is a schematic illustrating the composition of a tethered IL-15 (TeIL-15) construct. Each TeIL-15 construct includes a signal sequence, IL-15 mature amino acid sequence, linker, and cell membrane anchor moiety ("anchor").

FIG. 1B is a schematic illustrating the composition of a tethered IL-21 (TeIL-21) construct. Each TeIL-21 construct includes a signal sequence, IL-21 mature amino acid sequence, linker, and cell membrane anchor moiety ("anchor").

FIG. 1C is a schematic illustrating the composition of tethered IL-21/tethered IL-15 (TeIL-21/15) construct. Each TeIL-21/15 construct includes a TeIL-21 construct of FIG. 1B, a cleavable linker, and a TeIL-15 construct of FIG. 1A.

Figure 2:
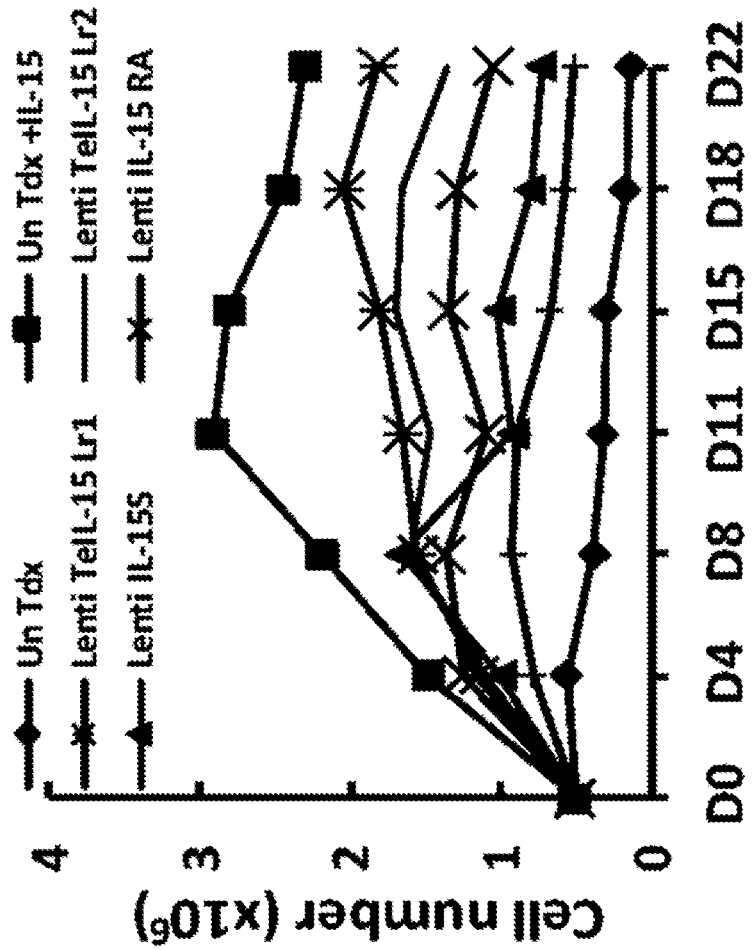

FIG. 2 is a graph showing the number of live cells measured at various time points (days) after IL-2 was withdrawn from the media seven days after transduction of the cells with a vector encoding the TeIL-15 Lr1, TeIL-15 Lr2, IL-15 RA, TeIL-15 Lr6, or IL-15S construct of Table 2. Untransduced (Un Tdx) cells served as a negative control. Untransduced cells cultured in the presence of exogenous IL-15 served as a positive control.

Figure 3:
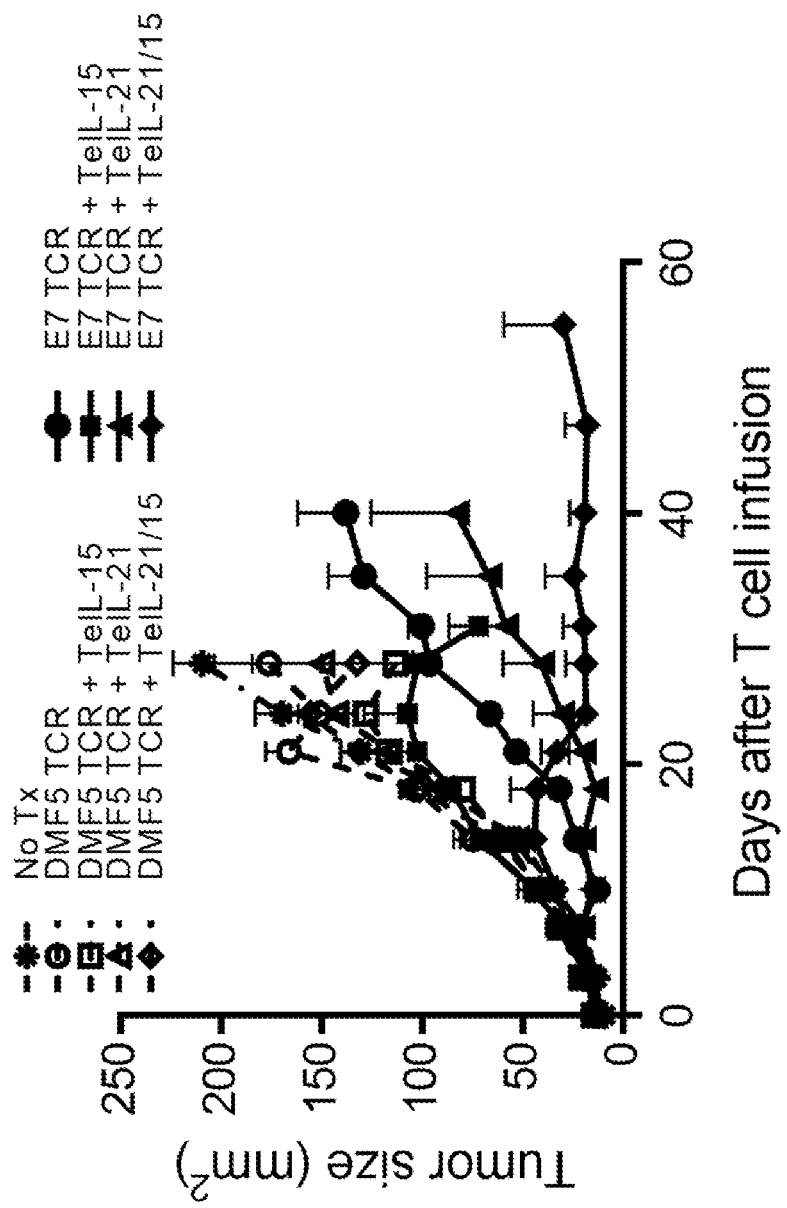

FIG. 3 is a graph showing the tumor size (mm²) measured in tumor-bearing mice on the indicated number of days after infusion of untransduced (*) or transduced cells (n=5 in each group). Cells were transduced with (i) DMF5 TCR and TeIL-15 Lr1Ar2 (open squares), (ii) DMF5 TCR and TeIL-21 Lr8Ar1 (open triangles), (iii) DMF5 TCR and TeIL-21/15 E2AAr1 (open diamonds), (iv) E7 TCR and TeIL-15 Lr1Ar2 (closed squares), (v) E7 TCR and TeIL-21 Lr8Ar1 (closed triangles), (vi) E7 TCR and TeIL-21/15 E2A Ar1 (closed diamonds), (vi) DMF5 TCR alone (open circles), or (vii) E7 TCR alone (closed circles).

Figure 4B:
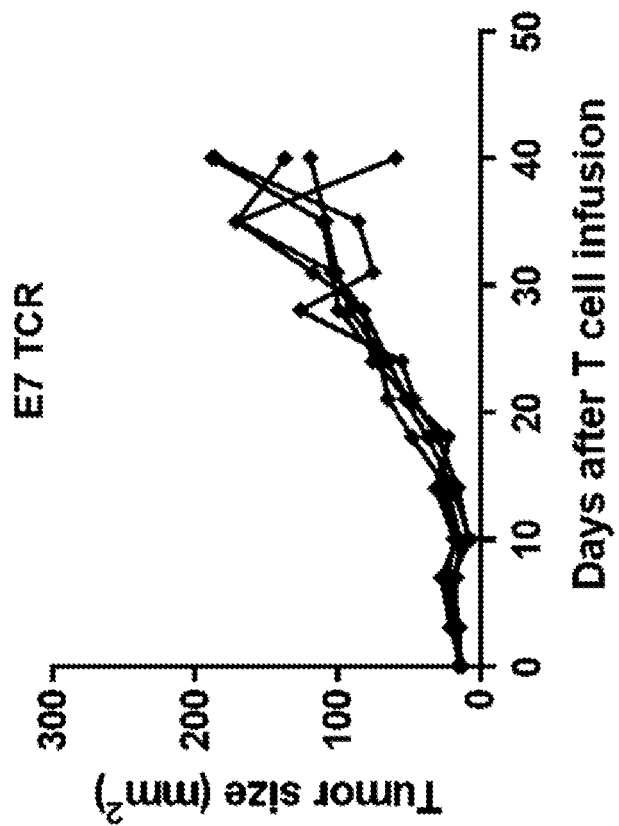
Figure 4A:
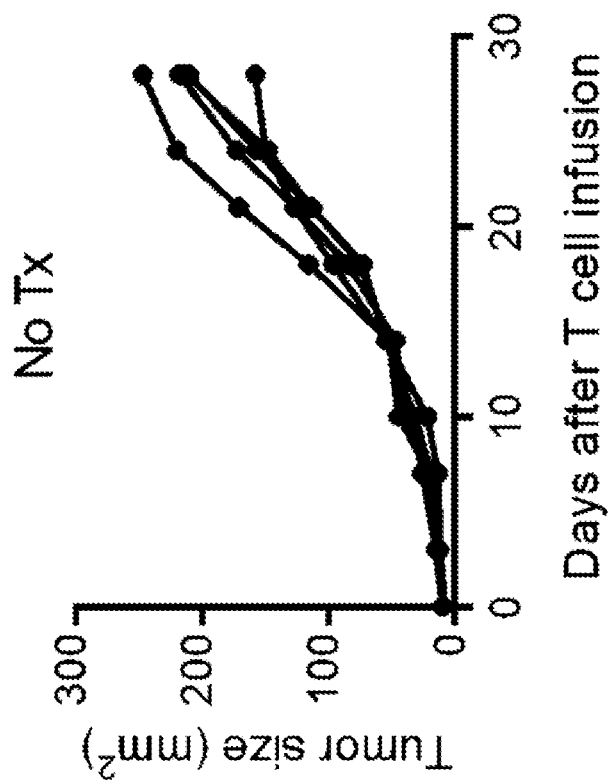

FIG. 4A is a graph showing the tumor size (mm²) measured in each of five tumor-bearing mice on the indicated number of days after infusion of untransduced T cells.

FIG. 4B is a graph showing the tumor size (mm²) measured in each of five tumor-bearing mice on the indicated number of days after infusion of T cells transduced with the E7 TCR alone.

Figures 4C, 4D:
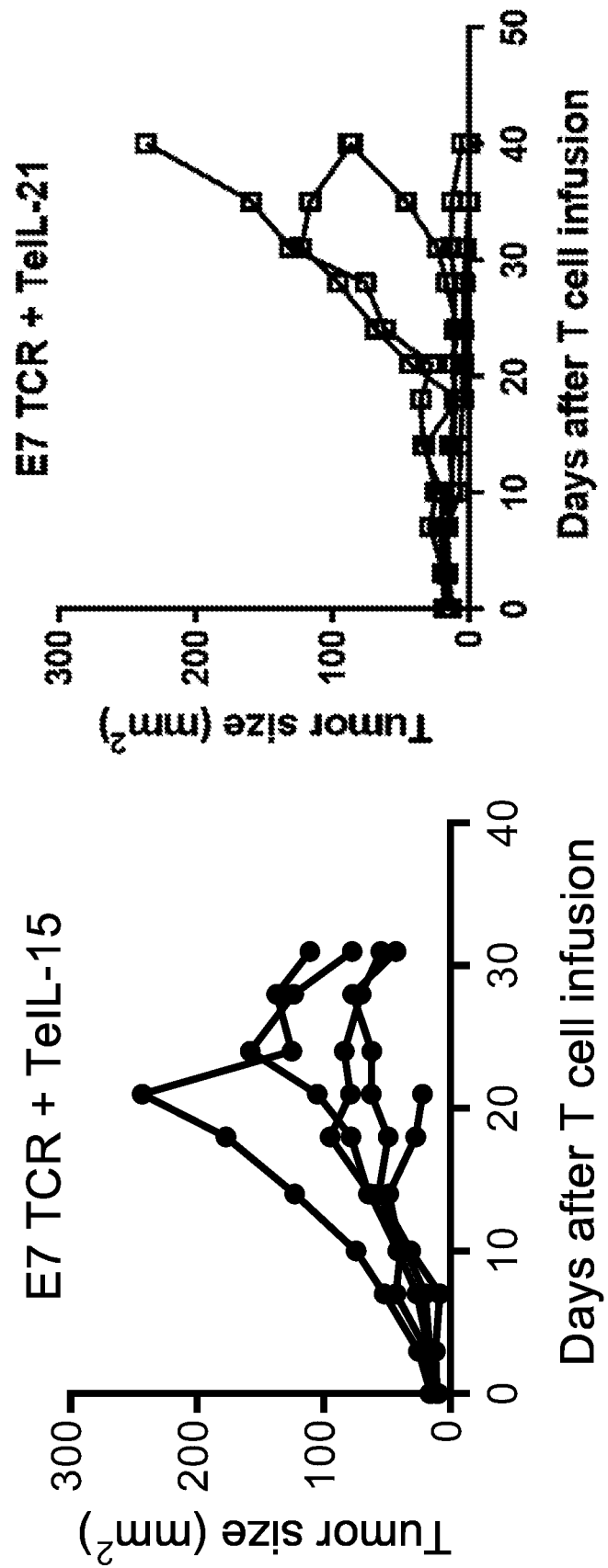

FIG. 4C is a graph showing the tumor size (mm²) measured in each of five tumor-bearing mice on the indicated number of days after infusion of T cells transduced with the E7 TCR and TeIL-15.

FIG. 4D is a graph showing the tumor size (mm²) measured in each of five tumor-bearing mice on the indicated number of days after infusion of T cells transduced with the E7 TCR and TeIL-21.

Figure 4F:
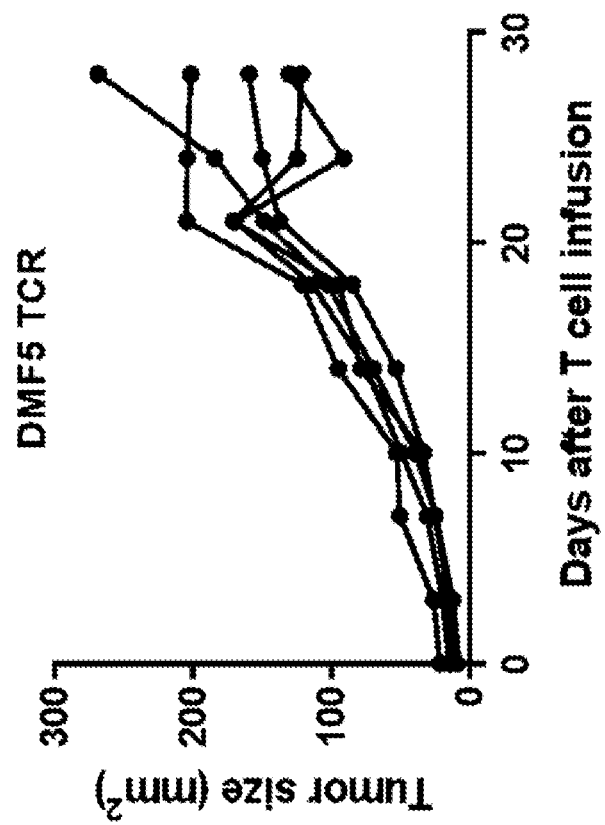
Figure 4E:
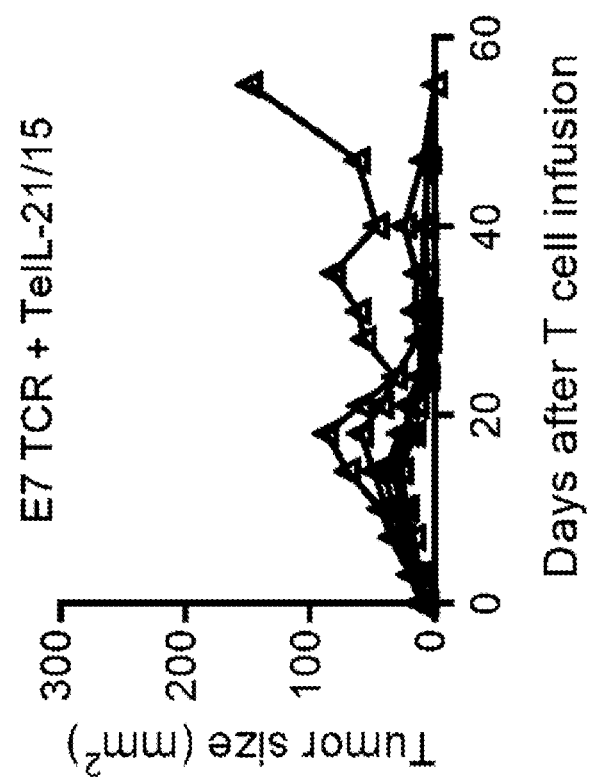

FIG. 4E is a graph showing the tumor size (mm²) measured in each of five tumor-bearing mice on the indicated number of days after infusion of T cells transduced with the E7 TCR and TeIL-21/15.

FIG. 4F is a graph showing the tumor size (mm²) measured in each of five tumor-bearing mice on the indicated number of days after infusion of T cells transduced with the DMF5 TCR alone.

Figure 4H:
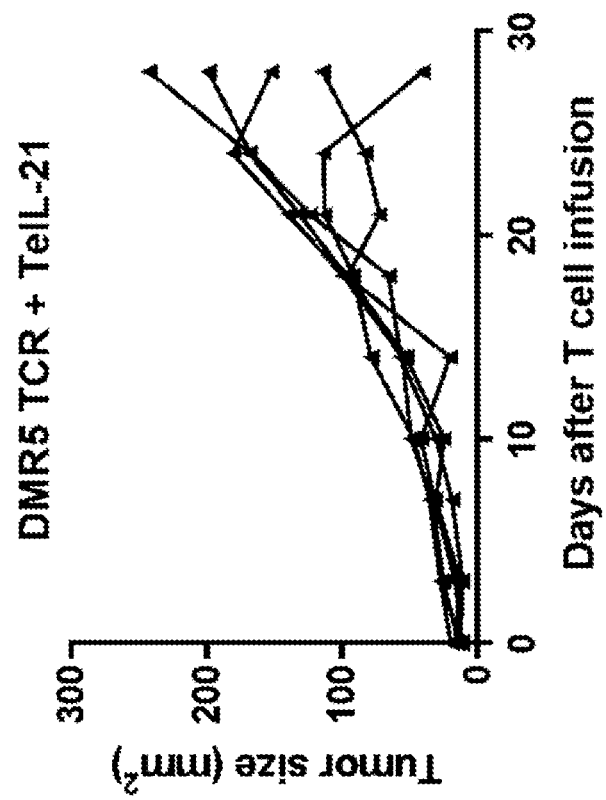
Figure 4G:
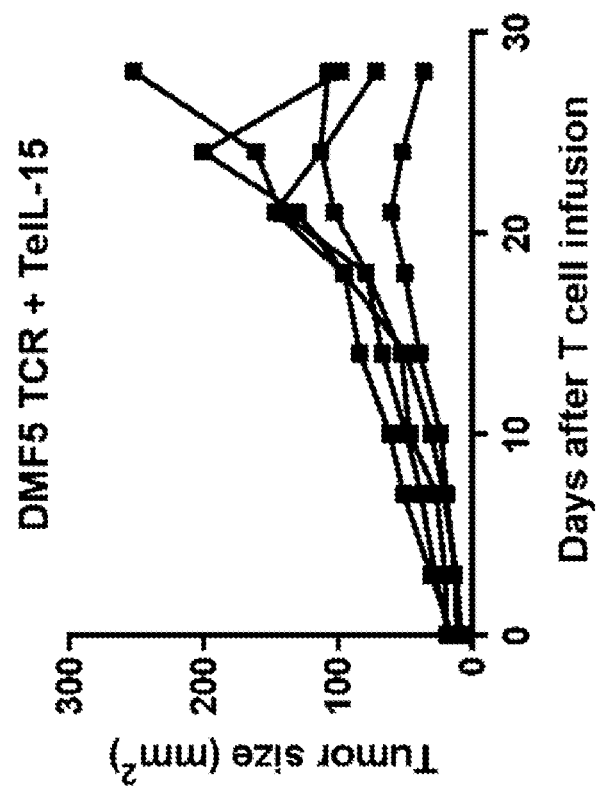

FIG. 4G is a graph showing the tumor size (mm²) measured in each of five tumor-bearing mice on the indicated number of days after infusion of T cells transduced with the DMF5 TCR and TeIL-15.

FIG. 4H is a graph showing the tumor size (mm2) measured in each of five tumor-bearing mice on the indicated number of days after infusion of T cells transduced with the DMF5 TCR and TeIL-21.

Figure 4I:
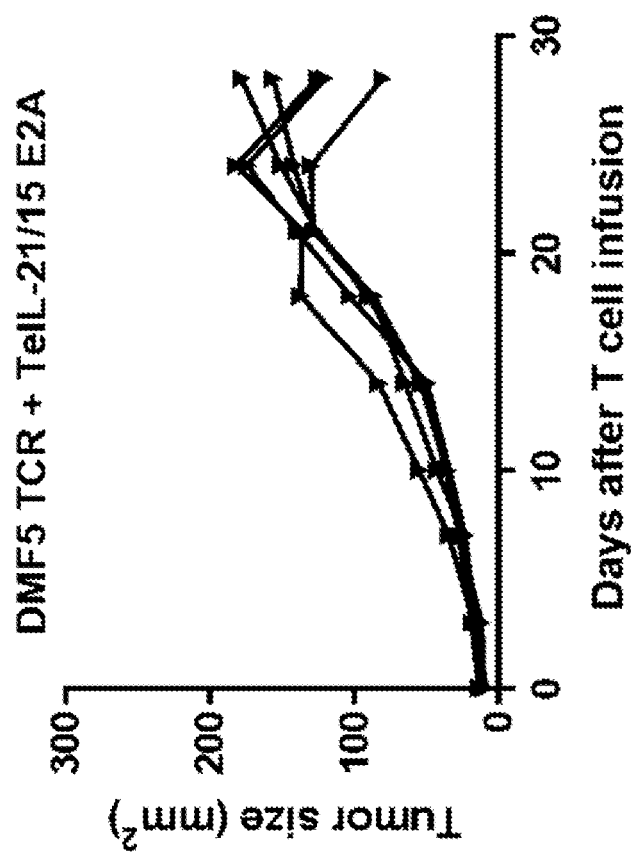

FIG. 4I is a graph showing the tumor size (mm²) measured in each of five tumor-bearing mice on the indicated number of days after infusion of T cells transduced with the DMF5 TCR and TeIL-21/15.

Figure 5I:
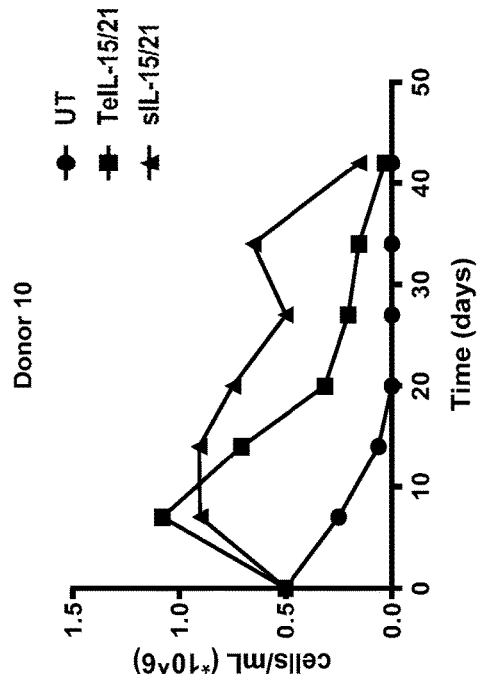
Figure 5J:
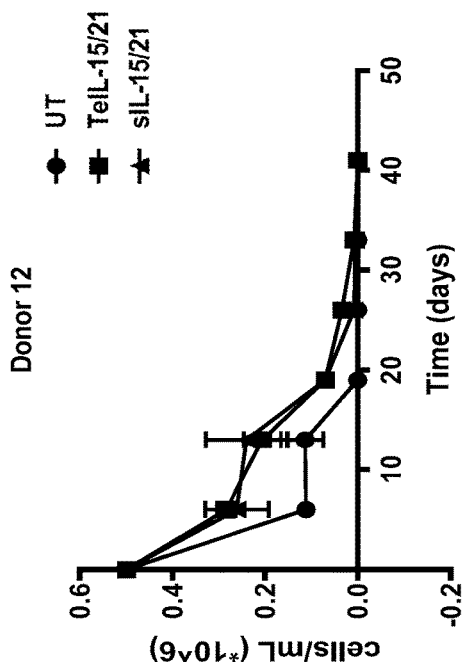
Figure 5K:
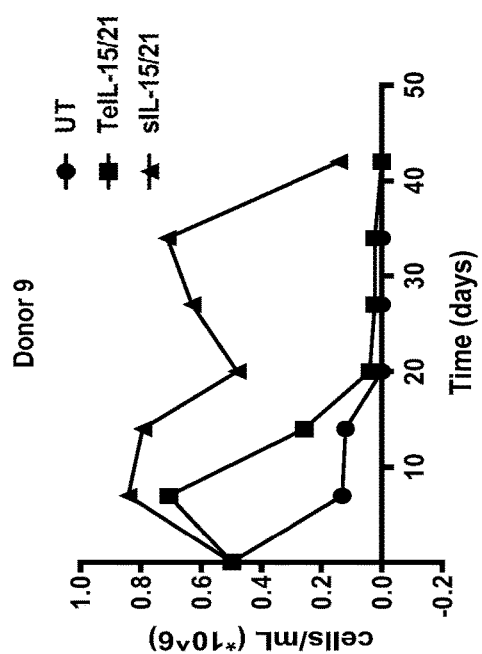
Figure 5L:
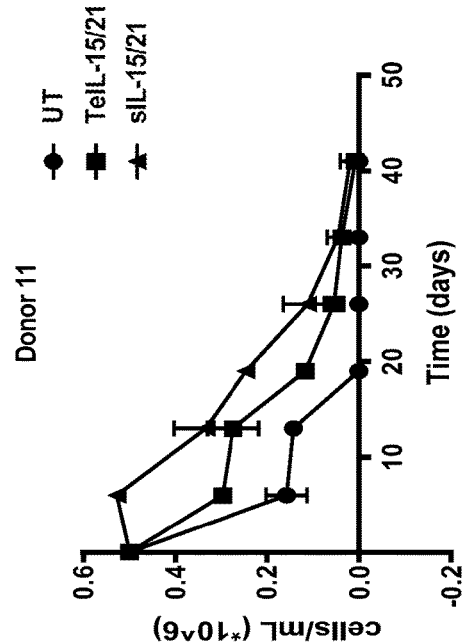

FIGS. 5A-5T are graphs showing the concentration (number of cells per mL×10⁶) of cells living at the indicated time points (days) following transduction of cells from healthy donors 1-20 (FIGS. 5A-5T, respectively) with TeIL-21/15 FurinA-P2A Ar2 (squares) or secreted IL-21/15 (sIL-21/15) (triangles). Untreated (UT) cells (circles) served as a control.

Figure 6B:
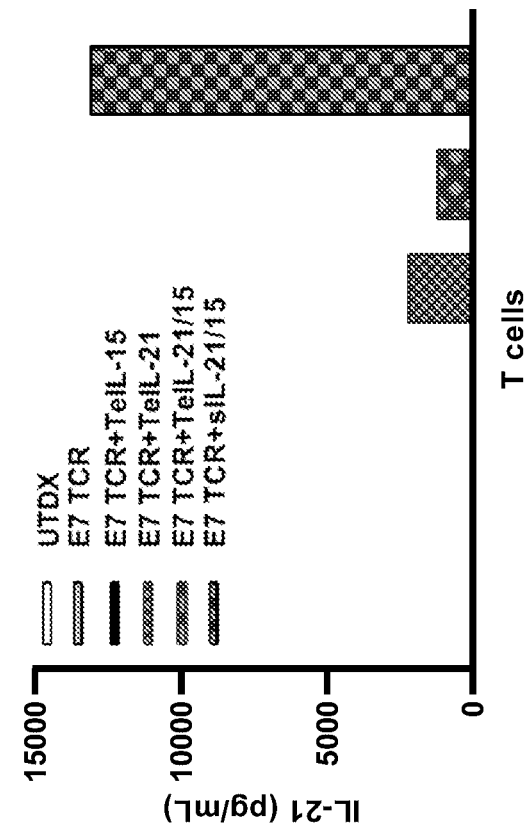
Figure 6A:
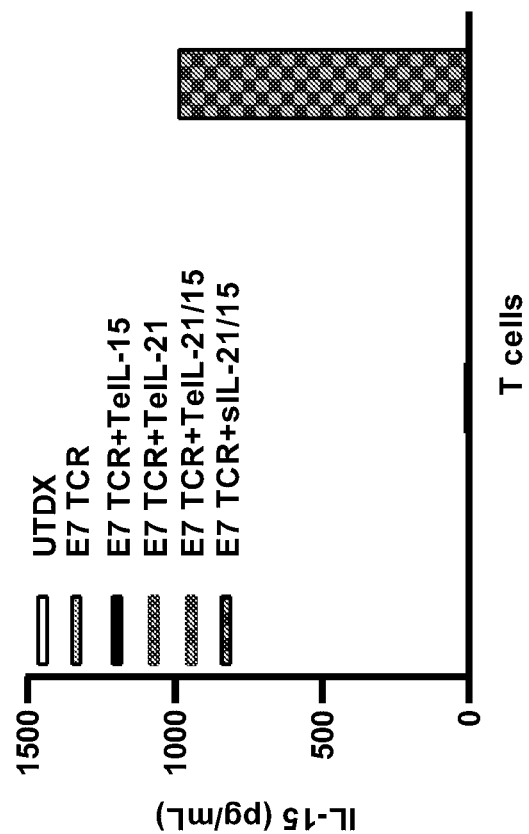

FIGS. 6A-6B are graphs showing the concentration (pg/mL) of IL-15 (6A) and IL-21 (6B) measured in the supernatants of T cells transduced with one of (i)-(v), as follows: (i) E7 TCR and TeIL-15 Lr1Ar2, (ii) E7 TCR and TeIL-21 Lr8Ar2, (iii) E7 TCR and TeIL-21/15 FurinA-P2A Ar2, (iv) E7 TCR and secreted IL-21/15 (sIL-21/15), or (v) E7 TCR alone. Untransduced (UTDX) T cells served as a control.

Figure 6D:
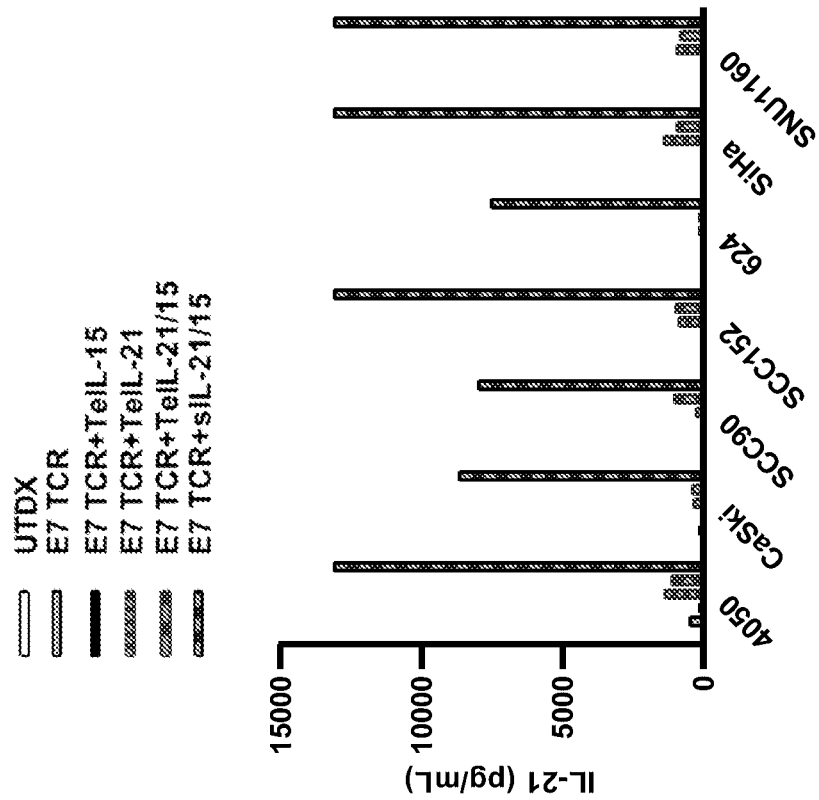
Figure 6C:
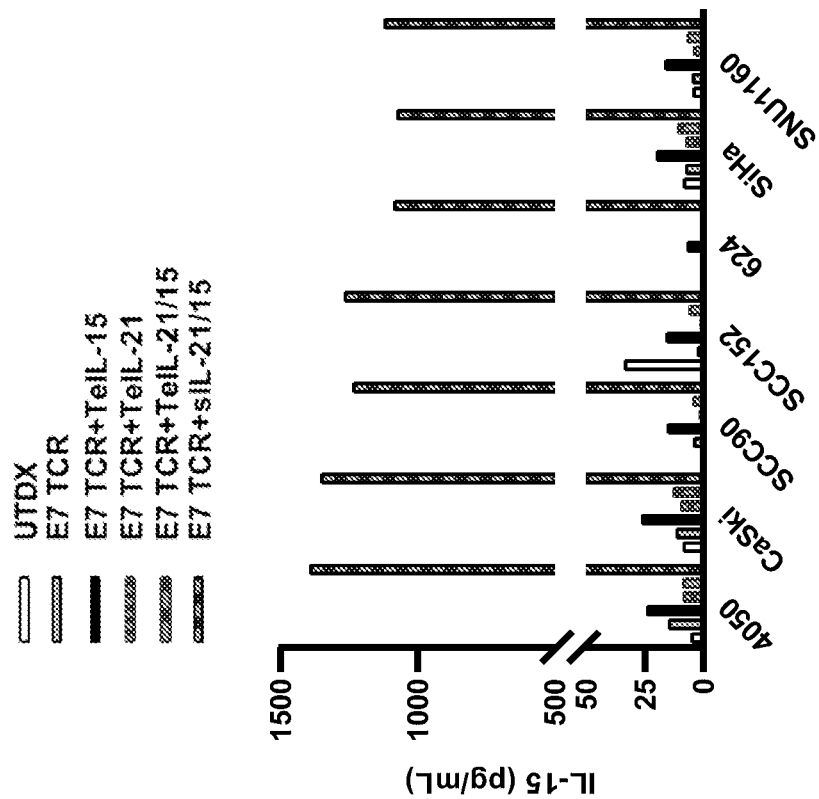

FIGS. 6C-6D are graphs showing the concentration (pg/mL) of IL-15 (6C) and IL-21 (6D) measured in the supernatants of the co-culture of each of the indicated tumor cell lines with T cells transduced with one of (i)-(v), as follows: (i) E7 TCR and TeIL-15 Lr1Ar2, (ii) E7 TCR and TeIL-21 Lr8Ar2, (iii) E7 TCR and TeIL-21/15 FurinA-P2A Ar2, (iv) E7 TCR and secreted IL-21/15 (sIL-21/15), or (v) E7 TCR alone. Untransduced (UTDX) T cells served as a control.

Figure 7B:
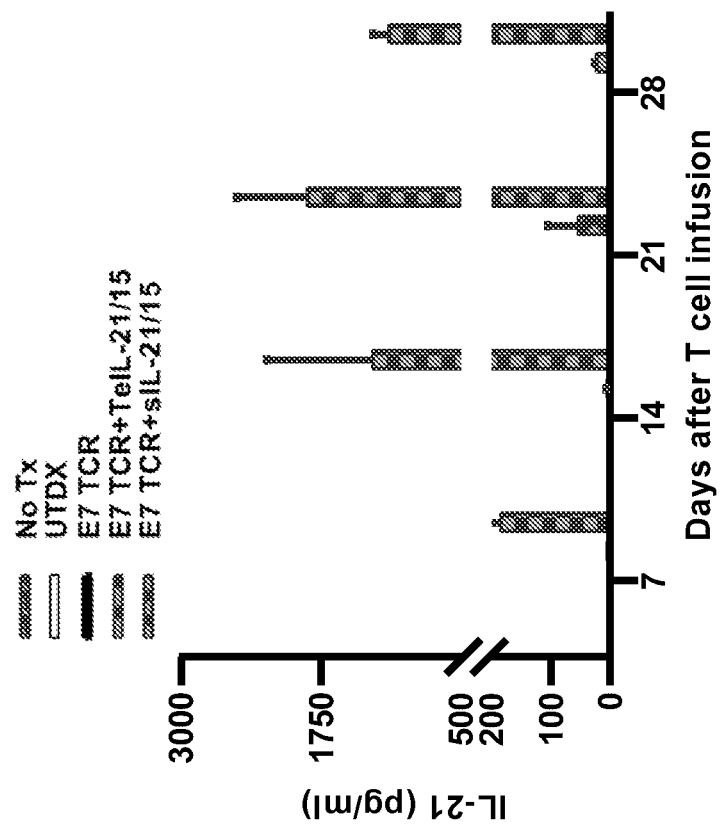
Figure 7A:
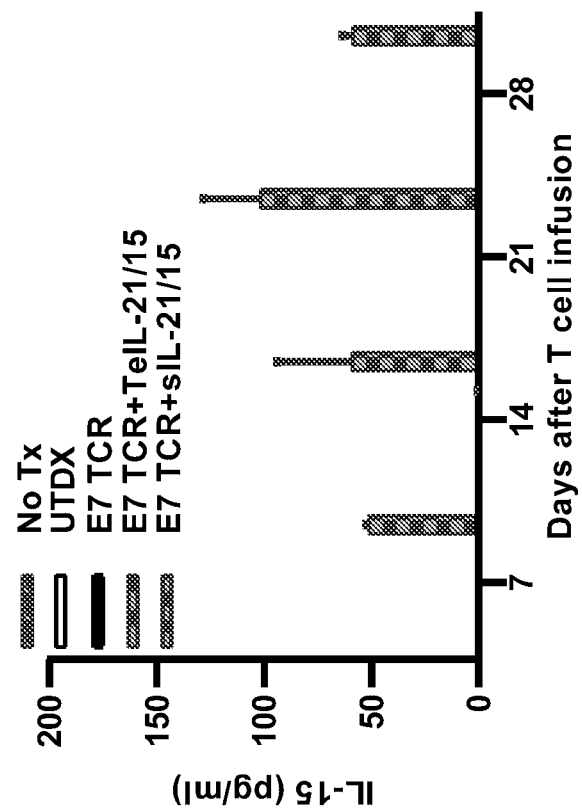

FIGS. 7A-7B are graphs showing the concentration (pg/mL) of IL-15 (7A) and IL-21 (7B) measured in the sera of healthy NSG mice infused with untransduced cells (UTDX), HBSS (No Tx), or transduced cells, at the indicated number of days after infusion. Cells were transduced with one of (i)-(iii), as follows: (i) E7 TCR and TeIL-21/15 FurinA-P2A Ar2, (ii) E7 TCR and secreted IL-21/15 (sIL-21/15), or (iii) E7 TCR alone.

Figure 7D:
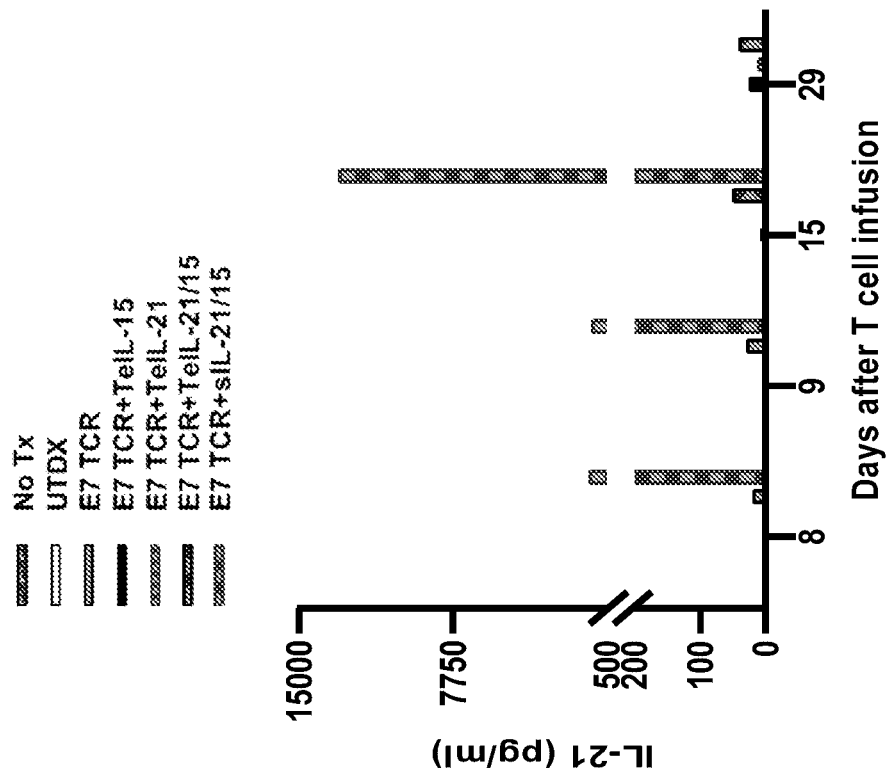
Figure 7C:
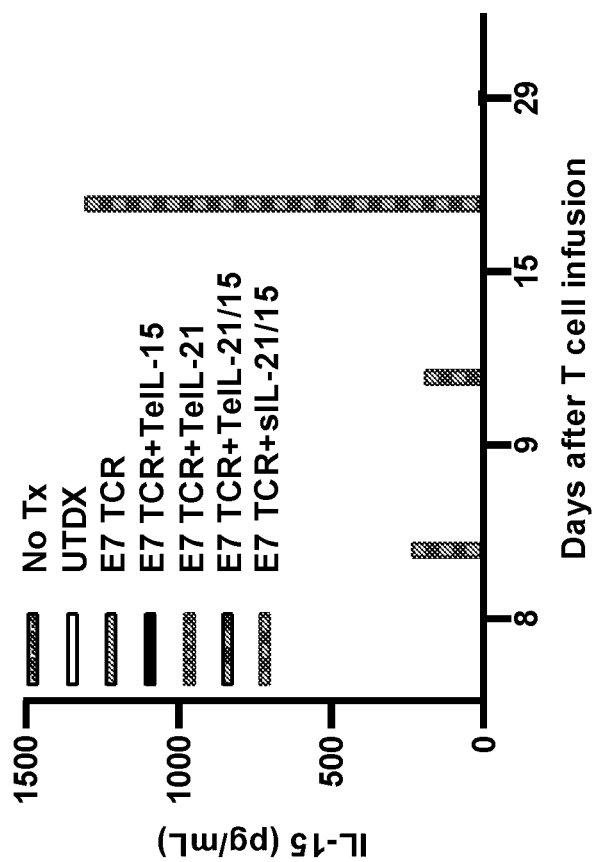

FIGS. 7C-7D are graphs showing the concentration (pg/mL) of IL-15 (7C) and IL-21 (7D) measured in the sera of tumor-bearing NSG mice infused with untransduced cells (UTDX), HBSS (No Tx), or transduced cells, at the indicated number of days after infusion. T cells were transduced with one of (i)-(v), as follows: (i) E7 TCR and TeIL-15 Lr1Ar2, (ii) E7 TCR and TeIL-21 Lr8Ar2, (iii) E7 TCR and TeIL-21/15 FurinA-P2A Ar2, (iv) E7 TCR and secreted IL-21/15 (sIL-21/15), or (v) E7 TCR alone.

FIGS. 8A-8G are graphs showing the concentration (pg/mL) of IFN-γ, TNF-α, GM-CSF, IL-2, MIP-1α, IL-2Rα, and IL-6 (8A-8G, respectively) observed in tumor-bearing mice at the indicated number of days following infusion of untransduced cells (UTDX), HBSS (No Tx), or transduced cells. T cells were transduced with one of (i)-(v), as follows: (i) E7 TCR and TeIL-15 Lr1Ar2, (ii) E7 TCR and TeIL-21 Lr8Ar2, (iii) E7 TCR and TeIL-21/15 FurinA-P2A Ar2, (iv) E7 TCR and secreted IL-21/15 (sIL-21/15), or (v) E7 TCR alone.

Figure 9:
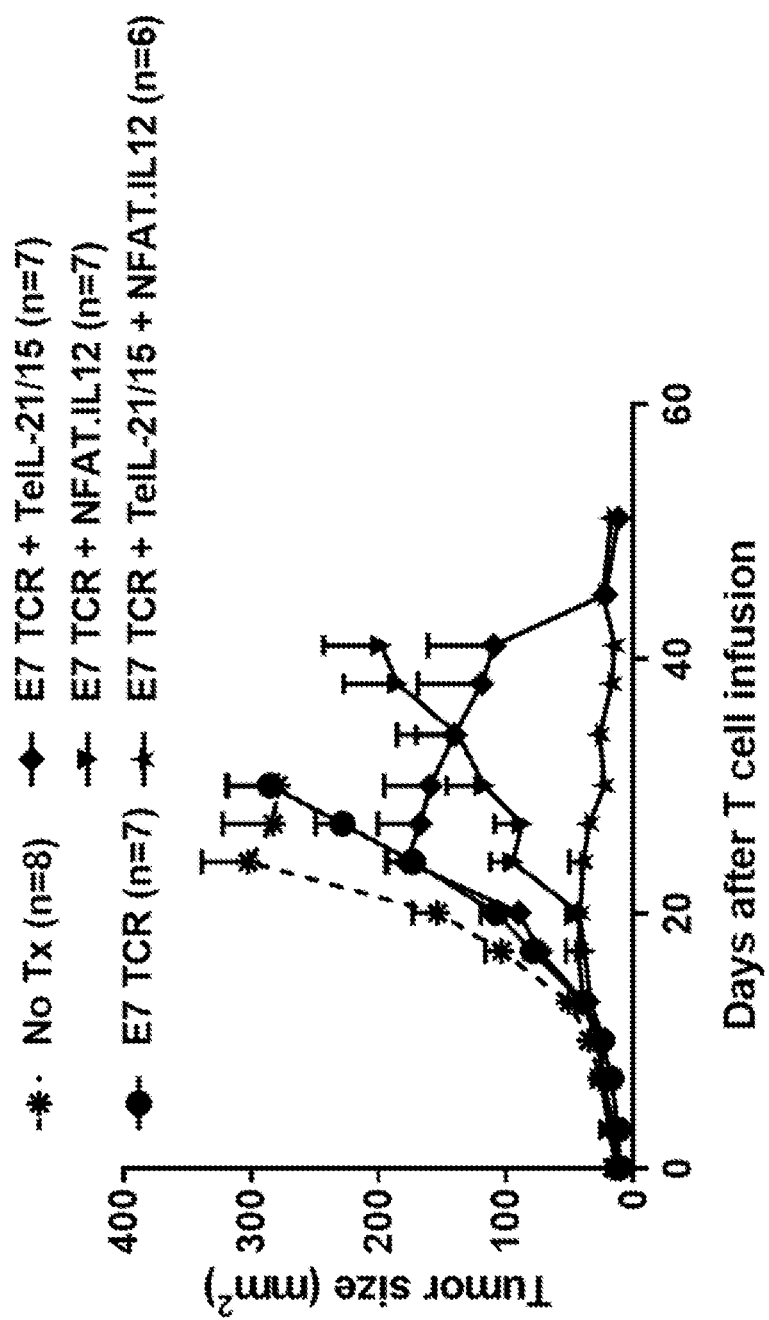

FIG. 9 is a graph showing the tumor size (mm²) measured in tumor-bearing mice at the indicated number of days after infusion of HBSS (No Tx) (*) or transduced T cells. The infused T cells were transduced with one of (i)-(iv), as follows: (i) E7 TCR and NFAT.IL12 (triangles), (ii) E7 TCR and TeIL-21/15 FurinA-P2A Ar2 and NFAT.IL12 (stars), (iii) E7 TCR and TeIL-21/15 FurinA-P2A Ar2 (diamonds), or (iv) E7 TCR alone (control) (circles). n=number of mice in each experiment.

DETAILED DESCRIPTION OF THE INVENTION

Embodiments of the invention provide nucleic acids and polypeptides which provide the co-expression of interleukin (IL)-21 and IL-15 by a host cell, each interleukin being bound to the cell membrane by a cell membrane anchor moiety. The inventive nucleic acids and polypeptides may provide any one or more of a variety of advantages. The advantages may include, for example, high expression levels of both membrane-bound IL-15 and membrane-bound IL-21. Cells expressing the inventive nucleic acids or polypeptides may provide enhanced function (e.g., increased anti-tumor efficacy) as compared to cells transduced with an antigen-specific receptor alone or cells co-transduced with an antigen-specific receptor and no more than one of IL-15 or IL-21. Without being bound to a particular theory or mechanism, it is also believed that the absence of the IL-15 receptor subunit alpha (IL-15Rα) from the inventive nucleic acids advantageously provides more room, e.g., for an IL-21 nucleotide sequence, as compared to nucleic acids which contain both IL-15Rα and IL-15 nucleotide sequences.

In some cases, the clinical utility of IL-15 and/or IL-21 in the setting of adoptively transferred T cells may be constrained in part by dose-limiting toxicity and the need for repeated administration. The inventive nucleic acids and polypeptides may, advantageously, ameliorate these limitations by providing for the autocrine expression of IL-15 and IL-21 by the host cell expressing the nucleic acid or polypeptide. Without being bound to a particular theory or mechanism, it is believed that because the IL-15 and IL-21 molecules are tethered to the cell which expresses the inventive nucleic acid, the cell provides an IL-15 and IL-21 signal to itself. It is believed that such autocrine IL-15 expression may reduce or avoid the undesirable excessive cell growth which may be observed in the presence of soluble IL-15. By connecting the interleukin to a cell membrane anchor moiety via a flexible linker, the inventive nucleic acids and polypeptides may reduce the systemic toxicity which may be caused by free cytokine molecules. Without being bound to a particular theory or mechanism, it is believed that because IL-15 primarily signals via the pro-cell growth proteins STAT5A/STAT5B, while IL-21 primarily signals via the pro-cell death proteins STAT1 and STAT3, the co-expression of IL-15 and IL-21 provided by the inventive nucleic acids and polypeptides may reduce or avoid the undesirable excessive cell growth which may be observed in the presence of IL-15 alone.

An embodiment of the invention provides a nucleic acid comprising a nucleotide sequence encoding an amino acid sequence of Formula I:

$$S^1\text{-}N^1\text{-}L^1\text{-}C^1{}_a\text{-}L^2\text{-}S^2\text{-}N^2\text{-}L^3\text{-}C^2{}_b.$$ (Formula I).

Signal Sequences

In an embodiment, each of $S^1$ and $S^2$ of Formula I is, independently, a signal sequence. The signal sequence is not limited and may be any sequence which facilitates the translocation of the encoded polypeptide to the cell membrane. Examples of signal sequences are human granulocyte-macrophage colony-stimulating factor (GM-CSF) receptor signal sequence, human prolactin signal sequence, and human IgE signal sequence. Preferably, the signal sequence is a human IgE signal sequence. The human IgE signal sequence may comprise, consist, or consist essentially of the amino acid sequence of MDWTWILFLVAAATRVHS (SEQ ID NO: 1). The human IgE signal sequence may comprise, consist, or consist essentially of the amino acid sequence of NIKGSPWKGSLLLLLVSNLLLCQSVAP (SEQ ID NO: 38). Without being bound to a particular theory or mechanism, while it is believed that the signal sequence may facilitate expression of the cell-membrane bound interleukin, the presence of the signal sequence in the expressed membrane-bound interleukin may not be necessary in order for the membrane-bound interleukin to function. In an embodiment of the invention, upon expression of the membrane-bound interleukin by the cell, the signal sequence may be cleaved off of the membrane-bound interleukin.

Interleukins

In an embodiment, one of $N^1$ and $N^2$ in Formula I is an interleukin (IL)-21 amino acid sequence and one of $N^1$ and $N^2$ is an IL-15 amino acid sequence. Although $N^1$ may be an IL-15 amino acid sequence and $N^2$ may be an IL-21 amino acid sequence, in a preferred embodiment, $N^1$ is an IL-21 amino acid sequence and $N^2$ is an IL-15 amino acid sequence.

IL-21 and IL-15 are pleiotropic, four α-helical bundle type I cytokines. IL-21 binds to the IL-21 receptor (IL-21R) and co-receptor, the common gamma chain (CD132), and IL-15 binds to the IL-15 receptor alpha (IL-15Rα) and co-receptors, the IL-2/IL-15 receptor beta chain (CD122) and CD132. Upon binding to their respective receptors and co-receptors, IL-21 and IL-15 initiate the activation of one or more of various downstream signaling targets including, for example, proteins in the JAK-STAT pathway such as the JAK kinases (e.g., JAK1 and JAK3), STAT proteins (e.g., STAT1, STAT3, STAT5A, and STAT5B), and the proteins in the phosphoinositol 3-kinase (PI 3-kinase) and MAP kinase pathways. Without being bound to a particular theory or mechanism, it is believed that IL-21 may induce one or more of the differentiation, death and activity of certain immune cells (e.g. T cells and NK cells), and IL-15 may induce one or more of the differentiation, proliferation and activity of certain immune cells (e.g. T cells and NK cells).

In an embodiment, the IL-21 sequence is a human IL-21 sequence. Human IL-21 amino acid sequences include Genbank Accession Nos: AAU88182.1, EAX05226.1, CAI94500.1, CAJ47524.1, CAL81203.1, CAN87399.1, CAS03522.1, CAV33288.1, CBE74752.1, CBI70418.1, CBI85469.1, CBI85472.1, CBL93962.1, CCA63962.1, AAG29348.1, AAH66258.1, AAH66259.1, AAH66260.1, AAH66261.1, AAH66262.1, AAH69124.1, and ABG36529.1. Other human IL-21 sequences, as well as other IL-21 species can be employed in accordance with the invention. In a preferred embodiment, the IL-21 amino acid sequence is the amino acid sequence of mature, human IL-21. Mature, human IL-21 comprises, consists, or consists essentially of the amino acid sequence of SEQ ID NO: 2.

In an embodiment, the IL-15 sequence is a human IL-15 sequence. Human IL-15 amino acid sequences include Genbank Accession Nos: NP 751915.1, NP 000576.1, AAI00963.1, AAI00964.1, AAI00962.1, CAA71044.1, AAH18149.1, AAB97518.1, CAA63914.1, and CAA63913.1. Other human IL-15 sequences, as well as other IL-15 species can be employed in accordance with the invention. In a preferred embodiment, the IL-15 amino acid sequence is the amino acid sequence of mature, human IL-15. Mature, human IL-15 comprises, consists, or consists essentially of the amino acid sequence of SEQ ID NO: 3.

The IL-21 and IL-15 amino acid sequences encoded by the inventive nucleic acids may comprise any functional portion of mature IL-21 or mature IL-15, respectively. The functional portion can be any portion comprising contiguous amino acids of the interleukin of which it is a part, provided that the functional portion specifically binds to the respective interleukin receptor. The term "functional portion" when used in reference to an interleukin refers to any part or fragment of the interleukin, which part or fragment retains the biological activity of the interleukin of which it is a part (the parent interleukin). Functional portions encompass, for example, those parts of an interleukin that retain the ability to specifically bind to the respective interleukin receptor, activate the downstream targets of the interleukin, and/or induce one or more of the differentiation, proliferation (or death) and activity of immune cells, e.g., NK cells and T cells, to a similar extent, the same extent, or to a higher extent, as the parent interleukin. The biological activity of the functional portion of the interleukin may be measured using assays known in the art. In reference to the parent interleukin, the functional portion can comprise, for instance, about 60%, about 70%, about 80%, about 90%, about 95%, or more, of the parent interleukin.

Included in the scope of the invention are functional variants of the interleukins described herein. The term "functional variant" as used herein refers to an interleukin having substantial or significant sequence identity or similarity to a parent interleukin, which functional variant retains the biological activity of the interleukin of which it is a variant. Functional variants encompass, for example, those variants of the interleukin described herein (the parent interleukin) that retain the ability to specifically bind to the respective interleukin receptor, activate the downstream targets of the interleukin, and/or induce one or more of the differentiation, proliferation (or death) and activity of immune cells, e.g., T cells and NK cells, to a similar extent, the same extent, or to a higher extent, as the parent interleukin. In reference to the parent interleukin, the functional variant can, for instance, be at least about 80%, about 90%, about 95%, about 99% or more identical in amino acid sequence to the parent interleukin.

A functional variant can, for example, comprise the amino acid sequence of the parent interleukin with at least one conservative amino acid substitution. Alternatively or additionally, the functional variants can comprise the amino acid sequence of the parent interleukin with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent interleukin.

Amino acid substitutions of the interleukin are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The interleukin can consist essentially of the specified amino acid sequence or sequences described herein, such that other components, e.g., other amino acids, do not materially change the biological activity of the functional variant.

Cell Membrane Anchor Moieties

The nucleic acids and polypeptide(s) of embodiments of the invention may comprise one or more cell membrane anchor moieties. The cell membrane anchor moiety may be any moiety which binds the interleukin to the cell membrane. Each cell membrane anchor moiety may, independently, be an amino acid sequence or a moiety that is not an amino acid sequence (a non-peptide cell membrane anchor moiety). In Formula I, each of a and b is, independently, 0 or 1. When a is 1, $C^1$ is a cell membrane anchor moiety that is an amino acid sequence (e.g., a transmembrane-intracellular amino acid sequence or a transmembrane amino acid sequence). When b is 1, $C^2$ is a cell membrane anchor moiety that is an amino acid sequence (e.g., a transmembrane-intracellular amino acid sequence or a transmembrane amino acid sequence).

In an embodiment of the invention, each of $C^1$ and $C^2$ of Formula I is, independently, a transmembrane-intracellular amino acid sequence or a transmembrane amino acid sequence. In an embodiment of the invention, each of $C^1$ and $C^2$ of Formula I is, independently, a B7-1 transmembrane-intracellular amino acid sequence, a B7-2 transmembrane-intracellular amino acid sequence, a CD8α transmembrane-intracellular amino acid sequence, a B7-1 transmembrane amino acid sequence, a B7-2 transmembrane amino acid sequence, or a CD8α transmembrane amino acid sequence. In a preferred embodiment, each of $C^1$ and $C^2$ of Formula I is, independently, a B7-1 transmembrane-intracellular amino acid sequence or a CD8α transmembrane amino acid sequence. In an embodiment of the invention, in Formula I, a is 1, b is 1, and each of $C^1$ and $C^2$ is, independently, a CD8α transmembrane amino acid sequence comprising, consisting, or consisting essentially of the amino acid sequence of IYIWAPLAGTCGVLLLSLVIT (SEQ ID NO: 4) or a B7-1 transmembrane-intracellular amino acid sequence comprising, consisting, or consisting essentially of the amino acid sequence of LLPSWAITLISVNGIFVIC-CLTYCFAPRCRERRRNERLRRESVRPV (SEQ ID NO: 5).

In an embodiment of the invention, in Formula I, one or both of a and b is, independently, 0. When a is 0, the amino acid sequence encoded by $L^1$ further comprises a cell membrane anchor moiety that is not an amino acid sequence (a non-peptide cell membrane anchor moiety). When b is 0, the amino acid sequence encoded by $L^3$ further comprises a cell membrane anchor moiety that is not an amino acid sequence (a non-peptide cell membrane anchor moiety).

The non-peptide cell membrane anchor moiety may be a glycolipid that can be attached to the C-terminus of an amino acid sequence during posttranslational modification and which binds the interleukin to the cell membrane. An example of such a glycolipid is a glycophosphatidylinositol (GPI) anchor. Accordingly, in an embodiment of the invention, the non-peptide cell membrane anchor moiety is a GPI anchor. GPI anchors have a structure that includes a phosphoethanolamine linker, glycan core, and phospholipid tail. The glycan core can be variously modified with side chains, such as a phosphoethanolamine group, mannose, galactose, sialic acid, or other sugars. Examples of GPI anchors are described in, for example, Paulick et al., *Biochemistry*, 47: 6991-7000 (2008).

Linkers

In an embodiment of the invention, each of $L^1$, $L^2$, and $L^3$ of Formula I is, independently, a linker sequence. The composition of the linker sequence is not particularly limited and may be any linker sequence which binds the interleukin to the cell membrane anchor moiety.

In a preferred embodiment, $L^2$ of Formula I is a cleavable linker sequence. In this regard, the polypeptide encoded by the inventive nucleic acids may be cleaved such that two polypeptides are produced: a first polypeptide comprising an IL-21 amino acid sequence connected to a cell membrane anchor moiety via a linker sequence and a second polypeptide comprising an IL-15 amino acid sequence connected to a cell membrane anchor moiety via a linker sequence. The length of the linker sequence $L^2$ of Formula I is not limited and may be from about 20 to about 30 amino acid residues, for example, about 20, about 21, about 22, about 23, about 24, about 25, about 26, about 27, about 28, about 29, about 30 amino acid residues, or a range between any two of the foregoing values.

In an embodiment, the cleavable linker sequence comprises a "self-cleaving" 2A peptide. "Self-cleaving" 2A peptides are described, for example, in Liu et al., *Sci. Rep.*, 7(1): 2193 (2017). 2A peptides are viral oligopeptides that mediate cleavage of polypeptides during translation in eukaryotic cells. The designation "2A" refers to a specific region of the viral genome. Without being bound to a particular theory or mechanism, it is believed that the mechanism of 2A-mediated "self-cleavage" is ribosome skipping of the formation of a glycyl-prolyl peptide bond at the C-terminus of the 2A peptide. Different 2A peptides may comprise, at the C-terminus, the consensus amino acid sequence of GDVEX$_1$NPGP (SEQ ID NO: 6), wherein X$_1$ of SEQ ID NO: 6 is any naturally occurring amino acid residue. In an embodiment of the invention, $L^2$ of Formula I is a porcine teschovirus-1 2A (P2A) amino acid sequence, equine rhinitis A virus (E2A) amino acid sequence, thosea asigna virus 2A (T2A) amino acid sequence, or foot-and-mouth disease virus (F2A) amino acid sequence. In an embodiment of the invention, $L^2$ of Formula I is 2A peptide amino acid sequence comprising, consisting, or consisting essentially of, the amino acid sequence of

```
                                          (SEQ ID NO: 7)
GSGATNFSLLKQAGDVEENPGP (P2A), (SEQ ID NO: 8)
GSGQCTNYALLKLAGDVESNPGP (E2A),
or (SEQ ID NO: 9)
GSGEGRGSLLTCGDVEENPGP (T2A).
```

In an embodiment, the cleavable linker sequence comprises a furin-cleavable sequence. Exemplary furin cleavage sequences are described in Duckert et al., *Protein Engineering, Design & Selection*, 17(1): 107-112 (2004) and U.S. Pat. No. 8,871,906, each of which is incorporated herein by reference. In an embodiment of the invention, the furin-cleavable sequence is represented by the formula P4-P3-P2-P1 (Formula II), wherein P4 is an amino acid residue at the amino end, P1 is an amino acid residue at the carboxyl end, P1 is an arginine or a lysine residue, and the sequence is cleavable at the carboxyl end of P1 by furin. In another embodiment of the invention, the furin-cleavable sequence of Formula II (i) further comprises amino acid residues represented by P6-P5 at the amino end, (ii) further comprises amino acid residues represented by P1'-P2' at the carboxyl end, (iii) wherein if P1 is an arginine or a lysine residue, P2' is tryptophan, and P4 is arginine, valine or lysine, provided that if P4 is not arginine, then P6 and P2 are basic residues, and (iv) the sequence is cleavable at the carboxyl end of P1 by furin. In an embodiment of the invention, the furin cleavage sequence comprises R-$X_1$-$X_2$-R, wherein $X_1$ is any naturally occurring amino acid and $X_2$ is arginine or lysine (SEQ ID NO: 10).

In an embodiment of the invention, the cleavable linker sequence comprises both a 2A peptide sequence and a furin-cleavable sequence. In an embodiment of the invention, $L^2$ of Formula I is a furin-cleavable-P2A amino acid sequence. The furin-cleavable-P2A amino acid sequence may comprise, consist, or consist essentially of (SEQ ID NO: 11)
RAKRSGSGATNFSLLKQAGDVEENPGP.

In a preferred embodiment, each of $L^1$ and $L^3$ of Formula I is, independently, a flexible linker. The length of the linker sequence of each of $L^1$ and $L^3$ of Formula I is not limited and may, independently, be from about 10 to about 65 amino acid residues, about 18 to about 61 amino acid residues, or about 25 to about 50 amino acid residues. For example, the length of the linker sequence of each of $L^1$ and $L^3$ of Formula I may, independently, be about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65 amino acid residues, or a range between any two of the foregoing values. In an embodiment of the invention, the flexible linker comprises mainly glycine and serine residues. For example, the flexible linker may comprise one or more repeats of one or both of $G_4S$ and $G_5S$ (e.g., about 3 to about 15 or about 5 to about 12 repeats of $G_4S$ and $G_3S$).

In an embodiment, each of $L^1$ and $L^3$ of Formula I is, independently, (i) a polypeptide of Formula III: $X^1_m X^2_n X^3_p X^4_q$ (Formula III) (as further defined below); (ii) a polypeptide of Formula IV: $X^5_r X^6_s X^7_t$ (Formula IV) (as further defined below); or (iii) 10 to 30 amino acid residues selected, independently, from glycine, serine, threonine, lysine, glutamic acid, and proline.

In an embodiment of the invention, one or both of $L^1$ and $L^3$ of Formula I is a polypeptide of Formula III: $X^1_m X^2_n X^3_p X^4_q$ (Formula III), wherein:
each of m, p, and q is, independently, 0 or 1;
n is an integer from 20 to 65;
$X^2$ is a plurality of amino acid residues, each of which is independently selected from glycine and serine; and
each of $X^1$, $X^3$, and $X^4$ is, independently, any one naturally occurring amino acid residue.

In an embodiment, in Formula III, n is an integer from 20 to 60, from 25 to 60, or from 25 to 50.

In an embodiment, in Formula III, m is 0, n is 25, p is 1, and q is 1, wherein $X^3$ is leucine and $X^4$ is glutamine. In this regard, a polypeptide of Formula III may comprise or consist of the amino acid sequence of SEQ ID NO: 12 (Lr1 of Table 3).

In an embodiment, in Formula III, m is 0, n is 45, p is 0, and q is 0. In this regard, a polypeptide of Formula III may comprise or consist of the amino acid sequence of SEQ ID NO: 14 (Lr6 of Table 3).

In an embodiment, in Formula III, m is 0, n is 46, p is 1, and q is 1, wherein $X^3$ is leucine and $X^4$ is glutamine. In this regard, a polypeptide of Formula III may comprise or consist of the amino acid sequence of SEQ ID NO: 16 (Lr8 of Table 3).

In an embodiment, in Formula III, m is 1, n is 58, p is 1, and q is 1, wherein X1 is alanine, $X^3$ is alanine, and $X^4$ is serine. In this regard, a polypeptide of Formula III may comprise or consist of the amino acid sequence of SEQ ID NO: 17 (Lr9 of Table 3).

In an embodiment of the invention, one or both of $L^1$ and $L^3$ of Formula I is a polypeptide of Formula IV: $X^5_r X^6_s X^7_t$ (Formula IV), wherein:
s is 1;
each of r and t is, independently, an integer from 20 to 25;
each $X^5$ and each $X^7$ is, independently, a plurality of amino acid residues selected from alanine, lysine, and glutamic acid; and
$X^6$ is any one naturally occurring amino acid residue.

In an embodiment, in Formula IV, r is 22, s is 1, and t is 23, wherein $X^6$ is leucine. In this regard, a polypeptide of Formula IV may comprise or consist of the amino acid sequence of SEQ ID NO: 15 (Lr7 of Table 3).

In an embodiment of the invention, one or both of $L^1$ and $L^3$ of Formula I is from 10 to 30 amino acid residues selected, independently, from glycine, serine, threonine, lysine, glutamic acid, and proline. In an embodiment, one or both of $L^1$ and $L^3$ of Formula I is from 10 to 20, preferably, 18 amino acid residues selected, independently, from glycine, serine, threonine, lysine, glutamic acid, and proline. In this regard, one or both of $L^1$ and $L^3$ of Formula I comprises or consists of the amino acid sequence of SEQ ID NO: 13 (Lr2 of Table 3).

Nucleic Acids

In an embodiment of the invention, the nucleic acid comprises a nucleotide sequence encoding an amino acid sequence at least about 85%, about 90%, about 91%, about 92%, about 93%, about 94%, about 95%, about 96%, about 97%, about 98%, about 99%, or about 100% identical to the amino acid sequence of any one of SEQ ID NOs: 32-37 (Table 6A). For example, the nucleic acid may comprise a nucleotide sequence at least about 85%, about 90%, about 91%, about 92%, about 93%, about 94%, about 95%, about 96%, about 97%, about 98%, about 99%, or about 100% identical to the nucleotide sequence of any one of SEQ ID NOs: 39-44 (Table 6B).

The terms "nucleic acid" and "polynucleotide," as used herein, refer to a polymeric form of nucleotides of any length, either ribonucleotides (RNA) or deoxyribonucleotides (DNA). These terms refer to the primary structure of the molecule, and thus include double- and single-stranded DNA, double- and single-stranded RNA, and double-stranded DNA-RNA hybrids. The terms include, as equivalents, analogs of either RNA or DNA made from nucleotide analogs and modified polynucleotides such as, though not limited to, methylated and/or capped polynucleotides. Suitable nucleotide analogs are known and are described in, e.g., U.S. Patent Application Publication 2012/0101148, and references cited therein. In an embodiment of the invention, the nucleic acid is complementary DNA (cDNA).

The term "nucleotide" as used herein refers to a monomeric subunit of a polynucleotide that consists of a heterocyclic base, a sugar, and one or more phosphate groups. The naturally occurring bases (guanine (G), adenine (A), cytosine (C), thymine (T), and uracil (U)) are typically derivatives of purine or pyrimidine, though the invention includes the use of naturally and non-naturally occurring base analogs. The naturally occurring sugar is the pentose (five-carbon sugar) deoxyribose (which forms DNA) or ribose (which forms RNA), though the invention includes the use of naturally and non-naturally occurring sugar analogs. Nucleic acids are typically linked via phosphate bonds to form nucleic acids or polynucleotides, though many other linkages are known in the art (e.g., phosphorothioates, boranophosphates, and the like). Methods of preparing polynucleotides are within the ordinary skill in the art (Green and Sambrook, *Molecular Cloning: A Laboratory Manual*, (4th Ed.) Cold Spring Harbor Laboratory Press, New York (2012)).

In some embodiments, the nucleotide sequence may be codon optimized. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Codon optimization of the nucleotide sequence may also reduce secondary mRNA structures that would interfere with translation, thus increasing translation efficiency. In an embodiment of the invention, the nucleotide sequence is codon-optimized for expression in human tissues.

Vectors

In an embodiment of the invention, the inventive nucleic acid is carried in a recombinant expression vector. Accordingly, an embodiment of the invention provides a recombinant expression vector comprising any of the inventive nucleic acids described herein with respect to other aspects of the invention.

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The recombinant expression vector can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector. The vector may contain regulatory nucleic acid sequences which provide for expression of the inventive nucleic acid.

The recombinant expression vector can be any suitable recombinant expression vector. Suitable vectors include those designed for propagation and expansion or for expression or both, such as plasmids and viruses. For example, the vector can be selected from the pUC series (Fermentas Life Sciences, Glen Burnie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors useful in the context of the invention include pBI01, pBI101.2, pBI101.3, pBI121 and pBIN19 (Clontech). Examples of animal expression vectors useful in the context of the invention include pEUK-C1, pMAM, and pMAMneo (Clontech).

In some embodiments, the recombinant expression vector is a viral vector. Suitable viral vectors include, without limitation, lentiviral, retroviral, alphaviral, vaccinial, adenoviral, adenoassociated viral, herpes viral, and fowl pox viral vectors, and preferably have a native or engineered capacity to transform T cells.

The recombinant expression vectors can be prepared using standard recombinant DNA techniques described in, for example, Green and Sambrook, *Molecular Cloning: A Laboratory Manual*, (4th Ed.) Cold Spring Harbor Laboratory Press, New York (2012). Constructs of expression vectors, which are circular or linear, can be prepared to contain a replication system functional in a prokaryotic or eukaryotic host cell. Replication systems can be derived, e.g., from ColE1, 2µ plasmid, λ, SV40, bovine papilloma virus, and the like.

The recombinant expression vector can comprise regulatory sequences, such as transcription and translation initiation and termination codons, which are specific to the type of host (e.g., bacterium, fungus, plant, or animal) into which the vector is to be introduced, as appropriate, and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the recombinant expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleic acid encoding the amino acid sequence of Formula I. Preferably, the promoter is functional in T cells. The selection of a promoter, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vector can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

Polypeptide(s)

Another embodiment of the invention provides a polypeptide encoded by the any of the nucleic acids described herein. The term "polypeptide" as used herein includes oligopeptides and refers to a single chain of amino acids connected by one or more peptide bonds.

In an embodiment of the invention, the polypeptide comprises an amino acid sequence at least about 85%, about 90%, about 91%, about 92%, about 93%, about 94%, about 95%, about 96%, about 97%, about 98%, about 99%, or about 100% identical to the amino acid sequence of any one of SEQ ID NOs: 32-37 (Table 6A).

In embodiments wherein $L^2$ of Formula I is a cleavable linker, the polypeptide produced upon expression of the inventive nucleic acid by a host cell may be cleaved such that two polypeptides are produced: a first polypeptide comprising an IL-21 amino acid sequence connected to a cell membrane anchor moiety via a linker sequence and a second polypeptide comprising an IL-15 amino acid sequence connected to a cell membrane anchor moiety via a linker sequence.

In an embodiment of the invention, the polypeptide comprising an IL-21 amino acid sequence connected to a cell membrane anchor moiety via a linker sequence may comprise an amino acid sequence that is at least about 85%, about 90%, about 91%, about 92%, about 93%, about 94%, about 95%, about 96%, about 97%, about 98%, about 99%, or about 100% identical to the amino acid sequence of any one of SEQ ID NOs: 24-30 (Tables 4-5).

In an embodiment of the invention, the polypeptide comprising an IL-15 amino acid sequence connected to a cell membrane anchor moiety via a linker sequence may comprise an amino acid sequence that is at least about 85%, about 90%, about 91%, about 92%, about 93%, about 94%, about 95%, about 96%, about 97%, about 98%, about 99%, or about 100% identical to the amino acid sequence of any one of SEQ ID NOs: 19, 20, 22, and 31 (Tables 2 and 5).

Host Cells and Populations Thereof

Another embodiment of the invention further provides a host cell comprising any of the recombinant expression vectors described herein. Still another embodiment of the invention provides a host cell expressing any of the nucleic acids described herein or the one or more polypeptides described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing polypeptide(s) encoded by the inventive nucleic acids, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell or a natural killer (NK) cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD4$^+$ T cells, CD8$^+$ T cells (e.g., cytotoxic T cells), tumor infiltrating lymphocytes (TILs), memory T cells (e.g., central memory T cells and effector memory T cells), naïve T cells, and the like.

In an embodiment of the invention, the host cell comprises (e.g., expresses) an antigen-specific receptor. In a preferred embodiment, the antigen-specific receptor has antigenic specificity for a cancer antigen. The phrases "antigen-specific" and "antigenic specificity," as used herein, mean that the antigen-specific receptor can specifically bind to and immunologically recognize an antigen, or an epitope thereof, such that binding of the antigen-specific receptor to antigen, or the epitope thereof, elicits an immune response.

The term "cancer antigen," as used herein, refers to any molecule (e.g., protein, polypeptide, peptide, lipid, carbohydrate, etc.) solely or predominantly expressed or over-expressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host. Examples of cancer antigens include, but are not limited to, mesothelin, CD19, CD22, CD30, CD70, CD276 (B7H3), gp100, MART-1, Epidermal Growth Factor Receptor Variant III (EGFRVIII), Vascular Endothelial Growth Factor Receptor 2 (VEGFR-2), TRP-1, TRP-2, tyrosinase, human papillomavirus (HPV) 16 E6, HPV 16 E7, HPV 18 E6, HPV 18 E7, KK-LC-1, NY-BR-1, NY-ESO-1 (also known as CAG-3), SSX-2, SSX-3, SSX-4, SSX-5, SSX-9, SSX-10, MAGE-A1, MAGE-A2, BRCA, MAGE-A3, MAGE-A4, MAGE-A5, MAGE-A6, MAGE-A7, MAGE-A8, MAGE-A9, MAGE-A10, MAGE-A11, MAGE-Al2, HER-2, etc. In an embodiment of the invention, the cancer antigen may be a mutated antigen that is expressed or overexpressed by tumor or cancer cells and which is not expressed by normal, non-tumor, or non-cancerous cells. Examples of such cancer antigens may include, but are not limited to, mutated KRAS and mutated p53. T cells having antigenic specificity for a cancer antigen may, advantageously, reduce or avoid cross-reactivity with normal tissues such as, for example, that which may occur using T cells having antigenic specificity for minor histocompatability antigens. In a preferred embodiment, the cancer antigen is HPV 16 E7, HPV 18 E7, or KK-LC-1.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells.

In an embodiment of the invention, the antigen-specific receptor is an exogenous T cell receptor (TCR). By "exogenous" is meant that the TCR is not native to (naturally-occurring on) the T cell. The exogenous TCR may be a recombinant TCR. A recombinant TCR is a TCR which has been generated through recombinant expression of one or more exogenous TCR α-, β-, γ-, and/or δ-chain encoding genes. A recombinant TCR can comprise polypeptide chains derived entirely from a single mammalian species, or the recombinant TCR can be a chimeric or hybrid TCR comprised of amino acid sequences derived from TCRs from two different mammalian species. For example, the TCR can comprise a variable region derived from a murine TCR, and a constant region of a human TCR such that the TCR is "humanized." Any exogenous TCR having antigenic specificity for a cancer antigen may be useful in the inventive methods and compositions. The TCR generally comprises two polypeptides (i.e., polypeptide chains), such as an α-chain of a TCR, a β-chain of a TCR, a γ-chain of a TCR, a δ-chain of a TCR, or a combination thereof. Such polypeptide chains of TCRs are known in the art. The cancer antigen-specific TCR can comprise any amino acid sequence, provided that the TCR can specifically bind to and immunologically recognize a cancer antigen or epitope thereof. Examples of exogenous TCRs that may be useful in the inventive methods and compositions include, but are not limited to, those disclosed in, for example, U.S. Pat. Nos. 7,820,174; 7,915,036; 8,088,379; 8,216,565; 8,431,690; 8,613,932; 8,785,601; 9,128,080; 9,345,748; 9,487,573; 9,822,162; U.S. Patent Application Publication Nos. 2013/0116167; 2014/0378389; 2015/0246959; 2017/0145070, and International Patent Application Publication No. WO 2017/189254, each of which is incorporated herein by reference. In a preferred embodiment, the exogenous TCR is the anti-HPV 16 E7 TCR disclosed in U.S. Patent Application Publication No. 2017/0145070 or the anti-KK-LC-1 TCR disclosed in International Patent Application Publication No. WO 2017/189254.

In an embodiment of the invention, the antigen-specific receptor is a chimeric antigen receptor (CAR). Typically, a CAR comprises the antigen binding domain of an antibody, e.g., a single-chain variable fragment (scFv), fused to the transmembrane and intracellular domains of a TCR. Thus, the antigenic specificity of a TCR of the invention can be encoded by a scFv which specifically binds to the cancer antigen, or an epitope thereof. Any CAR having antigenic specificity for a cancer antigen may be useful in the inventive methods and compositions. Examples of CARs that may be useful in the inventive methods and compositions include, but are not limited to, those disclosed in, for example, U.S. Pat. Nos. 8,465,743; 9,266,960; 9,765,342; 9,359,447; 9,868,774 and U.S. Patent Application Publication No. 2017/0107286, each of which is incorporated herein by reference.

In an embodiment of the invention, the antigen-specific receptor is an endogenous TCR. In some embodiments, the T cell comprising the endogenous TCR does not comprise (e.g., express) a CAR or an exogenous TCR. In other embodiments, a T cell comprising an endogenous cancer antigen-specific TCR can also be transformed, e.g., transduced or transfected, with one or more nucleic acids encoding an exogenous (e.g., recombinant) TCR or other recombinant receptor (e.g., CAR). Such exogenous receptors, e.g., TCRs, can confer specificity for additional antigens to the transformed T cell beyond the antigens for which the endogenous TCR is naturally specific. This can, but need not, result in the production of T cells having dual antigen specificities.

In an embodiment of the invention, the inventive nucleic acids, recombinant expression vectors, polypeptide(s), host cells, and populations thereof may be isolated or purified. The term "isolated," as used herein, means having been removed from its natural environment. The term "purified," as used herein, means having been increased in purity, wherein "purity" is a relative term, and not to be necessarily construed as absolute purity. For example, the purity can be at least about 50%, can be greater than about 60%, about 70% or about 80%, about 90% or can be about 100%.

Pharmaceutical Compositions and Methods of Treatment

The inventive nucleic acids, recombinant expression vectors, polypeptide(s), host cells (and populations thereof) (hereinafter, "inventive IL-21/15 materials") may be included in a composition, such as a pharmaceutical composition. In this regard, the invention provides a pharmaceutical composition comprising any of the inventive IL-21/15 materials described herein and a pharmaceutically acceptable carrier.

Preferably, the carrier is a pharmaceutically acceptable carrier. With respect to pharmaceutical compositions, the carrier can be any of those conventionally used for the administration of cells. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier may be determined in part by the particular method used to administer the particular inventive IL-21/15 material. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the inventive IL-21/15 material, and in certain instances, a particular route can provide a more immediate and more effective response than another route.

Preferably, the inventive IL-21/15 material is administered by injection, e.g., intravenously. A suitable pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

For purposes of the invention, the dose, e.g., number of inventive host cells administered should be sufficient to effect, e.g., a therapeutic or prophylactic response, in the mammal over a reasonable time frame. For example, the number of inventive host cells administered should be sufficient to bind to a cancer antigen or treat or prevent cancer in a period of from about 2 hours or longer, e.g., 12 to 24 or more hours, from the time of administration. In certain embodiments, the time period could be even longer. The number of inventive host cells administered will be determined by, e.g., the efficacy of the particular population of host cells (e.g., T cells) to be administered and the condition of the mammal (e.g., human), as well as the body weight of the mammal (e.g., human) to be treated.

Many assays for determining an administered number of inventive host cells are known in the art. For purposes of the invention, an assay, which comprises comparing the extent to which target cells are lysed or one or more cytokines such as, e.g., IFN-γ and IL-2 is secreted upon administration of a given number of such T cells to a mammal among a set of mammals of which is each given a different number of the T cells, could be used to determine a starting number to be administered to a mammal. The extent to which target cells are lysed or cytokines such as, e.g., IFN-γ and IL-2 are secreted upon administration of a certain number can be assayed by methods known in the art. Secretion of cytokines such as, e.g., IL-2, may also provide an indication of the quality (e.g., phenotype and/or effectiveness) of a T cell preparation.

The number of inventive host cells administered also will be determined by the existence, nature and extent of any adverse side effects that might accompany the administration of a particular population of cells. Typically, the attending physician will decide the number of cells with which to treat each individual patient, taking into consideration a variety of factors, such as age, body weight, general health, diet, sex, route of administration, and the severity of the condition being treated. By way of example and not intending to limit the invention, the number of cells to be administered can be about $10 \times 10^6$ to about $10 \times 10^{11}$ cells per infusion, about $10 \times 10^9$ cells to about $10 \times 10^{11}$ cells per infusion, or $10 \times 10^7$ to about $10 \times 10^9$ cells per infusion.

It is contemplated that the inventive IL-21/15 materials can be used in methods of treating or preventing cancer in a mammal. In this regard, the invention provides a method of treating or preventing cancer in a mammal, comprising administering to the mammal any of the inventive IL-21/15 materials or pharmaceutical compositions described herein in an amount effective to treat or prevent cancer in the mammal.

One or more additional therapeutic agents can be coadministered to the mammal. By "coadministering" is meant administering one or more additional therapeutic agents and the inventive IL-21/15 material sufficiently close in time such that the inventive IL-21/15 material can enhance the effect of one or more additional therapeutic agents, or vice versa. In this regard, the inventive IL-21/15 material can be administered first and the one or more additional therapeutic agents can be administered second, or vice versa. Alternatively, the inventive IL-21/15 material and the one or more additional therapeutic agents can be administered simultaneously. Additional therapeutic agents that may enhance the function of the inventive IL-21/15 material may include, for example, one or more cytokines or one or more antibodies (e.g., antibodies that inhibit PD-1 function). An exemplary therapeutic agent that can be co-administered with the inventive IL-21/15 material is IL-2. Without being bound to a particular theory or mechanism, it is believed that IL-2 may enhance the therapeutic effect of the inventive populations of host cells.

An embodiment of the invention further comprises lymphodepleting the mammal prior to administering the inventive IL-21/15 material. Examples of lymphodepletion include, but may not be limited to, nonmyeloablative lymphodepleting chemotherapy, myeloablative lymphodepleting chemotherapy, total body irradiation, etc.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset or recurrence of the disease, or a symptom or condition thereof.

For purposes of the inventive methods, wherein populations of cells are administered, the cells can be cells that are allogeneic or autologous to the mammal. Preferably, the cells are autologous to the mammal.

With respect to the inventive methods, the cancer can be any cancer, including any of leukemia (e.g., B cell leukemia), sarcomas (e.g., synovial sarcoma, osteogenic sarcoma, leiomyosarcoma uteri, and alveolar rhabdomyosarcoma), lymphomas (e.g., Hodgkin lymphoma and non-Hodgkin lymphoma), hepatocellular carcinoma, glioma, head-neck cancer, acute lymphocytic cancer, acute myeloid leukemia, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer (e.g., colon carcinoma), esophageal cancer, uterine cervical cancer, gastrointestinal carcinoid tumor, hypopharynx cancer, larynx cancer, liver cancer, lung cancer, malignant mesothelioma, melanoma, multiple myeloma, nasopharynx cancer, oropharynx cancer, ovarian cancer, pancreatic cancer, penis, peritoneum, rectum, omentum, and mesentery cancer, pancreas, pharynx cancer, prostate cancer, rectal cancer, renal cancer, small intestine cancer, soft tissue cancer, stomach cancer, testicular cancer, thyroid cancer, ureter cancer, vagina, and urinary bladder cancer.

In embodiments where the cancer antigen is KK-LC-1, a preferred cancer is cancer of the bladder, uterine cervix, stomach, breast, lung, colon, rectum, or pancreas. A particularly preferred cancer is KK-LC-1-positive cancer. While the cancers most commonly associated with KK-LC-1 expression include cancer of the bladder, uterine cervix, stomach, breast, lung, colon, rectum, and pancreas, the methods may be used to treat any KK-LC-1-positive cancer, including those that occur at other anatomical areas.

In embodiments where the cancer antigen is HPV 16 (E6 or E7), a preferred cancer is cancer is cancer of the uterine cervix, oropharynx, anus, anal canal, anorectum, vagina, vulva, or penis. A particularly preferred cancer is HPV 16-positive cancer. While the cancers most commonly associated with HPV 16 infection include cancer of the uterine cervix, oropharynx, anus, anal canal, anorectum, vagina, vulva, and penis, the methods may be used to treat any HPV 16-positive cancer, including those that occur at other anatomical areas.

Another embodiment of the invention provides any of the nucleic acids, polypeptide(s), recombinant expression vectors, host cells, populations of cells, or pharmaceutical compositions described herein, for use in the treatment or prevention of cancer in a mammal.

It is contemplated that any of the inventive nucleic acids, polypeptide(s), recombinant expression vectors, host cells, populations of cells, or pharmaceutical compositions described herein may be useful as immunotherapy adjuvants, e.g., vaccine adjuvants. In this regard, an embodiment of the invention provides a method of enhancing the immune response of a mammal to an immunotherapy, e.g., a vaccine, the method comprising administering to the mammal (i) the vaccine and (ii) any of the inventive nucleic acids, polypeptide(s), recombinant expression vectors, host cells, populations of cells, or pharmaceutical compositions described herein in an amount effective to enhance the immune response of the mammal to the immunotherapy, e.g., vaccine.

Still another embodiment of the invention provides any of the inventive nucleic acids, polypeptide(s), recombinant expression vectors, host cells, populations of cells, or pharmaceutical compositions described herein, for use in the enhancement of an immune response of a mammal to an immunotherapy, e.g., vaccine.

The following examples further illustrate the invention but, of course, should not be construed as in any way limiting its scope.

EXAMPLES

The following materials and methods were employed in the experiments described in Examples 1-8.

Design and Construct of Tethered IL-15 and IL-21

Various IL-15 constructs were prepared. These included tethered IL-15 (TeIL-15) constructs (TeIL-15 Lr1, TeIL-15 Lr2, and TeIL-15 Lr6). The structure of each of the TeIL-15 constructs is composed of four fragments: a signal sequence, an IL-15 mature amino acid sequence, a flexible linker, and a cell membrane anchor moiety ("anchor") (FIG. 1A). The signal sequence is a human IgE signal sequence. The anchor Ar1 is a human CD8a transmembrane amino acid sequence.

In addition to the TeIL-15 constructs, a secreted IL-15 (IL-15S) construct and an IL-15RA construct were also prepared. The structure of the IL-15RA construct is composed of four fragments: a human IgE signal sequence, a mature IL-15 amino acid sequence, a flexible linker, and an IL-15 receptor subunit alpha (IL-15Rα) sequence. The structure of the IL-15S construct is composed of two fragments: a human IgE signal sequence and an IL-15 mature amino acid sequence.

The amino acid sequences of the various components employed in the IL-15 constructs is set forth in Table 1.

TABLE 1

| Component | Sequence |
| --- | --- |
| Signal sequence (IgE) | MDWTWILFLVAAATRVHS (SEQ ID NO: 1) |
| IL-15 | NWVNVISDLKKIEDLIQSMHIDATLYTESDVHPSCKVT AMKCFLLELQVISLESGDASIHDTVENLIILANNSLSS NGNVTESGCKECEELEEKNIKEFLQSFVHIVQMFINTS (SEQ ID NO: 3) |
| Linker (Lr) 1 | SGGGGSGGGGSGGGGSGGGGSGGGSLQ (SEQ ID NO: 12) |
| Lr2 | GSTSGSGKPGSGEGSTKG (SEQ ID NO: 13) |
| Lr6 | GGGGSGGGGSGGGGSGGGGSGGGGSGGGGSGGGGSGGGG SGGGGS (SEQ ID NO: 14) |
| Anchor (Ar) 1 | IYIWAPLAGTCGVLLLSLVIT (SEQ ID NO: 4) |
| Ar2 | LLPSWAITLISVNGIFVICCLTYCFAPRCRERRRNERLR RESVRPV (SEQ ID NO: 5) |
| IL-15Rα | ITCPPPMSVEHADIWVKSYSLYSRERYICNSGFKRKAGT SSLTECVLNKATNVAHWTTPSLKCIRDPALVHQRPAPPS TVTTAGVTPQPESLSPSGKEPAASSPSSNNTAATTAAIV PGSQLMPSKSPSTGTTEISSHESSHGTPSQTTAKNWELT ASASHQPPGVYPQGHSDTTVAISTSTVLLCGLSAVSLLA CYLKSRQTPPLASVEMEAMEALPVTWGTSSRDEDLENCS HHL (SEQ ID NO: 18) |

The amino acid sequences of each of the full length IL-15 constructs is set forth in Table 2. In Table 2, the IL-15 amino acid sequence is underlined, the anchor sequence (Ar1) is shown in bold, and the IL-15Rα is italicized.

TABLE 2

| IL-15 Construct | Amino Acid Sequence |
| --- | --- |
| TeIL-15 Lr1 | MDWTWILFLVAAATRVHSNWVNVISDLKKIEDLIQSMHIDATLYTESDVHPSCKVTAMKC FLLELQVISLESGDASIHDTVENLIILANNSLSSNGNVTESGCKECEELEEKNIKEFLQS FVHIVQMFINTSSGGGGSGGGGSGGGGSGGGGSGGGSLQIYIWAPLAGTCGVLLLSLVIT (SEQ ID NO: 19) |
| TeIL-15 Lr2 | MDWTWILFLVAAATRVHSNWVNVISDLKKIEDLIQSMHIDATLYTESDVHPSCKVTAMKCF LLELQVISLESGDASIHDTVENLIILANNSLSSNGNVTESGCKECEELEEKNIKEFLQSF VHIVQMFINTSGSTSGSGKPGSGEGSTKGIYIWAPLAGTCGVLLLSLVIT (SEQ ID NO: 20) |
| IL-15 RA | MDWTWILFLVAAATRVHSNWVNVISDLKKIEDLIQSMHIDATLYTESDVHPSCKVTAMKC FLLELQVISLESGDASIHDTVENLIILANNSLSSNGNVTESGCKECEELEEKNIKEFLQS FVHIVQMFINTSSGGGGSGGGGSGGGGSGGGGSGGGSLQ*ITCPPPMSVEHADIWVKSYS LYSRERYICNSGFKRKAGTSSLTECVLNKATNVAHWTTPSLKCIRDPALVHQRPAPPST VTTAGVTPQPESLSPSGKEPAASSPSSNNTAATTAAIVPGSQLMPSKSPSTGTTEISSH ESSHGTPSQTTAKNWELTASASHQPPGVYPQGHSDTTVAISTSTVLLCGLSAVSLLACY LKSRQTPPLASVEMEAMEALPVTWGTSSRDEDLENCSHHL* (SEQ ID NO: 21) |

TABLE 2-continued

IL-15
Construct Amino Acid Sequence

TelL-15  MDWTWILFLVAAATRVHSNWVNVISDLKKIEDLIQSMHIDATLYTESDVHPSCKVTAMKC
Lr6      FLLELQVISLESGDASIHDTVENLIILANNSLSSNGNVTESGCKECEELEEKNIKEFLQS
         HFVIVQMFINTSGGGGSGGGGSGGGGSGGGGSGGGGSGGGGSGGGGSGGGGSGGGG
         SIYIWAPLAGTCGVLLLSLVIT (SEQ ID NO: 22)

IL-15S   MDWTWILFLVAAATRVHSNWVNVISDLKKIEDLIQSMHIDATLYTESDVHPSCKVTAMKC
         FLLELQVISLESGDASIHDTVENLIILANNSLSSNGNVTESGCKECEELEEKNIKEFLQS
         FVHIVQMFINTS (SEQ ID NO: 23)

A total of seven tethered IL-21 (TeIL-21) constructs were prepared (TeIL-21 Lr1, TeIL-21 Lr2, TeIL-21 Lr6, TeIL-21 Lr7, TeIL-21 Lr8Ar1, TeIL-21 Lr9, and eIL-21 Lr8Ar2). The structure of each of the TeIL-21 constructs is composed of four fragments: a signal sequence, a mature IL-21 amino acid sequence, a flexible linker, and a cell membrane anchor moiety (FIG. 1B). The signal sequence is a human IgE signal sequence. The anchor sequence is a human CD8a transmembrane amino acid sequence (Ar1) or a human B7-1 transmembrane-intracellular amino acid sequence (Ar2).

The amino acid sequences of the various components employed in the TeIL-21 constructs is set forth in Table 3.

TABLE 3

| Component | Sequence |
|---|---|
| Signal sequence (IgE) | MDWTWILFLVAAATRVHS (SEQ ID NO: 1) |
| IL-21 | QGQDRHMIRMRQLIDIVDQLKNYVNDLVPEFLPAPEDVET NCEWSAFSCFQKAQLKSANTGNNERIINVSIKKLKRKPPS TNAGRRQKHRLTCPSCDSYEKKPPKEFLERFKSLLQKMIH QHLSSRTHGSEDS (SEQ ID NO: 2) |

TABLE 3-continued

| Component | Sequence |
|---|---|
| Linker (Lr) 1 | SGGGGSGGGGSGGGGSGGGGSGGGSLQ (SEQ ID NO: 12) |
| Lr2 | GSTSGSGKPGSGEGSTKG (SEQ ID NO: 13) |
| Lr6 | GGGGSGGGGSGGGGSGGGGSGGGGSGGGGSGGGGSGGGGS GGGGS (SEQ ID NO: 14) |
| Lr7 | AEAAAKEAAAKEAAAKEAAAKALEAEAAAKEAAAKEAAAK EAAAKA (SEQ ID NO: 15) |
| Lr8 | SGGGGSGGGGSGGGGSGGGGSGGGGSGGGGSGGGGSGGGG SGGGGSLQ (SEQ ID NO: 16) |
| Lr9 | AGGGSGGGGSGGGGSGGGGSGGGGSGGGGSGGGGSGGGGS GGGGSGGGSGGGGSGGGGSAS (SEQ ID NO: 17) |
| Anchor (Ar) 1 | IYIWAPLAGTCGVLLLSLVIT (SEQ ID NO: 4) |
| Ar2 | LLPSWAITLISVNGIFVICCLTYCFAPRCRERRRNERLRR ESVRPV (SEQ ID NO: 5) |

The amino acid sequences of each of the full length TeIL-21 constructs is set forth in Table 4. In Table 4, the IL-21 amino acid sequence is underlined, and the anchor sequence (Ar1 or Ar2) is shown in bold.

TABLE 4

| TelL-21 Construct | Amino acid Sequence |
|---|---|
| TelL-21 Lr1 | MDWTWILFLVAAATRVHSQGQDRHMIRMRQLIDIVDQLKNYVNDLVPEFLPAPEDVET NCEWSAFSCFQKAQLKSANTGNNERIINVSIKKLKRKPPSTNAGRRQKHRLTCPSCD SYEKKPPKEFLERFKSLLQKMIHQHLSSRTHGSEDSSGGGGSGGGGSGGGGSGGG GSGGGSLQIYIWAPLAGTCGVLLLSLVIT (SEQ ID NO: 24) |
| TelL-21 Lr2 | MDWTWILFLVAAATRVHSQGQDRHMIRMRQLIDIVDQLKNYVNDLVPEFLPAPEDVET NCEWSAFSCFQKAQLKSANTGNNERIINVSIKKLKRKPPSTNAGRRQKHRLTCPSCD SYEKKPPKEFLERFKSLLQKMIHQHLSSRTHGSEDSGSTSGSGKPGSGEGSTKGIYI WAPLAGTCGVLLLSLVIT (SEQ ID NO: 25) |
| TelL-21 Lr6 | MDWTWILFLVAAATRVHSQGQDRHMIRMRQLIDIVDQLKNYVNDLVPEFLPAPEDVET NCEWSAFSCFQKAQLKSANTGNNERIINVSIKKLKRKPPSTNAGRRQKHRLTCPSCD SYEKKPPKEFLERFKSLLQKMIHQHLSSRTHGSEDSGGGGSGGGGSGGGGSGGGG SGGGGSGGGGSGGGGSGGGGSGGGGSIYIWAPLAGTCGVLLLSLVIT (SEQ ID NO: 26) |
| TelL-21 Lr7 | MDWTWILFLVAAATRVHSQGQDRHMIRMRQLIDIVDQLKNYVNDLVPEFLPAPEDVET NCEWSAFSCFQKAQLKSANTGNNERIINVSIKKLKRKPPSTNAGRRQKHRLTCPSCD SYEKKPPKEFLERFKSLLQKMIHQHLSSRTHGSEDSAEAAAKEAAAKEAAAKEAAAKA LEAEAAAKEAAAKEAAAKEAAAKA IYIWAPLAGTCGVLLLSLVIT (SEQ ID NO: 27) |

TABLE 4-continued

| TeIL-21 Construct | Amino acid Sequence |
|---|---|
| TeIL-21 Lr8A1 | MDWTWILFLVAAATRVHSQGQDRHMIRMRQLIDIVDQLKNYVNDLVPEFLPAPEDVET NCEWSAFSCFQKAQLKSANTGNNERIINVSIKKLKRKPPSTNAGRRQKHRLTCPSCD SYEKKPPKEFLERFKSLLQKMIHQHLSSRTHGSEDSSGGGGSGGGGSGGGGSGGG GSGGGGSGGGGSGGGGSGGGGSGGGGSLQIYIWAPLAGTCGVLLLSLVIT (SEQ ID NO: 28) |
| TeIL-21 Lr9 | MDWTWILFLVAAATRVHSQGQDRHMIRMRQLIDIVDQLKNYVNDLVPEFLPAPEDVET NCEWSAFSCFQKAQLKSANTGNNERIINVSIKKLKRKPPSTNAGRRQKHRLTCPSCD SYEKKPPKEFLERFKSLLQKMIHQHLSSRTHGSEDSAGGGSGGGGSGGGGSGGGG SGGGGSGGGGSGGGGSGGGGSGGGGSGGGSGGGGSGGGGSASIYIWAPLAGTC GVLLLSLVIT (SEQ ID NO: 29) |
| TeIL-21 Lr8Ar2 | MDWTWILFLVAAATRVHSQGQDRHMIRMRQLIDIVDQLKNYVNDLVPEFLPAPEDVET NCEWSAFSCFQKAQLKSANTGNNERIINVSIKKLKRKPPSTNAGRRQKHRLTCPSCD SYEKKPPKEFLERFKSLLQKMIHQHLSSRTHGSEDSSGGGGSGGGGSGGGGSGGG GSGGGGSGGGGSGGGGSGGGGSGGGGSLQLLPSWAITLISVNGIFVICCLTYCFAP RCRERRRNERLRRESVRPV (SEQ ID NO: 30) |

Five tethered IL-21/tethered IL-15 (TeIL-21/15) constructs were prepared (TeIL-21/15 P2A Ar1, TeIL-21/15 E2A, TeIL-21/15 T2A, TeIL-21/15 FurinA-P2A, and TeIL-21/15 E2A Ar2). One TeIL-21 construct and one TeIL-15 construct were joined by a cleavable linker to generate each TeIL-21/15 construct (FIG. 1C). The nucleotide sequences of the TeIL-21/15 constructs were derived from their amino acid sequences and codon optimized for human tissue expression.

The TeIL-21 sequence, TeIL-15 sequence, and cleavable linker sequences of the TeIL-21/15 constructs are set forth in Table 5. In Table 5, the interleukin (IL15 or IL-21) amino acid sequence is underlined, and the anchor sequence (Ar1 or Ar2) is shown in bold.

TABLE 5

| Component | Amino acid Sequence |
|---|---|
| TeIL-21 Lr8A1 | MDWTWILFLVAAATRVHSQGQDRHMIRMRQLIDIVDQLKNYVNDLVPEFLPAPEDVET NCEWSAFSCFQKAQLKSANTGNNERIINVSIKKLKRKPPSTNAGRRQKHRLTCPSCD SYEKKPPKEFLERFKSLLQKMIHQHLSSRTHGSEDSSGGGGSGGGGSGGGGSGGG GSGGGGSGGGGSGGGGSGGGGSGGGGSLQIYIWAPLAGTCGVLLLSLVIT (SEQ ID NO: 28) |
| TeIL-21 Lr8Ar2 | MDWTWILFLVAAATRVHSQGQDRHMIRMRQLIDIVDQLKNYVNDLVPEFLPAPEDVET NCEWSAFSCFQKAQLKSANTGNNERIINVSIKKLKRKPPSTNAGRRQKHRLTCPSCD SYEKKPPKEFLERFKSLLQKMIHQHLSSRTHGSEDSSGGGGSGGGGSGGGGSGGG GSGGGGSGGGGSGGGGSGGGGSGGGGSLQLLPSWAITLISVNGIFVICCLTYCFAP RCRERRRNERLRRESVRPV (SEQ ID NO: 30) |
| TeIL-15 Lr1Ar2 | MDWTWILFLVAAATRVHSNWVNVISDLKKIEDLIQSMHIDATLYTESDVHPSCKVTAMK CFLLELQVISLESGDASIHDTVENLIILANNSLSSNGNVTESGCKECEELEEKNIKEFL QSFVHIVQMFINTSSGGGGSGGGGSGGGGSGGGGSGGGSLQLLPSWAITLISVNGI FVICCLTYCFAPRCRERRRNERLRRESVRPV (SEQ ID NO: 31) |
| Cleavable linker P2A | GSGATNFSLLKQAGDVEENPGP (SEQ ID NO: 7) |
| Cleavable linker E2A | GSGQCTNYALLKLAGDVESNPGP (SEQ ID NO: 8) |
| Cleavable linker T2A | GSGEGRGSLLTCGDVEENPGP (SEQ ID NO: 9) |
| Cleavable linker Furin-P2A | RAKRSGSGATNFSLLKQAGDVEENPGP (SEQ ID NO: 11) |

The amino acid sequences of the full TeIL-21/15 constructs are set forth in Table 6A. In Table 6A, the IL-21 sequence is underlined, the IL-15 sequence is shown in bold, and the anchor sequences (Ar1 or Ar2) are italicized. The cleavable linker is indicated in the left column of Table 6A.

TABLE 6A

| TeIL-21/15 Construct | Amino Acid Sequence |
|---|---|
| TeIL-21/15 P2A Ar1 | MDWTWILFLVAAATRVHSQGQDRHMIRMRQLIDIVDQLKNYVNDLVPEFLPAPEDVETN CEWSAFSCFQKAQLKSANTGNNERIINVSIKKLKRKPPSTNAGRRQKHRLTCPSCDSYE KKPPKEFLERFKSLLQKMIHQHLSSRTHGSEDSSGGGGSGGGGSGGGGSGGGGSGG GGSGGGGSGGGGSGGGGSGGGGSLQIYIWAPLAGTCGVLLLSLVITGSGATNFSLLKQ AGDVEENPGPMDWTWILFLVAAATRVHSNWVNVISDLKKIEDLIQSMHIDATLYTESDV HPSCKVTAMKCFLLELQVISLESGDASIHDTVENLIILANNSLSSNGNVTESGCKECEEL EEKNIKEFLQSFVHIVQMFINTSSGGGGSGGGGSGGGGSGGGGSGGGGSLQ*LLPSWAI TLISVNGIFVICCLTYCFAPRCRERRRNERLRRESVRPV* (SEQ ID NO: 32) |
| TeIL-21/15 E2A Ar1 | MDWTWILFLVAAATRVHSQGQDRHMIRMRQLIDIVDQLKNYVNDLVPEFLPAPEDVETN CEWSAFSCFQKAQLKSANTGNNERIINVSIKKLKRKPPSTNAGRRQKHRLTCPSCDSYE KKPPKEFLERFKSLLQKMIHQHLSSRTHGSEDSSGGGGSGGGGSGGGGSGGGGSGG GGSGGGGSGGGGSGGGGSGGGGSLQIYIWAPLAGTCGVLLLSLVITGSGQCTNYALL KLAGDVESNPGPMDWTWILFLVAAATRVHSNWVNVISDLKKIEDLIQSMHIDATLYTES DVHPSCKVTAMKCFLLELQVISLESGDASIHDTVENLIILANNSLSSNGNVTESGCKEC EELEEKNIKEFLQSFVHIVQMFINTSSGGGGSGGGGSGGGGSGGGGSGGGGSLQ*LLPS WAITLISVNGIFVICCLTYCFAPRCRERRRNERLRRESVRPV* (SEQ ID NO: 33) |
| TeIL-21/15 T2A | MDWTWILFLVAAATRVHSQGQDRHMIRMRQLIDIVDQLKNYVNDLVPEFLPAPEDVETN CEWSAFSCFQKAQLKSANTGNNERIINVSIKKLKRKPPSTNAGRRQKHRLTCPSCDSYE KKPPKEFLERFKSLLQKMIHQHLSSRTHGSEDSSGGGGSGGGGSGGGGSGGGGSGG GGSGGGGSGGGGSGGGGSGGGGSLQIYIWAPLAGTCGVLLLSLVITGSGEGRGSLLT CGDVEENPGPMDWTWILFLVAAATRVHSNWVNVISDLKKIEDLIQSMHIDATLYTESDV HPSCKVTAMKCFLLELQVISLESGDASIHDTVENLIILANNSLSSNGNVTESGCKECEEL EEKNIKEFLQSFVHIVQMFINTSSGGGGSGGGGSGGGGSGGGGSGGGGSLQ*LLPSWAI TLISVNGIFVICCLTYCFAPRCRERRRNERLRRESVRPV* (SEQ ID NO: 34) |
| TeIL-21/15 FurinA-P2A Ar1 | MDWTWILFLVAAATRVHSQGQDRHMIRMRQLIDIVDQLKNYVNDLVPEFLPAPEDVETN CEWSAFSCFQKAQLKSANTGNNERIINVSIKKLKRKPPSTNAGRRQKHRLTCPSCDSYE KKPPKEFLERFKSLLQKMIHQHLSSRTHGSEDSSGGGGSGGGGSGGGGSGGGGSGG GGSGGGGSGGGGSGGGGSGGGGSLQIYIWAPLAGTCGVLLLSLVITRAKRSGSGATN FSLLKQAGDVEENPGPMDWTWILFLVAAATRVHSNWVNVISDLKKIEDLIQSMHIDATL YTESDVHPSCKVTAMKCFLLELQVISLESGDASIHDTVENLIILANNSLSSNGNVTESGC KECEELEEKNIKEFLQSFVHIVQMFINTSSGGGGSGGGGSGGGGSGGGGSGGGGSLQ*L LPSWAITLISVNGIFVICCLTYCFAPRCRERRRNERLRRESVRPV* (SEQ ID NO: 35) |
| TeIL-21/15 E2A Ar2 | MDWTWILFLVAAATRVHSQGQDRHMIRMRQLIDIVDQLKNYVNDLVPEFLPAPEDVETN CEWSAFSCFQKAQLKSANTGNNERIINVSIKKLKRKPPSTNAGRRQKHRLTCPSCDSYE KKPPKEFLERFKSLLQKMIHQHLSSRTHGSEDSSGGGGSGGGGSGGGGSGGGGSGG GGSGGGGSGGGGSGGGGSGGGGSLQ*LLPSWAITLISVNGIFVICCLTYCFAPRCRERR RNERLRRESVRPV*GSGQCTNYALLKLAGDVESNPGPMDWTWILFLVAAATRVHSNWV NVISDLKKIEDLIQSMHIDATLYTESDVHPSCKVTAMKCFLLELQVISLESG-DASIHDTVE NLIILANNSLSSNGNVTESGCKECEELEEKNIKEFLQSFVHIVQMFINTSSGGGGSGGG GSGGGGSGGGGSGGGSLQ*LLPSWAITLISVNGIFVICCLTYCFAPRCRERRRNERLRRE SVRPV* (SEQ ID NO: 36) |
| TeIL-21/15 FurinA-P2A Ar2 | MDWTWILFLVAAATRVHSQGQDRHMIRMRQLIDIVDQLKNYVNDLVPEFLPAPEDVETN CEWSAFSCFQKAQLKSANTGNNERIINVSIKKLKRKPPSTNAGRRQKHRLTCPSCDSYE KKPPKEFLERFKSLLQKMIHQHLSSRTHGSEDSSGGGGSGGGGSGGGGSGGGGSGG GGSGGGGSGGGGSGGGGSGGGGSLQ*LLPSWAITLISVNGIFVICCLTYCFAPRCRERR RNERLRRESVRPV*RAKRSGSGATNFSLLKQAGDVEENPGPMDWTWILFLVAAATRVHS NWVNVISDLKKIEDLIQSMHIDATLYTESDVHPSCKVTAMKCFLLELQVISLESGDASIH DTVENLIILANNSLSSNGNVTESGCKECEELEEKNIKEFLQSFVHIVQMFINTSSGGGGS GGGGSGGGGSGGGGSGGGSLQ*LLPSWAITLISVNGIFVICCLTYCFAPRCRERRRNER LRRESVRPV* (SEQ ID NO: 37) |

TABLE 6B

| TeIL-21/15 P2A SEQ ID NO: 39 | ATGGATTGGACCTGGATTCTGTTCCTGGTGGCCGCTGCCACAAGAGTGCATAGCCAG GGCCAAGACCGGCACATGATCCGGATGAGACAGCTGATCGACATCGTGGACCAGCTG AAGAACTACGTGAACGACCTGGTGCCTGAGTTCCTGCCTGCTCCTGAGGACGTGGAA ACAAATTGCGAGTGGTCCGCCTTCAGCTGCTTCCAGAAGGCCCAGCTGAAAAGCGCC AACACCGGCAACAACGAGCGGATCATCAACGTGTCCATCAAGAAGCTGAAGCGGAA GCCTCCTAGCACCAATGCCGGAAGAAGGCAGAAGCACAGACTGACCTGTCCTAGCTG CGACAGCTACGAGAAGAAGCCTCCAAAAGAGTTCCTGGAACGGTTCAAGAGCCTGCT GCAGAAGATGATCCACCAGCACCTGAGCAGCAGAACCCACGGCTCTGAAGATTCTAG |

TABLE 6B-continued

| | |
|---|---|
| | CGGAGGCGGAGGAAGTGGTGGCGGAGGTTCTGGTGGCGGTGGATCAGGCGGTGGCG<br>GATCTGGCGGCGAGGCAGTGGCGGAGGTGGAAGCGGTGGTGGTGGCTCTGGCGGA<br>GGCGGTAGCGGCGGAGGCGGATCTCTTCAGATCTATATTTGGGCCCCTCTGGCCGGA<br>ACATGTGGCGTGTTGCTGCTGTCTCTGGTTATCACCGGCAGCGGCGCCACAAATTTCA<br>GCCTGCTGAAACAGGCCGGCGACGTGGAAGAGAATCCTGGACCTATGGACTGGACTT<br>GGATACTCTTTCTGGTCGCTGCCGCCACACGGGTGCACTCTAATTGGGTCAACGTGAT<br>CAGCGACCTGAAGAAGATCGAGGACCTGATCCAGAGCATGCACATCGACGCCACACT<br>GTACACCGAGTCCGATGTGCACCCTAGCTGCAAAGTGACCGCCATGAAGTGCTTTCTG<br>CTGGAACTGCAAGTGATCAGCCTGGAAAGCGGCGACGCCAGCATCCACGATACCGTG<br>GAAAATCTGATCATCCTGGCCAACAACAGCCTGTCCAGCAACGGCAATGTGACCGAG<br>AGCGGCTGCAAAGAGTGCGAGGAACTGGAAGAGAAGAACATCAAAGAGTTTCTGCA<br>GAGCTTCGTCCACATCGTGCAGATGTTCATCAACACCTCATCAGGCGGCGGTGGTAGT<br>GGAGGCGGAGGCTCAGGCGGCGGAGGTTCCGGAGGTGGCGGTTCCGGCGGAGGATC<br>TCTTCAATTGCTGCCTAGCTGGGCCATCACACTGATCTCCGTGAACGGCATCTTCGTG<br>ATCTGCTGCCTGACCTACTGCTTCGCCCCTAGATGCAGAGAGCGGAGAAGAAACGAG<br>CGGCTGAGAAGAGAAAGCGTGCGGCCTGTG |
| TeIL-21/15<br>E2A Ar1<br>SEQ ID<br>NO: 40 | ATGGATTGGACCTGGATTCTGTTCCTGGTGGCCGCTGCCACAAGAGTGCATAGCCAG<br>GGCCAAGACCGGCACATGATCCGGATGAGACAGCTGATCGACATCGTGGACCAGCTG<br>AAGAACTACGTGAACGACCTGGTGCCTGAGTTCCTGCCTGCTCCTGAGGACGTGGAA<br>ACAAATTGCGAGTGGTCCGCCTTCAGCTGCTTCCAGAAGGCCCAGCTGAAAAGCGCC<br>AACACCGGCAACAACGAGCGGATCATCAACGTGTCCATCAAGAAGCTGAAGCGGAA<br>GCCTCCTAGCACCAATGCCGGAAGAAGGCAGAAGCACAGACTGACCTGTCCTAGCTG<br>CGACAGCTACGAGAAGAAGCCTCCAAAAGAGTTCCTGGAACGGTTCAAGAGCCTGCT<br>GCAGAAGATGATCCACCAGCACCTGAGCAGCAGAACCCACGGCTCTGAAGATTCTAG<br>CGGAGGCGGAGGAAGTGGTGGCGGAGGTTCTGGTGGCGGTGGATCAGGCGGTGGCG<br>GATCTGGCGGCGAGGCAGTGGCGGAGGTGGAAGCGGTGGTGGTGGCTCTGGCGGA<br>GGCGGTAGCGGCGGAGGCGGATCTCTTCAGATCTATATTTGGGCCCCTCTGGCCGGA<br>ACATGTGGCGTGTTGCTGCTGTCTCTGGTTATCACCGGCTCCGGCCAGTGTACCAATT<br>ACGCCCTGCTTAAACTGGCCGGCGACGTGGAATCCAATCCTGGACCTATGGACTGGA<br>CTTGGATACTCTTTCTGGTCGCTGCCGCCACACGGGTGCACTCTAATTGGGTCAACGT<br>GATCAGCGACCTGAAGAAGATCGAGGACCTGATCCAGAGCATGCACATCGACGCCAC<br>ACTGTACACCGAGTCCGATGTGCACCCTAGCTGCAAAGTGACCGCCATGAAGTGCTTT<br>CTGCTGGAACTGCAAGTGATCAGCCTGGAAAGCGGCGACGCCAGCATCCACGATACC<br>GTGGAAAATCTGATCATCCTGGCCAACAACAGCCTGTCCAGCAACGGCAATGTGACC<br>GAGAGCGGCTGCAAAGAGTGCGAGGAACTGGAAGAGAAGAACATCAAAGAGTTTCT<br>GCAGAGCTTCGTCCACATCGTGCAGATGTTCATCAACACCTCATCAGGCGGCGGTGGT<br>AGTGGAGGCGGAGGCTCAGGCGGCGGAGGTTCCGGAGGTGGCGGTTCCGGCGGAGG<br>ATCTCTTCAATTGCTGCCTAGCTGGGCCATCACACTGATCTCCGTGAACGGCATCTTC<br>GTGATCTGCTGCCTGACCTACTGCTTCGCCCCTAGATGCAGAGAGCGGAGAAGAAAC<br>GAGCGGCTGAGAAGAGAAAGCGTGCGGCCTGTG |
| TeIL-21/15<br>T2A<br>SEQ ID<br>NO: 41 | ATGGATTGGACCTGGATTCTGTTCCTGGTGGCCGCTGCCACAAGAGTGCATAGCCAG<br>GGCCAAGACCGGCACATGATCCGGATGAGACAGCTGATCGACATCGTGGACCAGCTG<br>AAGAACTACGTGAACGACCTGGTGCCTGAGTTCCTGCCTGCTCCTGAGGACGTGGAA<br>ACAAATTGCGAGTGGTCCGCCTTCAGCTGCTTCCAGAAGGCCCAGCTGAAAAGCGCC<br>AACACCGGCAACAACGAGCGGATCATCAACGTGTCCATCAAGAAGCTGAAGCGGAA<br>GCCTCCTAGCACCAATGCCGGAAGAAGGCAGAAGCACAGACTGACCTGTCCTAGCTG<br>CGACAGCTACGAGAAGAAGCCTCCAAAAGAGTTCCTGGAACGGTTCAAGAGCCTGCT<br>GCAGAAGATGATCCACCAGCACCTGAGCAGCAGAACCCACGGCTCTGAAGATTCTAG<br>CGGAGGCGGAGGAAGTGGTGGCGGAGGTTCTGGTGGCGGTGGATCAGGCGGTGGCG<br>GATCTGGCGGCGAGGCAGTGGCGGAGGTGGAAGCGGTGGTGGTGGCTCTGGCGGA<br>GGCGGTAGCGGCGGAGGCGGATCTCTTCAGATCTATATTTGGGCCCCTCTGGCCGGA<br>ACATGTGGCGTGTTGCTGCTGTCTCTGGTTATCACCGGTTCTGGCGAAGGCAGAGGCT<br>CTCTGCTTACTTGTGGCGACGTGGAAGAGAATCCTGGACCTATGGACTGGACTTGGAT<br>ACTCTTTCTGGTCGCTGCCGCCACACGGGTGCACTCTAATTGGGTCAACGTGATCAGC<br>GACCTGAAGAAGATCGAGGACCTGATCCAGAGCATGCACATCGACGCCACACTGTAC<br>ACCGAGTCCGATGTGCACCCTAGCTGCAAAGTGACCGCCATGAAGTGCTTTCTGCTGG<br>AACTGCAAGTGATCAGCCTGGAAAGCGGCGACGCCAGCATCCACGATACCGTGGAAA<br>ATCTGATCATCCTGGCCAACAACAGCCTGTCCAGCAACGGCAATGTGACCGAGAGCG<br>GCTGCAAAGAGTGCGAGGAACTGGAAGAGAAGAACATCAAAGAGTTTCTGCAGAGC<br>TTCGTCCACATCGTGCAGATGTTCATCAACACCTCATCAGGCGGCGGTGGTAGTGGAG<br>GCGGAGGCTCAGGCGGCGGAGGTTCCGGAGGTGGCGGTTCCGGCGGAGGATCTCTTC<br>AATTGCTGCCTAGCTGGGCCATCACACTGATCTCCGTGAACGGCATCTTCGTGATCTG<br>CTGCCTGACCTACTGCTTCGCCCCTAGATGCAGAGAGCGGAGAAGAAACGAGCGGCT<br>GAGAAGAGAAAGCGTGCGGCCTGTG |
| TeIL-21/15<br>FurinA-P2A<br>Ar1<br>SEQ ID<br>NO: 42 | ATGGATTGGACCTGGATTCTGTTCCTGGTGGCCGCTGCCACAAGAGTGCATAGCCAG<br>GGCCAAGACCGGCACATGATCCGGATGAGACAGCTGATCGACATCGTGGACCAGCTG<br>AAGAACTACGTGAACGACCTGGTGCCTGAGTTCCTGCCTGCTCCTGAGGACGTGGAA<br>ACAAATTGCGAGTGGTCCGCCTTCAGCTGCTTCCAGAAGGCCCAGCTGAAAAGCGCC<br>AACACCGGCAACAACGAGCGGATCATCAACGTGTCCATCAAGAAGCTGAAGCGGAA<br>GCCTCCTAGCACCAATGCCGGAAGAAGGCAGAAGCACAGACTGACCTGTCCTAGCTG<br>CGACAGCTACGAGAAGAAGCCTCCAAAAGAGTTCCTGGAACGGTTCAAGAGCCTGCT<br>GCAGAAGATGATCCACCAGCACCTGAGCAGCAGAACCCACGGCTCTGAAGATTCTAG<br>CGGAGGCGGAGGAAGTGGTGGCGGAGGTTCTGGTGGCGGTGGATCAGGCGGTGGCG<br>GATCTGGCGGCGAGGCAGTGGCGGAGGTGGAAGCGGTGGTGGTGGCTCTGGCGGA<br>GGCGGTAGCGGCGGAGGCGGATCTCTTCAGATCTATATTTGGGCCCCTCTGGCCGGA<br>ACATGTGGCGTGTTGCTGCTGTCTCTGGTTATCACCAGGGCCAAAGAAGCGGCAGC<br>GGCGCCACAAATTTCAGCCTGCTGAAACAGGCCGGCGACGTGGAAGAGAATCCTGGA |

TABLE 6B-continued

| | |
|---|---|
| | CCTATGGACTGGACTTGGATACTCTTTCTGGTCGCTGCCGCCACACGGGTGCACTCTA<br>ATTGGGTCAACGTGATCAGCGACCTGAAGAAGATCGAGGACCTGATCCAGAGCATGC<br>ACATCGACGCCACACTGTACACCGAGTCCGATGTGCACCCTAGCTGCAAAGTGACCG<br>CCATGAAGTGCTTTCTGCTGGAACTGCAAGTGATCAGCCTGGAAAGCGGCGACGCCA<br>GCATCCACGATACCGTGGAAAATCTGATCATCCTGGCCAACAACAGCCTGTCCAGCA<br>ACGGCAATGTGACCGAGAGCGGCTGCAAAGAGTGCGAGGAACTGGAAGAGAAGAAC<br>ATCAAAGAGTTTCTGCAGAGCTTCGTCCACATCGTGCAGATGTTCATCAACACCTCAT<br>CAGGCGGCGGTGGTAGTGGAGGCGGAGGCTCAGGCGGCGGAGGTTCCGGAGGTGGC<br>GGTTCCGGCGGAGGATCTCTTCAATTGCTGCCTAGCTGGGCCATCACACTGATCTCCG<br>TGAACGGCATCTTCGTGATCTGCTGCCTGACCTACTGCTTCGCCCCTAGATGCAGAGA<br>GCGGAGAAGAAACGAGCGGCTGAGAAGAGAAAGCGTGCGGCCTGTG |
| TeIL-21/15<br>E2A Ar2<br>SEQ ID<br>NO: 43 | ATGGATTGGACCTGGATTCTGTTCCTGGTGGCCGCTGCCACAAGAGTGCATAGCCAG<br>GGCCAAGACCGGCACATGATCCGGATGAGACAGCTGATCGACATCGTGGACCAGCTG<br>AAGAACTACGTGAACGACCTGGTGCCTGAGTTCCTGCCTGCTCCTGAGGACGTGGAA<br>ACAAATTGCGAGTGGTCCGCCTTCAGCTGCTTCCAGAAGGCCCAGCTGAAAAGCGCC<br>AACACCGGCAACAACGAGCGGATCATCAACGTGTCCATCAAGAAGCTGAAGCGGAA<br>GCCTCCTAGCACCAATGCCGGAAGAAGGCAGAAGCACAGACTGACCTGTCCTAGCTG<br>CGACAGCTACGAGAAGAAGCCTCCAAAAGAGTTCCTGGAACGGTTCAAGAGCCTGCT<br>GCAGAAGATGATCCACCAGCACCTGAGCAGCAGAACCCACGGCTCTGAAGATTCTAG<br>CGGAGGCGGAGGAAGTGGTGGCGGAGGTTCTGGTGGCGGTGGATCAGGCGGTGGCG<br>GATCTGGCGGCGGAGGCAGTGGCGGAGGTGGAAGCGGTGGTGGTGGCTCTGGCGGA<br>GGCGGTAGCGGCGGAGGCGGATCTCTTCAATTGCTGCCTAGCTGGGCCATCACACTG<br>ATCTCCGTGAACGGCATCTTCGTGATCTGCTGCCTGACCTACTGCTTCGCCCCTAGAT<br>GCAGAGAGCGGAGAAGAAACGAGCGGCTGAGAAGAGAATCTGTGCGGCCTGTTGGC<br>TCCGCCAGTGTACAAATTATGCCCTGCTGAAGCTGGCCGGCGACGTGGAATCTAAT<br>CCTGGACCTATGGACTGGACTTGGATACTCTTTCTGGTCGCTGCCGCCACACGGGTGC<br>ACTCTAATTGGGTCAACGTGATCAGCGACCTGAAGAAGATCGAGGACCTGATCCAGA<br>GCATGCACATCGACGCCACACTGTACACCGAGTCCGATGTGCACCCTAGCTGCAAAG<br>TGACCGCCATGAAGTGCTTTCTGCTGGAACTGCAAGTGATCAGCCTGGAAAGCGGCG<br>ACGCCAGCATCCACGATACCGTGGAAAATCTGATCATCCTGGCCAACAACAGCCTGT<br>CCAGCAACGGCAATGTGACCGAGAGCGGCTGCAAAGAGTGCGAGGAACTGGAAGAA<br>AAGAACATCAAAGAGTTTCTGCAGAGCTTCGTCCACATCGTGCAGATGTTCATCAAC<br>ACCTCATCAGGTGGCGGTGGAAGCGGAGGTGGCGGTAGTGGCGGCGGAGGCTCAGG<br>CGGCGGAGGTTCCGGCGGAGGATCTCTTCAGCTCCTGCCATCTTGGGCTATCACCCTG<br>ATTAGTGTGAATGGGATCTTTGTCATCTGTTGTCTCACGTACTGTTTCGCTCCCCGGTG<br>CAGAGAGAGAAGGCGCAACGAAAGACTGCGGAGAGAAAGCGTCAGACCCGTG |
| TeIL-21/15<br>Furin-P2A Ar2<br>SEQ ID<br>NO: 44 | ATGGATTGGACCTGGATTCTGTTCCTGGTGGCCGCTGCCACAAGAGTGCATAGCCAG<br>GGCCAAGACCGGCACATGATCCGGATGAGACAGCTGATCGACATCGTGGACCAGCTG<br>AAGAACTACGTGAACGACCTGGTGCCTGAGTTCCTGCCTGCTCCTGAGGACGTGGAA<br>ACAAATTGCGAGTGGTCCGCCTTCAGCTGCTTCCAGAAGGCCCAGCTGAAAAGCGCC<br>AACACCGGCAACAACGAGCGGATCATCAACGTGTCCATCAAGAAGCTGAAGCGGAA<br>GCCTCCTAGCACCAATGCCGGAAGAAGGCAGAAGCACAGACTGACCTGTCCTAGCTG<br>CGACAGCTACGAGAAGAAGCCTCCAAAAGAGTTCCTGGAACGGTTCAAGAGCCTGCT<br>GCAGAAGATGATCCACCAGCACCTGAGCAGCAGAACCCACGGCTCTGAAGATTCTAG<br>CGGAGGCGGAGGAAGTGGTGGCGGAGGTTCTGGTGGCGGTGGATCAGGCGGTGGCG<br>GATCTGGCGGCGAGGCAGTGGCGGAGGTGGAAGCGGTGGTGGTGGCTCTGGCGGA<br>GGCGGTAGCGGCGGAGGCGGATCTCTTCAATTGCTGCCTAGCTGGGCCATCACACTG<br>ATCTCCGTGAACGGCATCTTCGTGATCTGCTGCCTGACCTACTGCTTCGCCCCTAGAT<br>GCAGAGAGCGGAGAAGAAACGAGCGGCTGAGAAGAGAATCTGTGCGGCCTGTTAGA<br>GCCAAGAGATCTGGAAGCGGCGCCACCAACTTTAGCCTGCTGAAACAGGCTGGCGAC<br>GTGGAAGAGAACCCTGGACCTATGGACTGGACTTGGATACTCTTTCTGGTCGCTGCCG<br>CCACACGGGTGCACTCTAATTGGGTCAACGTGATCAGCGACCTGAAGAAGATCGAGG<br>ACCTGATCCAGAGCATGCACATCGACGCCACACTGTACACCGAGTCCGATGTGCACC<br>CTAGCTGCAAAGTGACCGCCATGAAGTGCTTTCTGCTGGAACTGCAAGTGATCAGCCT<br>GGAAAGCGGCGACGCCAGCATCCACGATACCGTGGAAAATCTGATCATCCTGGCCAA<br>CAACAGCCTGTCCAGCAACGGCAATGTGACCGAGAGCGGCTGCAAAGAGTGCGAGG<br>AACTGGAAGAAAAGAACATCAAAGAGTTTCTGCAGAGCTTCGTCCACATCGTGCAGA<br>TGTTCATCAACACCTCATCAGGTGGCGGTGGAAGCGGAGGTGGCGGTAGTGGCGGCG<br>GAGGCTCAGGCGGCGGAGGTTCCGGCGGAGGATCTCTTCAGCTCCTGCCATCTTGGG<br>CTATCACCCTGATTAGTGTGAATGGGATCTTTGTCATCTGTTGTCTCACGTACTGTTTC<br>GCTCCCCGGTGCAGAGAGAGAAGGCGCAACGAAAGACTGCGGAGAGAAAGCGTCAG<br>ACCCGTG |

Virus Preparation and T Cell Transduction

Human peripheral blood mononuclear cells (PBMCs) were isolated from the buffy coats. Before transduction, PBMCs were cultured in T cell media plus 50 ng/mL anti-CD3 (OKT3, Miltenyi Biotech, Bergisch Gladbach, Germany) for two days. Lentiviral supernatants were generated by cotransfection of 293T cells with TeIL-15 vectors and the packaging plasmids (pREV/RSV, pMD.2, pRRE/LG). Two days after transfection, lentiviral supernatants were harvested. Transduction was performed by adding 5 ml lentiviral supernatant to 1 million T cells in the presence of protamine sulfate (10 μg/ml). On the following day, T cells were harvested and cultured in normal T cell media. Retroviral supernatants were generated by cotransfection of 293GP cells with tethered cytokine vectors and RD114 packaging plasmids. Two days after transfection, retroviral supernatants were harvested. Transduction was performed by adding 5 ml retroviral supernatant to one well of a six-well plate coated with RETRONECTIN recombinant human fibronectin fragment (Lonza, Basel, Switzerland) and centrifuged at 2000 g for 2 hours at 32° C. The retroviral supernatant was discarded, and 1 million T cells were added. On the following day, T cells were harvested and cultured in normal conditions.

T Cell Proliferation and Viability

T cells transduced with different constructs were plated at the same concentration on day 0 when exogenous IL-2 was removed from the culture media. Live cell numbers were assessed by trypan blue assay using a CELLOMETER cell counter machine (Nexcelom, Lawrence, MA).

Flow Cytometry

To detect TeIL-21 in transduced cells, phycoerythrin (PE)-, or allophycocyanin (APC)-conjugated antibodies against IL-21 (Biolegend (San Diego, CA), or BD Biosciences (Franklin Lakes, NJ)) were used to label cells. To detect TeIL-15, biotin-conjugated IL-15 (R&D Systems, Minneapolis, MN) plus streptavidin-ALEXA FLUOR 647 dye or streptavidin-ALEXA FLUOR 488 dye (Thermo Fischer Scientific, Waltham, MA) were used to label transduced cells. Data were acquired with a BD FORTESSA or LSRII flow cytometer (BD Biosciences) and analyzed with FLOWJO software (FlowJo, LLC, Ashland, OR).

Treatment of Established Tumors in NSG Mice

Animal research protocols were approved by the NIH Animal Care and Use Committee. NOD scid gamma (NSG) mice (The Jackson Laboratory, Bar Harbor, ME) with established human cervical cancer tumors were treated by tail vein injection of human T cells. Tumors were initiated by subcutaneous injection of 1×10$^6$ CaSki tumor cells. T cell infusion was performed on day 12 following tumor cell injection by a single intravenous injection. Tumor size was determined by caliper measurement of the perpendicular diameters of each tumor and was reported as tumor area.

Example 1

This example demonstrates that cells transduced with TeIL-15 Lr1 exhibit superior proliferation in the absence of exogenous IL-2 as compared to the other IL-15 constructs of Table 2.

PBMCs were cultured in AIM V media supplemented with IL-2 (300 IU/mL) and anti-CD3 antibody (OKT3, 50 ng/mL) for 2 days. Then the cells were transduced with lentivirus containing the TeIL-15 Lr1, TeIL-15 Lr2, IL-15 RA, TeIL-15 Lr6, or IL-15S construct of Table 2. The same number of cells that were transduced with each IL-15 construct was plated on day 0 (FIG. 2) when IL-2 was withdrawn from the media on day 7 after transduction. Proliferation of transduced cells was evaluated by assessing the total number of live cells using a trypan blue assay at each of the different time points shown in FIG. 2. Untransduced cells served as a negative control. Untransduced cells cultured in the presence of exogenous IL-15 served as a positive control.

The results are shown in FIG. 2. As shown in FIG. 2, T cells transduced with TeIL-15 Lr1 construct showed better proliferation than the other constructs in the absence of exogenous IL-2.

Example 2

This example demonstrates that cells transduced with the TeIL-15 Lr1 construct displayed the highest expression level of IL-15 on the cell surface as compared to cells transduced with the TeIL-15 Lr2, IL-15 RA, or IL-15S construct.

PBMC were transduced with a lentivirus containing the TeIL-15 Lr1, TeIL-15 Lr2, IL-15 RA, or IL-15S construct of Table 2 as described in Example 1. The presence of expressed IL-15 on the cell membrane was analyzed by flow cytometry. Cells transduced with the TeIL-15 Lr1 construct displayed the highest expression level of IL-15 (62.3%) on the cell membrane as compared to cells transduced with the TeIL-15 Lr2 (53.2%), IL-15 RA (23.5%), or IL-15S (33.2%) construct.

Example 3

This example demonstrates that 293T cells transduced with the TeIL-21 Lr6, TeIL-21 Lr1, or TeIL-21 Lr2 construct of Table 4 expressed IL-21 on the cell surface. Cells (293T) were transduced with a lentivirus containing the TeIL-21 Lr7, TeIL-21 Lr6, TeIL-21 Lr1, or TeIL-21 Lr2 construct of Table 4. Unstained cells and stained but untransduced cells served as negative controls.

TeIL-21 expression was analyzed by flow cytometry. The results are shown in Table 7. As shown in Table 7, more than 30% of the 293T cells transduced with TeIL-21 Lr6, TeIL-21 Lr1, or TeIL-21 Lr2 expressed IL-21.

TABLE 7

|  | Quadrant (Q1) FITC-A$^+$IL-21$^-$ | Q2 FITC-A$^+$IL-21$^+$ | Q3 FITC-A$^-$IL-21$^+$ | Q4 FITC-A$^-$IL-21$^-$ |
| --- | --- | --- | --- | --- |
| Unstained | 0.000 | 0.026 | 0.100 | 99.900 |
| Untransduced | 0.014 | 0.000 | 0.250 | 99.700 |
| TeIL-21 Lr1 | 0.000 | 0.086 | 37.300 | 62.700 |
| TeIL-21 Lr2 | 0.000 | 0.028 | 36.500 | 63.400 |
| TeIL-21 Lr6 | 0.000 | 0.041 | 30.100 | 69.900 |
| TeIL-21 Lr7 | 0.000 | 0.110 | 9.710 | 90.200 |

Example 4

This example demonstrates that human T cells transduced with a lentivirus containing the TeIL-21 Lr6 construct of Table 4 showed the highest expression level of IL-21 as compared to cells transduced with the TeIL-21 Lr1 or TeIL-21 Lr2 construct.

Human T cells were transduced with a lentivirus containing the TeIL-21 Lr6, TeIL-21 Lr1, or TeIL-21 Lr2 construct of Table 4. Unstained cells and stained but untransduced cells served as negative controls.

TeIL-21 expression was analyzed by flow cytometry. The results are shown in Table 8. As shown in Table 8, cells transduced with TeIL-21 Lr6 showed the highest expression level of IL-21.

TABLE 8

|  | Q1 PE-A$^+$IL-21$^-$ | Q2 PE-A$^+$IL-21$^+$ | Q3 PE-A$^-$IL-21$^+$ | Q4 PE-A$^-$IL-21$^-$ |
| --- | --- | --- | --- | --- |
| Unstained | 0.00 | 0.00 | 0.15 | 99.90 |
| Untransduced | 0.00 | 0.00 | 0.44 | 99.60 |
| TeIL-21 Lr1 | 0.00 | 0.00 | 25.40 | 74.60 |
| TeIL-21 Lr2 | 0.00 | 0.00 | 16.90 | 83.10 |
| TeIL-21 Lr6 | 0.00 | 0.00 | 53.30 | 46.70 |

Example 5

This example demonstrates that human T cells transduced with a retrovirus containing the TeIL-21 Lr8Ar1 construct of Table 4 showed the highest expression level of IL-21 as compared to the TeIL-21 Lr6 or TeIL-21 Lr9 construct.

Human T cells were transduced with a retrovirus containing the TeIL-21 Lr6, TeIL-21 Lr8Ar1, or TeIL-21 Lr9 construct of Table 4. Stained but untransduced cells served as a negative control.

TeIL-21 expression was analyzed by flow cytometry. The results are shown in Table 9. As shown in Table 9, cells transduced with TeIL-21 Lr8Ar1 showed the highest expression level of IL-21.

TABLE 9

|  | Q1<br>FITC-A$^+$IL-21$^-$ | Q2<br>FITC-A$^+$IL-21$^+$ | Q3<br>FITC-A$^-$IL-21$^+$ | Q4<br>FITC-A$^-$IL-21$^-$ |
|---|---|---|---|---|
| Untransduced | 0.000 | 0.000 | 1.190 | 98.800 |
| TeIL-21 Lr6 | 0.000 | 0.056 | 64.100 | 35.800 |
| TeIL-21 Lr8Ar1 | 0.000 | 0.180 | 69.400 | 30.400 |
| TeIL-21 Lr9 | 0.000 | 0.350 | 66.400 | 33.300 |

Example 6

This example demonstrates that human T cells transduced with a retrovirus containing the TeIL-21 Lr8Ar2 construct of Table 4 showed the highest expression level of IL-21 as compared to the TeIL-21 Lr8Ar1 construct.

Human T cells were transduced with a retrovirus containing the TeIL-21 Lr8Ar1 or TeIL-21 Lr8Ar2 construct of Table 4.

TeIL-21 expression was analyzed by flow cytometry. The percentage of cells with the indicated phenotype are shown in Table 10. Although the percentage of cells expressing IL-21 in Table 10 was slightly higher for TeIL-21 Lr8Ar1 as compared to TeIL-21 Lr8Ar2, the MFI (mean fluorescence intensity) of TeIL-21 Lr8Ar2 was observed to be higher than that of TeIL-21 Lr8Ar1, which indicates that the protein expression level of IL-21 was higher with TeIL-21 Lr8Ar2. Accordingly, it was concluded that cells transduced with TeIL-21 Lr8Ar2 showed higher expression of IL-21 as compared to TeIL-21 Lr8Ar1.

TABLE 10

|  | Q1<br>FITC-A$^+$IL-21$^-$ | Q2<br>FITC-A$^+$IL-21$^+$ | Q3<br>FITC-A$^-$IL-21$^+$ | Q4<br>FITC-A$^-$IL-21$^-$ |
|---|---|---|---|---|
| TeIL-21 Lr8Ar1 | 0.019 | 0.390 | 90.200 | 9.360 |
| TeIL-21 Lr8Ar2 | 0.000 | 0.520 | 89.100 | 10.300 |

Example 7

This example demonstrates that human T cells transduced with a retrovirus containing the TeIL-21/15 E2A Ar1 showed higher expression of TeIL-21/15 as compared to TeIL-21/15 P2A, TeIL-21/15 T2A, or TeIL-21/15 FurinA-P2A.

Human T cells were transduced with a retrovirus containing the TeIL-21/15 E2A Ar1, TeIL-21/15 P2A, TeIL-21/15 T2A, or TeIL-21/15 FurinA-P2A construct of Table 6. Untransduced cells served as a negative control. Human T cells transduced with a retrovirus containing the TeIL-15 Lr1Ar2 construct (Table 5) alone or the TeIL-21 Lr8Ar1 construct (Table 5) alone served as controls. As another control, human T cells were co-transduced with separate TeIL-15 Lr1Ar2 (Table 5) and TeIL-21 Lr8Ar1 constructs.

TeIL-21 expression was analyzed by flow cytometry. The results are shown in Table 11. As shown in Table 11, cells transduced with TeIL-21/15 T2A showed lower expression of TeIL-21/15 as compared to TeIL-21/15 P2A, TeIL-21/15 E2A Ar1, or TeIL-21/15 FurinA-P2A.

TABLE 11

|  | Q1 IL-21$^+$IL-15$^-$ | Q2 IL-21$^+$IL-15$^+$ | Q3 IL-21$^-$IL-15$^+$ | Q4 IL-21$^-$IL-15$^-$ |
|---|---|---|---|---|
| Untransduced | 0.097 | 0.650 | 0.840 | 98.400 |
| TeIL-15 Lr1Ar2 alone | 0.510 | 7.050 | 73.100 | 19.400 |
| TeIL-21 Lr8 Ar1 alone | 82.700 | 5.210 | 0.230 | 11.900 |
| co-transduced with TeIL-15 Lr1Ar2 and TeIL-21 Lr8 Ar1 | 8.290 | 73.800 | 2.600 | 15.300 |
| TeIL-21/15 E2A Ar1 | 3.820 | 74.100 | 1.840 | 20.300 |
| TeIL-21/15 P2A | 2.850 | 73.300 | 3.740 | 20.100 |
| TeIL-21/15 T2A | 0.970 | 33.900 | 34.500 | 30.700 |
| TeIL-21/15 FurinA-P2A | 2.660 | 76.200 | 3.030 | 18.100 |

Example 8

This example demonstrates that administering T cells co-transduced with the E7 TCR and TeIL-21/15 to tumor-bearing mice results in the complete regression of tumor.

NSG mice were subcutaneously inoculated with 1×10$^6$ CaSki cervical tumor cells. CaSki tumor cells are HPV 16 E7 positive and MART-1 negative. Two weeks later, the mice with established tumors were treated with a single intravenous injection of 10 million untransduced or transduced T cells in a volume of 0.5 ml in Hank's balanced salt solution (HBSS). T cells were transduced with an anti-MART-1 TCR (DMF5) alone or the anti-HPV 16 E7 TCR (E7) alone or were co-transduced with one of (i)-(vi) as follows:
  (i) DMF5 TCR and TeIL-15 Lr1Ar2,
  (ii) DMF5 TCR and TeIL-21 Lr8Ar1,
  (iii) DMF5 TCR and TeIL-21/15 E2A Ar1,
  (iv) E7 TCR and TeIL-15 Lr1Ar2,
  (v) E7 TCR and TeIL-21 Lr8Ar1, or
  (vi) E7 TCR and TeIL-21/15 E2A Ar1.

Tumor size was measured using digital caliper every 3-4 days. The results are shown in FIG. 3. The tumor growth curve of each of the individual mice assessed in FIG. 3 is shown in FIGS. 4A-4I.

The complete regression of tumor was observed in four of five mice receiving T cells co-transduced with E7 TCR and TeIL-21/15 (FIG. 4E) and in two of five mice receiving T cells co-transduced with E7 TCR and TeIL-21 (FIG. 4D). The mice receiving T cells transduced with E7 TCR (FIG. 4B) or T cells co-transduced with E7 TCR and TeIL-15 (FIG. 4C) only showed delayed tumor progression. Mice receiving T cells transduced with irrelevant TCR (DMF5 TCR) (FIG. 4F), DMF5 TCR and TeIL-15 (FIG. 4G), DMF5 TCR and TeIL-21 (FIG. 4H), or DMF5 TCR and TeIL-21/15 (FIG. 4I) demonstrated similar tumor growth curve as control mice receiving no treatment (FIG. 4A).

Example 9

This example demonstrates the growth curve of T cells transduced with TeIL-21/15 FurinA-P2A Ar2 in vitro.

T cells from 20 healthy donors were transduced with TeIL-21/15 FurinA-P2A Ar2 or secreted IL-21/15 (sIL-21/15), which served as a control. The exogenous T cell growth factor, IL-2, was withdrawn from the culture media on day 7 after transduction. Viable cells were counted at various time points after IL-2 withdrawal to evaluate the survival of the transduced T cells.

The growth curves of the transduced T cells from each healthy donor are shown in FIGS. 5A-5T. As shown in FIGS. 5A-5T, TeIL-21/15 FurinA-P2A Ar2-transduced T cells from 18 out of 20 healthy donors died six weeks after IL-2 was withdrawn, suggesting that constitutive IL-15 and IL-21 signaling does not transform the target T cells into an immortal cell line.

Example 10

This example demonstrates that T cells transduced with TeIL-21/15 FurinA-P2A Ar2 shed less IL-15 and IL-21 in vitro as compared to T cells transduced with secreted IL-21/15.

T cells from a healthy donor were transduced with one of (i)-(v), as follows:
- (i.) E7 TCR and TeIL-15 Lr1Ar2,
- (ii.) E7 TCR and TeIL-21 Lr8Ar2,
- (iii.) E7 TCR and TeIL-21/15 FurinA-P2A Ar2,
- (iv.) E7 TCR and secreted IL-21/15 (sIL-21/15) (served as positive control for assay development), or
- (v.) E7 TCR alone (control).

Untransduced T cells from the healthy donor also served as a control. The transduced cells were cultured for seven days. T cells were harvested and seeded in fresh media with equal numbers or co-cultured with tumor cells at a one-to-one ratio. The culture supernatants were collected and probed for IL-15 and IL-21 using the U-PLEX assay platform (Meso Scale Diagnostics, Rockville, MD). The results are shown in FIGS. 6A-6B.

FIGS. 6A-6B show the levels of IL-15 (FIG. 6A) and IL-21 (FIG. 6B) measured in the supernatants of the transduced cells. IL-15 levels were barely detectable in the supernatants from T cells transduced with TeIL-15 Lr1Ar2 (14.54 pg/ml) and TeIL-21/15 FurinA-P2A Ar2 (2.18 pg/ml) (FIG. 6A), while IL-21 levels were clearly detectable in the supernatants from T cells transduced with TeIL-21 Lr8Ar2 (2211.25 pg/ml) and TeIL-21/15 FurinA-P2A Ar2 (1234.02 pg/ml) (FIG. 6B). IL-15 levels and IL-21 levels were much lower in the supernatants from T cells transduced with tethered cytokines (TeIL-15 Lr1Ar2, TeIL-21 Lr8Ar2, and TeIL-21/15 FurinA-P2A Ar2) as compared to that of T cells transduced with secreted IL-21/15 (IL-15: 988.37 pg/ml; IL-21: >13100.00 pg/ml) (FIGS. 6A-6B).

FIGS. 6C-6D show the levels of IL-15 (FIG. 6C) and IL-21 (FIG. 6D) measured in the supernatants of the co-culture of the transduced T cells with target tumor cell lines. As shown in FIGS. 6C-6D, a small amount of IL-15 (TeIL-15 Lr1Ar2: 6.88-26.09 pg/ml; TeIL-21/15 FurinA-P2A Ar2: 0.71-12.87 pg/ml) and some IL-21 (TeIL-21 Lr8Ar2: 152.41-1408.79 pg/ml; TeIL-21/15 FurinA-P2A Ar2: 146.23-1135.04 pg/ml) can be detected in the supernatants of the co-culture of the transduced T cells with target tumor cell lines.

Example 11

This example demonstrates that T cells transduced with TeIL-21/15 FurinA-P2A Ar2 shed less IL-15 and IL-21 in vivo as compared to T cells transduced with secreted IL-21/15.

Healthy NSG mice were infused with untransduced human T cells, HBSS (without cells), or human T cells transduced with one of (i)-(iii), as follows:
- (i.) E7 TCR and TeIL-21/15 FurinA-P2A Ar2,
- (ii.) E7 TCR and secreted IL-21/15 (sIL-21/15) (positive control), or
- (iii.) E7 TCR alone (control).

The sera were collected at the time points shown in FIGS. 7A-7B and assayed for IL-15 and IL-21 using the U-PLEX assay platform. The results are shown in FIGS. 7A-7B. At each time point, two mouse serum samples were assayed. The concentration of IL-15 was below the limit of detection in the sera of healthy NSG mice infused with TeIL-21/15 FurinA-P2A Ar2 T cells (FIG. 7A), while IL-21 was detected at a low concentration in the same sera (FIG. 7B).

In another experiment, NSG mice bearing palpable tumors derived from the CaSki tumor cell line were infused with untransduced human T cells, HBSS (without cells), or human T cells transduced with one of (i)-(v), as follows:
- (i.) E7 TCR and TeIL-15 Lr1Ar2,
- (ii.) E7 TCR and TeIL-21 Lr8Ar2,
- (iii.) E7 TCR and TeIL-21/15 FurinA-P2A Ar2,
- (iv.) E7 TCR and secreted IL-21/15 (sIL-21/15) (positive control), or
- (v.) E7 TCR alone (control).

The sera were collected at the time points shown in FIGS. 7C-7D and assayed for IL-15 and IL-21 using the U-PLEX assay platform. The results are shown in FIGS. 7C-7D. At each time point, one mouse serum sample was assayed. In the sera of tumor-bearing mice receiving transduced T cells, a trace amount of IL-15 was detected at early time points (Day 8 and 9 after T cell infusion) in mice receiving T cells transduced with E7 TCR and TeIL-21/15 FurinA-P2A Ar2, and a small amount of IL-15 was detected in mice receiving T cells transduced with E7 TCR and TeIL-15 Lr1 Ar2 (FIG. 7C). A small amount of IL-21 was detected in the sera of mice infused with TeIL-21/15 FurinA-P2A Ar2 T cells (FIG. 7D).

Example 12

This example demonstrates the serum inflammatory cytokine profile in tumor-bearing mice after infusion of cells transduced with TeIL-21/15 FurinA-P2A Ar2.

NSG mice with palpable tumors derived from the CaSki tumor cell line were infused with untransduced human T cells, HBSS (without cells), or human T cells transduced with one of (i)-(v), as follows:
- (i.) E7 TCR and TeIL-15 Lr1Ar2,
- (ii.) E7 TCR and TeIL-21 Lr8Ar2,
- (iii.) E7 TCR and TeIL-21/15 FurinA-P2A Ar2,
- (iv.) E7 TCR and secreted IL-21/15 (sIL-21/15) (positive control), or
- (v.) E7 TCR alone (control).

The sera were collected at four-time points (Day 8, 9, 15, and 29 after T cell infusion) and assayed for inflammatory cytokine profile using the U-PLEX assay platform.

Figure 8B:
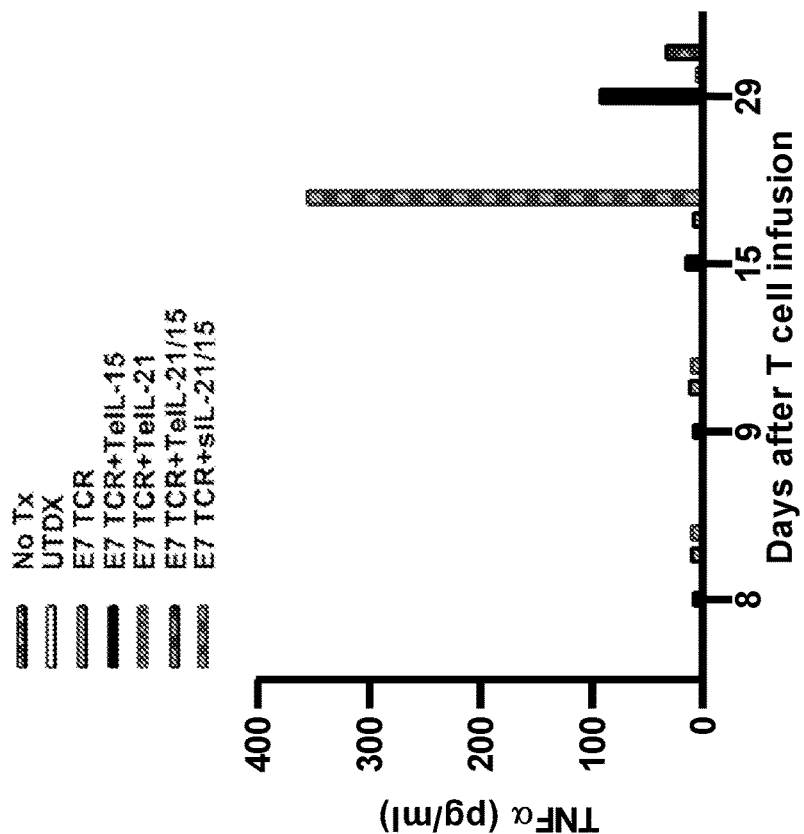
Figure 8A:
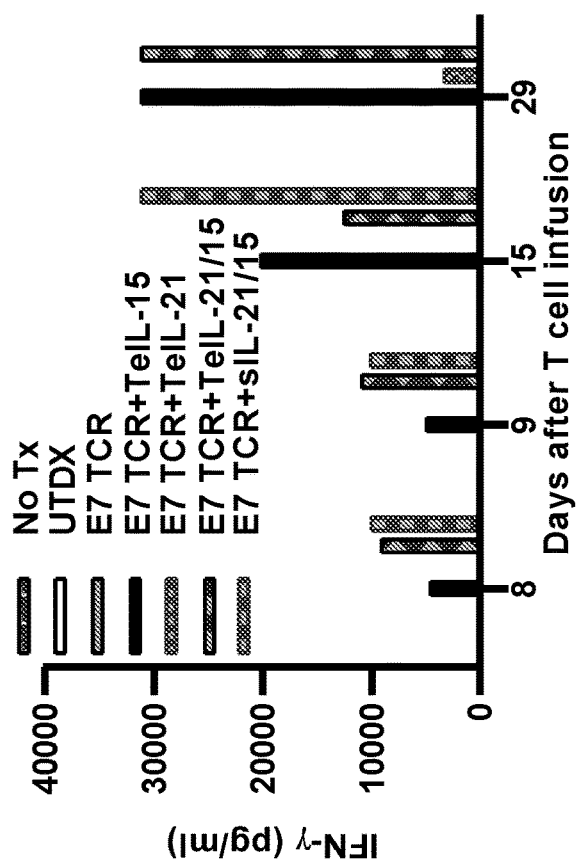
Figure 8D:
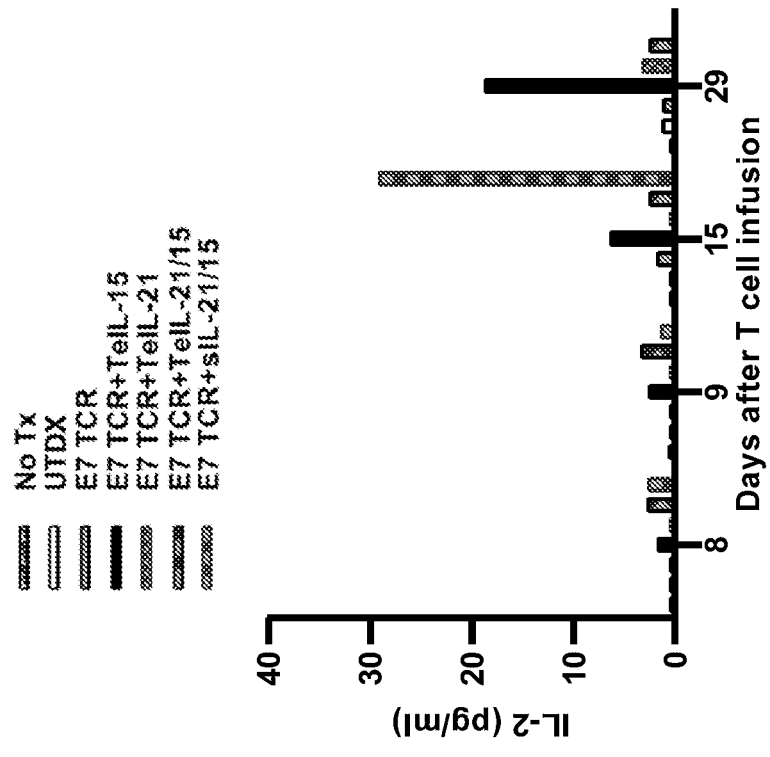
Figure 8C:
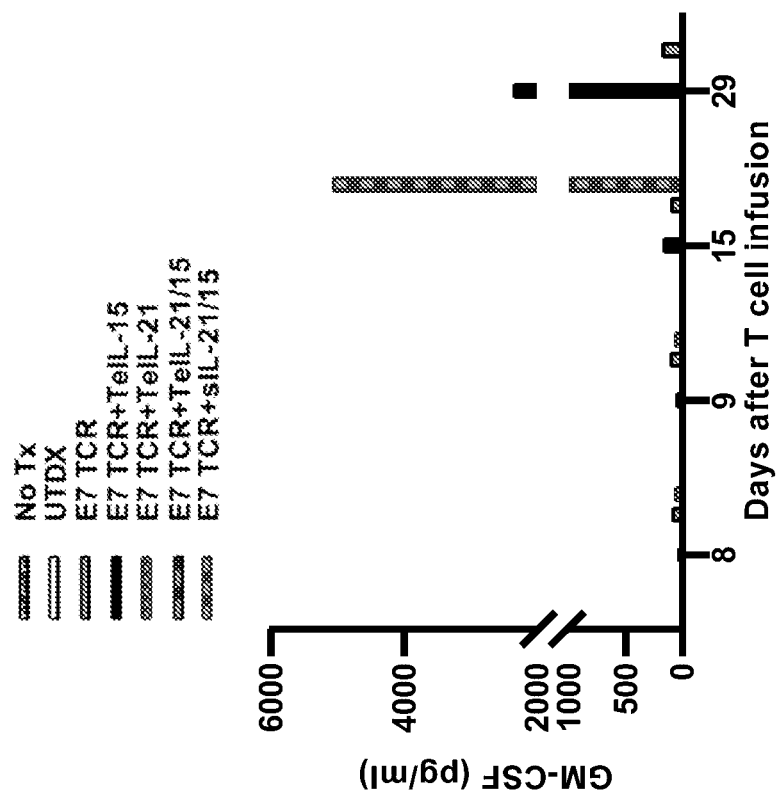
Figure 8F:
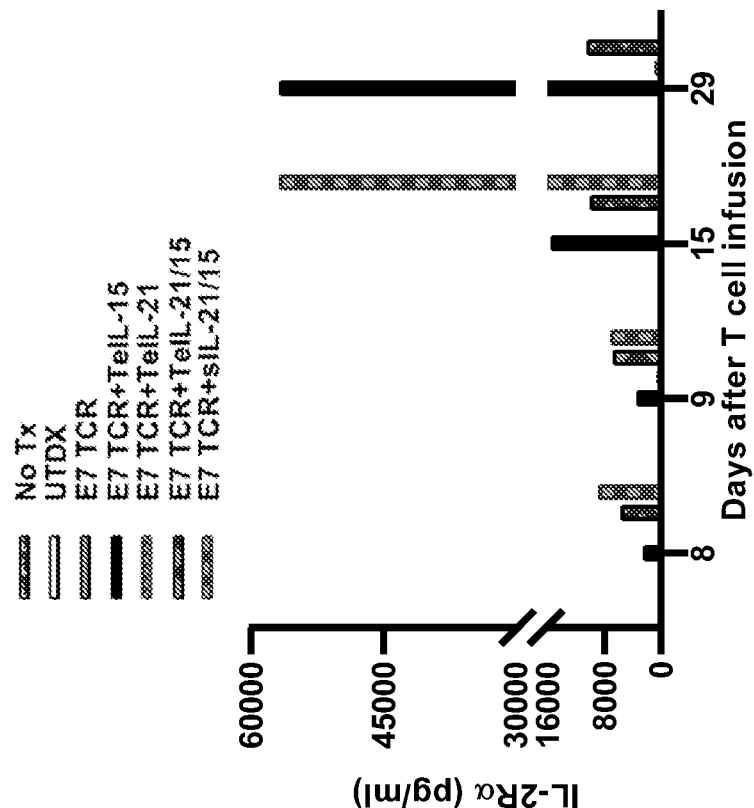
Figure 8E:
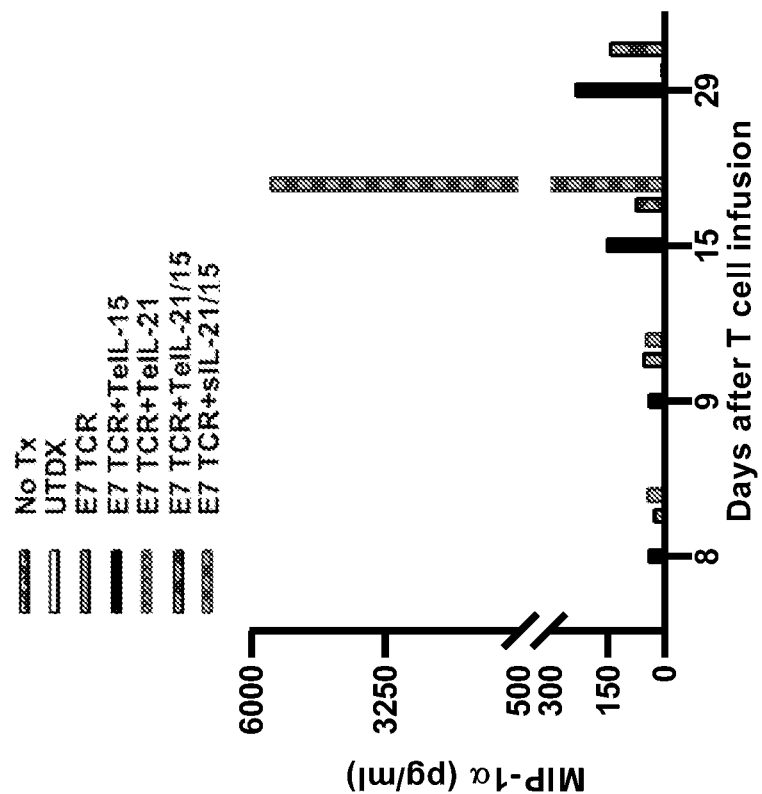
Figure 8G:
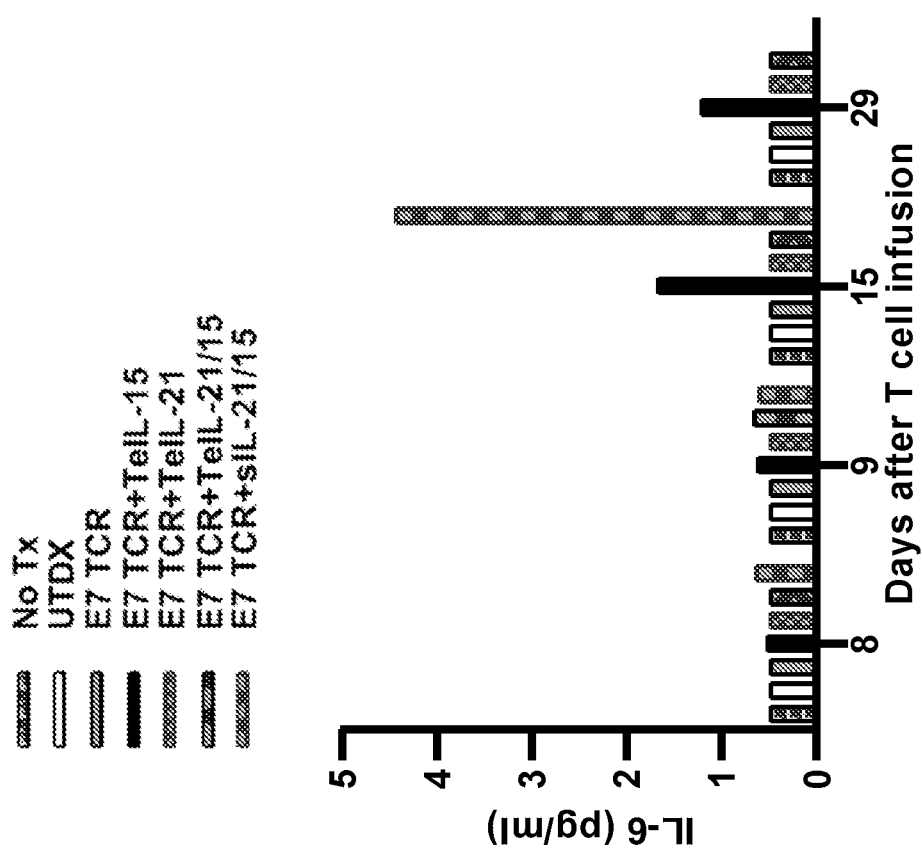

The results are shown in FIGS. 8A-8G. Elevated levels of cytokines, including IFN-γ, TNF-α, GM-CSF, IL-2, MIP-1α and IL-2Rα, were observed in the sera of tumor-bearing mice receiving T cells transduced with E7 TCR and TeIL-12/15 FurinA-P2A Ar2 at all-time points when compared to the control groups of mice which received untransduced T cells or T cells transduced with E7 TCR, respectively (FIGS. 8A-8F). IL-6 has been reported to be a leading factor for cytokine storm in CAR T cell therapy. Here, the results showed that the IL-6 level was below the low detection limit in the sera of mice infused with T cells transduced with E7 TCR and TeIL-21/15 FurinA-P2A Ar2 (FIG. 8G). A slight increase of IL-6 was detected in the sera of mice receiving T cells transduced with E7 TCR and TeIL-15 Lr1Ar2 at day 15 and 29 after T cell infusion (FIG. 8G).

Example 13

This example demonstrates that tumor-bearing mice treated with T cells co-transduced with E7 TCR and TeIL-21/15 FurinA-P2A Ar2 undergo tumor regression.

NSG mice were subcutaneously inoculated with $2.5 \times 10^6$ CaSki tumor cells. One week later, the mice with established tumors were treated with a single intravenous injection of 5 million T cells in 0.5 ml of HBSS. The injected T cells were transduced with one of (i)-(iv), as follows:

- (i.) E7 TCR and NFAT.IL12 (IL-12 under the control of a nuclear factor of activated T-cells (NFAT)-responsive promoter),
- (ii.) E7 TCR and TeIL-21/15 FurinA-P2A Ar2 and NFA-T.IL12,
- (iii.) E7 TCR and TeIL-21/15 FurinA-P2A Ar2, or
- (iv.) E7 TCR alone (control).

Untreated mice served as a control. Tumor size was measured using a digital caliper every 3-4 days. The results are shown in FIG. 9. The mice receiving T cells transduced with the E7 TCR alone demonstrated a similar tumor growth curve as that of control mice receiving no treatment. The mice receiving T cells co-transduced with E7 TCR and NFAT. IL12 only showed delayed tumor progression. Both the mice receiving T cells co-transduced with E7 TCR and TeIL-21/15 FurinA-P2A Ar2 and the mice receiving T cells cotransduced with E7 TCR and TeIL-21/15 FurinA-P2A Ar2 and NFAT.IL12 demonstrated substantial tumor regression at day 51 after T cell infusion. At day 63 after T cell infusion, three mice receiving T cells co-transduced with E7 TCR and TeIL-21/15 FurinA-P2A Ar2 displayed complete tumor regression, while four mice receiving T cells co-transduced with E7 TCR and TeIL-21/15 FurinA-P2A Ar2 and NFA-T.IL12 presented small-sized tumors.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A T cell comprising a cell surface membrane, wherein the T cell comprises a nucleic acid molecule encoding a polypeptide consisting of a signal sequence, a human IL-15 amino acid sequence, a linker, and a cell membrane anchor moiety, wherein the linker binds the human IL-15 amino acid sequence to the cell membrane anchor moiety, and the cell membrane anchor moiety binds the IL-15 amino acid sequence to the cell surface membrane of the T cell, wherein the signal sequence is a human granulocyte-macrophage colony-stimulating factor (GM-CSF) receptor signal sequence, a human prolactin signal sequence, or a human IgE signal sequence;

wherein the cell membrane anchor moiety is a B7-1 transmembrane-intracellular amino acid sequence, a B7-2 transmembrane-intracellular amino acid sequence, a CD8α transmembrane-intracellular amino acid sequence, a B7-1 transmembrane amino acid sequence, a B7-2 transmembrane amino acid sequence, or a CD8α transmembrane amino acid sequence;

wherein the human IL-15 amino acid sequence comprises an amino acid sequence at least 90% identical to the amino acid sequence of SEQ ID NO: 3; and wherein the linker sequence is a polypeptide of Formula III: $X^1_m X^2_n X^3_p X^4_q$ (Formula III), wherein:

each of m, p, and q is, independently, 0 or 1;

n is an integer from 20 to 65;

$X^2$ is independently selected from glycine and serine; and each of $X^1$, $X^3$, and $X^4$ is, independently, any one naturally occurring amino acid residue.

2. The T cell of claim 1, wherein the IL-15 amino acid sequence comprises the amino acid sequence set forth in SEQ ID NO:3.

3. The T cell of claim 1, wherein the cell membrane anchor moiety comprises the amino acid sequence set forth in SEQ ID NO:5.

4. The T cell of claim 1, wherein the nucleic acid molecule is comprised in a recombinant expression vector.

5. The T cell of claim 4, wherein the vector is a viral vector.

6. The T cell of claim 5, wherein the viral vector is a lentiviral vector, a retroviral vector, an alphaviral vector, a vaccinial viral vector, an adenoviral vector, an adenoassociated viral vector, a herpes viral vector, or a fowl pox viral vector.

7. The T cell of claim 1, wherein the T cell is a tumor infiltrating lymphocyte (TIL).

8. A pharmaceutical composition comprising the T cell of claim 7 and a pharmaceutically acceptable carrier.

* * * * *